(12) United States Patent
Freyman et al.

(10) Patent No.: US 12,046,327 B1
(45) Date of Patent: Jul. 23, 2024

(54) IDENTITY-BY-DESCENT RELATEDNESS BASED ON FOCAL AND REFERENCE SEGMENTS

(71) Applicant: 23andMe, Inc., Sunnyvale, CA (US)

(72) Inventors: William A. Freyman, Menlo Park, CA (US); Kimberly F. McManus, San Francisco, CA (US); Suyash S. Shringarpure, Mountain View, CA (US); Ethan M. Jewett, San Jose, CA (US); Adam Auton, Menlo Park, CA (US)

(73) Assignee: 23andMe, Inc., Sunnyvale, CA (US)

( * ) Notice: Subject to any disclaimer, the term of this patent is extended or adjusted under 35 U.S.C. 154(b) by 0 days.

(21) Appl. No.: 18/503,841

(22) Filed: Nov. 7, 2023

Related U.S. Application Data

(63) Continuation of application No. 16/947,107, filed on Jul. 17, 2020.
(Continued)

(51) Int. Cl.
*G16B 30/00* (2019.01)
*G16B 50/30* (2019.01)

(52) U.S. Cl.
CPC ............. *G16B 30/00* (2019.02); *G16B 50/30* (2019.02)

(58) Field of Classification Search
None
See application file for complete search history.

(56) References Cited

U.S. PATENT DOCUMENTS

| | | |
|---|---|---|
| 5,692,501 A | 12/1997 | Minturn |
| 6,570,567 B1 | 5/2003 | Eaton |

(Continued)

FOREIGN PATENT DOCUMENTS

| | | |
|---|---|---|
| WO | 2004097712 A2 | 11/2004 |
| WO | 2006089238 W | 8/2006 |

(Continued)

OTHER PUBLICATIONS

Cardena, et al., "Assessment of the Relationship between Self-Declared Ethnicity, Mitochondrial Haplogroups and Genomic Ancestry in Brazilian Individuals," PLoS One, vol. 8, No. 4, Apr. 24, 2013, pp. 1-6.
(Continued)

*Primary Examiner* — Kaveh Abrishamkar
(74) *Attorney, Agent, or Firm* — McDonnell Boehnen Hulbert & Berghoff LLP; David K. Buckingham

(57) ABSTRACT

Example embodiments relate to identity-by-descent (IBD) relatedness based on focal and reference segments. An example method includes determining, by a services platform based on personal information of a focal individual, a focal string. The method also includes retrieving, by the services platform from a reference database, a reference string of a reference individual. Additionally, the method includes computationally identifying, by the services platform, IBD segments between the focal string and the reference string. Further, the method includes determining, by the services platform and based on the merged set of IBD segments, a degree of relatedness between the focal individual and the reference individual. In addition, the method includes providing, by the services platform, access to the degree of relatedness via a user interface.

20 Claims, 30 Drawing Sheets

Phase Switch Errors

Related U.S. Application Data

(60) Provisional application No. 62/876,497, filed on Jul. 19, 2019.

(56) References Cited

U.S. PATENT DOCUMENTS

| | | |
|---|---|---|
| 6,703,228 B1 | 3/2004 | Landers |
| 7,142,205 B2 | 11/2006 | Chithambaram |
| 7,567,894 B2 | 7/2009 | Durand |
| 7,729,863 B2 | 6/2010 | Ostrander |
| 7,797,302 B2 | 9/2010 | Kenedy |
| 7,818,281 B2 | 10/2010 | Kennedy |
| 7,818,310 B2 | 10/2010 | Kenedy |
| 7,844,609 B2 | 11/2010 | Kenedy |
| 7,848,914 B2 | 12/2010 | Durand |
| 7,917,438 B2 | 3/2011 | Kenedy |
| 7,933,912 B2 | 4/2011 | Kenedy |
| 7,941,329 B2 | 5/2011 | Kenedy |
| 7,941,434 B2 | 5/2011 | Kenedy |
| 7,951,078 B2 | 5/2011 | Scheuner |
| 7,957,907 B2 | 6/2011 | Sorenson |
| 7,983,893 B2 | 7/2011 | Durand |
| 8,024,348 B2 | 9/2011 | Kenedy |
| 8,051,033 B2 | 11/2011 | Kenedy |
| 8,055,643 B2 | 11/2011 | Kenedy |
| 8,065,324 B2 | 11/2011 | Kenedy |
| 8,099,424 B2 | 1/2012 | Kenedy |
| 8,108,406 B2 | 1/2012 | Kenedy |
| 8,156,158 B2 | 4/2012 | Rolls |
| 8,185,461 B2 | 5/2012 | Kenedy |
| 8,187,811 B2 | 5/2012 | Eriksson |
| 8,195,446 B2 | 6/2012 | Durand |
| 8,200,509 B2 | 6/2012 | Kenedy |
| 8,207,316 B1 | 6/2012 | Bentwich |
| 8,209,319 B2 | 6/2012 | Kenedy |
| 8,214,192 B2 | 7/2012 | Durand |
| 8,214,195 B2 | 7/2012 | Durand |
| 8,224,835 B2 | 7/2012 | Kenedy |
| 8,255,403 B2 | 8/2012 | Kenedy |
| 8,285,486 B2 | 10/2012 | Martin |
| 8,326,648 B2 | 12/2012 | Kenedy |
| 8,386,519 B2 | 2/2013 | Kenedy |
| 8,428,886 B2 | 4/2013 | Wong |
| 8,443,339 B2 | 5/2013 | Letourneau |
| 8,452,619 B2 | 5/2013 | Kenedy |
| 8,458,097 B2 | 6/2013 | Kenedy |
| 8,458,121 B2 | 6/2013 | Kenedy |
| 8,463,554 B2 | 6/2013 | Hon |
| 8,467,976 B2 | 6/2013 | Lo |
| 8,473,273 B2 | 6/2013 | Durand |
| 8,510,057 B1 | 8/2013 | Avey |
| 8,543,339 B2 | 9/2013 | Wojcicki |
| 8,589,437 B1 | 11/2013 | Khomenko |
| 8,606,761 B2 | 12/2013 | Kenedy |
| 8,645,118 B2 | 2/2014 | Durand |
| 8,645,343 B2 | 2/2014 | Wong |
| 8,655,899 B2 | 2/2014 | Kenedy |
| 8,655,908 B2 | 2/2014 | Kenedy |
| 8,655,915 B2 | 2/2014 | Kenedy |
| 8,666,271 B2 | 3/2014 | Saiki |
| 8,666,721 B2 | 3/2014 | Durand |
| 8,685,737 B2 | 4/2014 | Serber |
| 8,719,045 B2 | 5/2014 | Yoon |
| 8,731,819 B2 | 5/2014 | Dzubay |
| 8,738,297 B2 | 5/2014 | Sorenson |
| 8,786,603 B2 | 7/2014 | Rasmussen |
| 8,788,283 B2 | 7/2014 | Kenedy |
| 8,788,286 B2 | 7/2014 | Kenedy |
| 8,798,915 B2 | 8/2014 | Dzubay |
| 8,855,935 B2 | 10/2014 | Myres |
| 8,990,198 B2 | 3/2015 | Rolls |
| 8,990,250 B1 | 3/2015 | Chowdry |
| 9,026,423 B2 | 5/2015 | Durand |
| 9,031,870 B2 | 5/2015 | Kenedy |
| 9,116,882 B1 | 8/2015 | MacPherson |
| 9,170,992 B2 | 10/2015 | Kenedy |
| 9,213,944 B1 | 12/2015 | Do |
| 9,213,947 B1 | 12/2015 | Do |
| 9,218,451 B2 | 12/2015 | Wong |
| 9,262,567 B2 | 2/2016 | Durand |
| 9,323,632 B2 | 4/2016 | Durand |
| 9,336,177 B2 | 5/2016 | Hawthorne |
| 9,367,663 B2 | 6/2016 | Deciu |
| 9,367,800 B1 | 6/2016 | Do |
| 9,390,225 B2 | 7/2016 | Barber |
| 9,405,818 B2 | 8/2016 | Chowdry |
| 9,582,647 B2 | 2/2017 | Kenedy |
| 9,836,576 B1 | 12/2017 | Do |
| 9,864,835 B2 | 1/2018 | Avey |
| 9,886,576 B2 | 2/2018 | Urakabe |
| 9,977,708 B1 | 5/2018 | Do |
| 10,025,877 B2 | 7/2018 | MacPherson |
| 10,127,346 B2 | 11/2018 | Dewey |
| 10,162,880 B1 | 12/2018 | Chowdry |
| 10,275,569 B2 | 4/2019 | Avey |
| 10,296,847 B1 | 5/2019 | Do |
| 10,379,812 B2 | 8/2019 | Kenedy |
| 10,432,640 B1 | 10/2019 | Hawthorne |
| 10,437,858 B2 | 10/2019 | Naughton |
| 10,516,670 B2 | 12/2019 | Hawthorne |
| 10,572,831 B1 | 2/2020 | Do |
| 10,643,740 B2 | 5/2020 | Avey |
| 10,658,071 B2 | 5/2020 | Do |
| 10,691,725 B2 | 6/2020 | Naughton |
| 10,699,803 B1 | 6/2020 | Do |
| 10,755,805 B1 | 8/2020 | Do |
| 10,777,302 B2 | 9/2020 | Chowdry |
| 10,790,041 B2 | 9/2020 | MacPherson |
| 10,803,134 B2 | 10/2020 | Kenedy |
| 10,841,312 B2 | 11/2020 | Hawthorne |
| 10,854,318 B2 | 12/2020 | MacPherson |
| 10,891,317 B1 | 1/2021 | Chowdry |
| 10,896,233 B2 | 1/2021 | Kenedy |
| 10,936,626 B1 | 3/2021 | Naughton |
| 10,957,455 B2 | 3/2021 | Kenedy |
| 10,991,467 B2 | 4/2021 | Kenedy |
| 10,999,285 B2 | 5/2021 | Hawthorne |
| 11,003,694 B2 | 5/2021 | Kenedy |
| 11,031,101 B2 | 6/2021 | Hon |
| 11,049,589 B2 | 6/2021 | Hon |
| 11,170,047 B2 | 11/2021 | MacPherson |
| 11,170,873 B2 | 11/2021 | Avey |
| 11,171,962 B2 | 11/2021 | Hawthorne |
| 11,322,227 B2 | 5/2022 | Hon |
| 2002/0095585 A1 | 7/2002 | Scott |
| 2002/0133495 A1 | 9/2002 | Hugh, Jr. |
| 2003/0113727 A1 | 6/2003 | Girn |
| 2003/0113729 A1 | 6/2003 | Daquino |
| 2003/0130798 A1 | 7/2003 | Hood |
| 2003/0135096 A1 | 7/2003 | Dodds |
| 2003/0172065 A1 | 9/2003 | Sorenson |
| 2003/0179223 A1 | 9/2003 | Ying |
| 2003/0186244 A1 | 10/2003 | Margus |
| 2004/0002818 A1 | 1/2004 | Kulp |
| 2004/0088191 A1 | 5/2004 | Holden |
| 2004/0146870 A1 | 7/2004 | Liao |
| 2004/0175700 A1 | 9/2004 | Geesaman |
| 2004/0229213 A1 | 11/2004 | Legrain |
| 2004/0229231 A1 | 11/2004 | Frudakis |
| 2004/0241730 A1 | 12/2004 | Yakhini |
| 2005/0039110 A1 | 2/2005 | De La Vega |
| 2005/0191731 A1 | 9/2005 | Judson |
| 2005/0250151 A1 | 11/2005 | Mei |
| 2006/0003354 A1 | 1/2006 | Krantz |
| 2006/0046256 A1 | 3/2006 | Halldorsson |
| 2006/0100872 A1 | 5/2006 | Yokoi |
| 2006/0142949 A1 | 6/2006 | Helt |
| 2006/0161460 A1 | 7/2006 | Smitherman |
| 2006/0166224 A1 | 7/2006 | Norviel |
| 2006/0257888 A1 | 11/2006 | Zabeau |
| 2006/0287876 A1 | 12/2006 | Jedlicka |
| 2007/0037182 A1 | 2/2007 | Gaskin |
| 2007/0150978 A1* | 6/2007 | Byrum ............. C07K 14/415 536/23.6 |
| 2007/0178500 A1 | 8/2007 | Martin |

(56) References Cited

U.S. PATENT DOCUMENTS

| | | |
|---|---|---|
| 2007/0250809 A1 | 10/2007 | Kennedy |
| 2007/0277267 A1 | 11/2007 | Byrum |
| 2008/0004848 A1 | 1/2008 | Avey |
| 2008/0081331 A1 | 4/2008 | Myres |
| 2008/0131887 A1 | 6/2008 | Stephan |
| 2008/0154566 A1 | 6/2008 | Myres |
| 2008/0189047 A1 | 8/2008 | Wong |
| 2008/0227063 A1 | 9/2008 | Kenedy |
| 2008/0228043 A1 | 9/2008 | Kenedy |
| 2008/0228410 A1 | 9/2008 | Kenedy |
| 2008/0228451 A1 | 9/2008 | Kenedy |
| 2008/0228677 A1 | 9/2008 | Kenedy |
| 2008/0228698 A1 | 9/2008 | Kenedy |
| 2008/0228699 A1 | 9/2008 | Kenedy |
| 2008/0228700 A1 | 9/2008 | Kenedy |
| 2008/0228701 A1 | 9/2008 | Kenedy |
| 2008/0228702 A1 | 9/2008 | Kenedy |
| 2008/0228704 A1 | 9/2008 | Kenedy |
| 2008/0228705 A1 | 9/2008 | Kenedy |
| 2008/0228706 A1 | 9/2008 | Kenedy |
| 2008/0228708 A1 | 9/2008 | Kenedy |
| 2008/0228722 A1 | 9/2008 | Kenedy |
| 2008/0228753 A1 | 9/2008 | Kenedy |
| 2008/0228756 A1 | 9/2008 | Kenedy |
| 2008/0228757 A1 | 9/2008 | Kenedy |
| 2008/0228765 A1 | 9/2008 | Kenedy |
| 2008/0228766 A1 | 9/2008 | Kenedy |
| 2008/0228767 A1 | 9/2008 | Kenedy |
| 2008/0228768 A1 | 9/2008 | Kenedy |
| 2008/0228797 A1 | 9/2008 | Kenedy |
| 2008/0243843 A1 | 10/2008 | Kenedy |
| 2008/0255768 A1 | 10/2008 | Martin |
| 2008/0270366 A1 | 10/2008 | Frank |
| 2009/0043752 A1 | 2/2009 | Kenedy |
| 2009/0099789 A1 | 4/2009 | Stephan |
| 2009/0112871 A1 | 4/2009 | Hawthorne |
| 2009/0118131 A1 | 5/2009 | Avey |
| 2009/0119083 A1 | 5/2009 | Avey |
| 2009/0182579 A1 | 7/2009 | Liu |
| 2009/0198519 A1 | 8/2009 | McNamar |
| 2009/0299645 A1 | 12/2009 | Colby |
| 2010/0042438 A1 | 2/2010 | Moore |
| 2010/0063830 A1 | 3/2010 | Kenedy |
| 2010/0063835 A1 | 3/2010 | Kenedy |
| 2010/0063865 A1 | 3/2010 | Kenedy |
| 2010/0070292 A1 | 3/2010 | Kenedy |
| 2010/0070455 A1 | 3/2010 | Halperin |
| 2010/0076950 A1 | 3/2010 | Kenedy |
| 2010/0076988 A1 | 3/2010 | Kenedy |
| 2010/0145981 A1 | 6/2010 | Wojcicki |
| 2010/0169262 A1 | 7/2010 | Kenedy |
| 2010/0169313 A1 | 7/2010 | Kenedy |
| 2010/0169338 A1 | 7/2010 | Kenedy |
| 2010/0191513 A1 | 7/2010 | Listgarten |
| 2010/0281401 A1 | 11/2010 | Tebbs |
| 2011/0078168 A1 | 3/2011 | Kenedy |
| 2011/0130337 A1 | 6/2011 | Eriksson |
| 2011/0184656 A1 | 7/2011 | Kenedy |
| 2011/0257889 A1 | 10/2011 | Klammer |
| 2012/0270190 A1 | 10/2012 | Kenedy |
| 2012/0270794 A1 | 10/2012 | Eriksson |
| 2012/0301864 A1 | 11/2012 | Bagchi |
| 2013/0080068 A1 | 3/2013 | Dewey |
| 2013/0080365 A1 | 3/2013 | Dewey |
| 2013/0085728 A1 | 4/2013 | Tang |
| 2013/0149707 A1 | 6/2013 | Sorenson |
| 2013/0345988 A1 | 12/2013 | Avey |
| 2014/0006433 A1 | 1/2014 | Hon |
| 2014/0045705 A1 | 2/2014 | Bustamante |
| 2014/0067280 A1 | 3/2014 | Vockley |
| 2014/0067355 A1 | 3/2014 | Noto |
| 2015/0227610 A1 | 8/2015 | Chowdry |
| 2015/0248473 A1 | 9/2015 | Kenedy |
| 2015/0347566 A1 | 12/2015 | Kenedy |
| 2016/0026755 A1 | 1/2016 | Byrnes |
| 2016/0103950 A1 | 4/2016 | Myres |
| 2016/0171155 A1 | 6/2016 | Do |
| 2016/0277408 A1 | 9/2016 | Hawthorne |
| 2016/0350479 A1* | 12/2016 | Han ............... G16C 20/60 |
| 2017/0011042 A1 | 1/2017 | Kermany |
| 2017/0017752 A1 | 1/2017 | Noto |
| 2017/0053089 A1 | 2/2017 | Kenedy |
| 2017/0185719 A1 | 6/2017 | Kenedy |
| 2017/0220738 A1 | 8/2017 | Barber |
| 2017/0228498 A1 | 8/2017 | Hon |
| 2017/0262577 A1 | 9/2017 | Ball |
| 2017/0277827 A1 | 9/2017 | Granka |
| 2017/0277828 A1 | 9/2017 | Avey |
| 2017/0329866 A1 | 11/2017 | MacPherson |
| 2017/0329891 A1 | 11/2017 | MacPherson |
| 2017/0329899 A1 | 11/2017 | Bryc |
| 2017/0329901 A1 | 11/2017 | Chowdry |
| 2017/0329902 A1 | 11/2017 | Bryc |
| 2017/0329904 A1 | 11/2017 | Naughton |
| 2017/0329915 A1 | 11/2017 | Kittredge |
| 2017/0329924 A1 | 11/2017 | MacPherson |
| 2017/0330358 A1 | 11/2017 | MacPherson |
| 2018/0181710 A1 | 6/2018 | Avey |
| 2018/0307778 A1 | 10/2018 | MacPherson |
| 2019/0012431 A1 | 1/2019 | Hon |
| 2019/0026604 A1 | 1/2019 | Sharma |
| 2019/0034163 A1 | 1/2019 | Kenedy |
| 2019/0114219 A1 | 4/2019 | Do |
| 2019/0139623 A1 | 5/2019 | Bryc |
| 2019/0206514 A1 | 7/2019 | Avey |
| 2019/0267115 A1 | 8/2019 | Avey |
| 2019/0281061 A1 | 9/2019 | Hawthorne |
| 2019/0384777 A1 | 12/2019 | Naughton |
| 2020/0137063 A1 | 4/2020 | Hawthorne |
| 2020/0210143 A1 | 7/2020 | Kenedy |
| 2020/0273542 A1* | 8/2020 | Song ............... G16B 40/30 |
| 2020/0321073 A1* | 10/2020 | Zhi ............... G06F 16/22 |
| 2020/0372974 A1 | 11/2020 | Chowdry |
| 2021/0020266 A1* | 1/2021 | Freyman ............... G16B 30/10 |
| 2021/0043278 A1 | 2/2021 | Hon |
| 2021/0043279 A1 | 2/2021 | Hon |
| 2021/0043280 A1 | 2/2021 | Hon |
| 2021/0043281 A1 | 2/2021 | MacPherson |
| 2021/0058398 A1 | 2/2021 | Hawthorne |
| 2021/0074385 A1 | 3/2021 | Hon |
| 2021/0082167 A1 | 3/2021 | Jewett |
| 2021/0166452 A1 | 6/2021 | Jewett |
| 2021/0166823 A1 | 6/2021 | Kenedy |
| 2021/0193257 A1 | 6/2021 | Freyman |
| 2021/0209134 A1 | 7/2021 | Kenedy |
| 2021/0225458 A1 | 7/2021 | Hon |
| 2021/0233665 A1 | 7/2021 | Kenedy |
| 2021/0250357 A1 | 8/2021 | Hawthorne |
| 2021/0313013 A1 | 10/2021 | Hon |
| 2021/0375392 A1 | 12/2021 | Polcari |
| 2022/0044761 A1 | 2/2022 | O'Connell |
| 2022/0051751 A1 | 2/2022 | Wilton |
| 2022/0103560 A1 | 3/2022 | Hawthorne |
| 2022/0115139 A1 | 4/2022 | Paradarami |
| 2022/0139501 A1 | 5/2022 | Hon |
| 2022/0157405 A1 | 5/2022 | Avey |
| 2022/0198726 A1 | 6/2022 | Jewett |
| 2022/0223233 A1 | 7/2022 | Bryc |

FOREIGN PATENT DOCUMENTS

| | | |
|---|---|---|
| WO | 2009002942 W | 12/2008 |
| WO | 2009042975 W | 4/2009 |
| WO | 2012099890 W | 7/2012 |
| WO | 2016073953 W | 5/2016 |
| WO | 2017009788 A1 | 1/2017 |
| WO | 2021243094 W | 12/2021 |
| WO | 2022036178 W | 2/2022 |
| WO | 2022076909 W | 4/2022 |
| WO | 2022087478 W | 4/2022 |

(56) References Cited

OTHER PUBLICATIONS

Carmi, S. et al., "Sequencing and Ashkenazi reference panel supports population-targeted personal genomics and illuminates Jewish and European origins" Nat. Commun. 5, Sep. 9, 2014, 4835.
Chiang, et al., "Conflation of Short Identity-by-Descent Segments Bias Their Inferred Length Distribution", G3 Genes|Genomes|Genetics, vol. 6, No. 5, May 1, 2016, pp. 1287-1296.
Choi, et al., "Comparison of phasing strategies for whole human genomes" PLoS Genetics, 14(4): e1007308, Apr. 5, 2018, pp. 1-26.
Churchhouse, et al., "Multiway Admixture Deconvolution Using Phased or Unphased Ancestral Panels," Wiley Periodical, Inc., Genetic Epidemiology, 2012, pp. 1-12.
De Francesco, L., et al., "Efficient Genotype Elimination Via Adaptive Allele Consolidation," IEEE/ACM Transactions on Computational Biology and Bioinformatics (TCBB), vol. 9, No. 4, Jul. 2012, pp. 1180-1189.
Dean, M., et al., "Polymorphic Admixture Typing in Human Ethnic Populations," American Journal of Human Genetics, vol. 55:4, 1994, pp. 788-808.
Delaneau, et al., "A Linear complexity phasing method for thousands of genomes," Nature Methods, vol. 9, No. 2, Feb. 2012, pp. 179-184.
Delaneau, et al., "Accurate, scalable and integrative haplotype estimation," Nature Communications, (2019) 10:5436, pp. 1-20.
Delaneau, et al., "Integrative haplotype estimation with sub-linear complexity" bioRxiv, Jan. 1, 2018, 493403.
Dempster, et al., "Maximum likelihood from incomplete data via the EM algorithm" Journal of the Royal Statistical Society, Series B, 39(1), 1977, pp. 1-38.
Diaz-Papkovich, et al., "UMAP reveals cryptic population structure and phenotype heterogeneity in large genomic cohorts" PLOS Genetics, 15(II):e1008432, Nov. 1, 2019, pp. 1-24.
DODECAD Project, [webpage] "Clusters Galore results, K=73 for Dodecad Project members (up to DOD581)" Dodecad Ancestry Project (Internet Blog), published Mar. 31, 2011, pp. 1-11. [retrieved May 23, 2018].
Dr. D., [webpage] "Population Finder Traces Deep Ancestry," Dr. D Digs Up Ancestors (Internet Blog), DNA Testing, published online Apr. 9, 2011, p. 1. [retrieved May 23, 2018].
Druet, Tom, et al., "A Hidden Markov Model Combining Linkage and Linkage Disequilibrium Information for Haplotype Reconstruction and Quantitative Trait Locus Fine Mapping," Genetics vol. 184, No. 3, Jun. 2010, pp. 789-798.
Durand, E.Y. et al. "Reducing Pervasive False-Positive Identical-by-Descent Segments Detected by Large-Scale Pedigree Analysis" Mol. Bio. Evol. 31(8)(2014) pp. 2212-2222.
Durand, et al., "A scalable pipeline for local ancestry inference using tens of thousands of reference haplotypes" 23andMe, Inc., Oct. 7, 2020, pp. 1-14.
Durand, et al., "Ancestry Composition: A Novel, Efficient Pipeline for Ancestry Deconvolution" 23andMe White paper, Oct. 17, 2014, pp. 1-16.
Durbin, R., "Efficient haplotype matching and storage using the positional Burrows-Wheeler transform (PBWT)" Bioinformatics, Genetics and population analysis, vol. 30, No. 9, Jan. 9, 2014, pp. 1266-1272.
Feng et al., "Mining Multiple Temporal Patterns of Complex Dynamic Data Systems," Computational Intelligence and Data Mining, IEEE, 2009, 7 pages.
Finke, K. et al., "Ancestral Haplotype Reconstruction in Endogamous Populations Using Identity-By-Descent" PLOS Computational Biology, Feb. 26, 2021, vol. 17(2):e1008638, pp. 1-14.
Freyman, et al., "Fast and accurate identity-by-descent inference despite haplotype and phasing errors" Phase Aware IBD SMBE 2019 Abstract, 1 page.
Freyman, et al., "Fast and Robust Identity-by-Descent Inference with the Templated Positional Burrows-Wheeler Transform," Mol. Biol. Evol., Advance Access publication: Dec. 23, 2020, pp. 1-21.
Freyman, et al., "Phased IBD: fast and accurate identity-by-descent inference despite haplotype and phasing errors," 23andMe, ProbGen2019 (2019) pp. 1-1.
Freyman, W., "Methods to Infer the Genetic Ancestry of Millions of People," UC Berkeley, Aug. 22, 2019, pp. 1-65.
Fu, W. et al., "Robust Inference of Identity by Descent from Exome-Sequencing Data" The American Journal of Human Genetics 99, Nov. 3, 2016, pp. 1106-1116.
Fuchsberger, et al., "Minimac2: faster genotype imputation," Bioinformatics, vol. 31, No. 5, Oct. 22, 2014, pp. 782-784.
Gauvin, H. et al., "Genome-wide patterns of identity-by-descent sharing in the French Canadian founder population" European Journal of Human Genetics (2014) 22, pp. 814-821.
Goldberg, et al., "Autosomal Admixture Levels are Informative About Sex Bias in Admixed Populations," Genetics, Nov. 2014, vol. 198, pp. 1209-1229.
Gravel, et al., "Reconstructing Native American Migrations from Whole-Genome and Whole-Exome Data", PLOS Genetics, vol. 9, No. 12, Dec. 2013, e1004023 pp. 1-14.
Gravel, S., "Population Genetics Models of Local Ancestry," Genetics, Jun. 2012, 191(2), pp. 607-619.
Green, et al., "A Draft Sequence of the Neanderthal Genome," Science, vol. 328, May 7, 2010, pp. 710-722.
Gu et al., "Phenotypic Selection for Dormancy Introduced a Set of Adaptive Haplotypes from Weedy Into Cultivated Rice," Genetics Society of America, vol. 171, Oct. 2005, pp. 695-704.
Gusev, A. et al., "The Architecture of Long-Range Haplotypes Shared within and across Populations" Mol. Biol. Evol. 29(2) (2012) pp. 473-486.
Halder, Indrani, et al., "A Panel of Ancestry Informative Markers for Estimating Individual Biogeographical Ancestry and Admixture From Four Continents: Utility and Applications," Human Mutation, vol. 29, No. 5, 2008, pp. 648-658.
He, D. et al., "IPEDX: An Exact Algorithm for Pedigree Reconstruction Using Genotype Data," 2013 IEEE International Conference on Bioinformatics and Biomedicine, 2013, pp. 517-520.
He, et al., "Multiple Linear Regression for Index SNP Selection on Unphased Genotypes," Engineering in Medicine and Biology Society, EMBS Annual International Conference of the IEEE, Aug. 30-Sep. 3, 2006, pp. 5759-5762.
Hellenthal, et al. "A Genetic Atlas of Human Admixture History," Science, vol. 343, Feb. 14, 2014, pp. 747-751.
Henden L, et al., "IBD analysis of Australian amyotrophic lateral sclerosis SOD1-mutation carriers identifies five founder events and links sporadic cases to existing ALS families" bioRxiv. Jan. 1, 2019:685925 pp. 1-26.
Henn, et al., "Cryptic Distant Relatives Are Common in Both Isolated and Cosmopolitan Genetic Samples" PLOS One, 7(4):e34267, Apr. 2012, pp. 1-13.
Hill, et al. "Identification of Pedigree Relationship from Genome Sharing," G3: Gene | Genomes | Genetics, vol. 3, Sep. 2013, pp. 1553-1571.
Howie, et al., "Fast and accurate genotype imputation in genome-wide association studies through pre-phasing," Nature Genetics, vol. 44, No. 8, Aug. 2012, pp. 955-960.
Huff, C.D., et al., (2011) "Maximum-likelihood estimation of recent shared ancestry (ERSA)" Genome Research, 21, pp. 768-774.
Jaakkola, et al., "Exploiting generative models in discriminative classifiers" Advances in neural information processing systems, (1999) pp. 487-493.
Jia, Jing et al. "Developing a novel panel of genome-wide ancestry informative markers for bio-geographical ancestry estimates," Forensic Science International: Genetics, vol. 8 (2014) pp. 187-194.
Karakuzu, A., et al., "Assessment of In-Vivo Skeletal Muscle Mechanics During Joint Motion Using Multimodal Magnetic Resonance Imaging Based Approaches," Biomedical Engineering Meeting (BIYOMUT), 2014 18th National, pp. 1-4.
Kennedy, et al., "Visual Cleaning of Genotype Data," 2013 IEEE Symposium on Biological Data Visualization (BioVis), Atlanta, Ga., Oct. 2013, pp. 105-112.

(56) References Cited

OTHER PUBLICATIONS

Kerchner, [webpage] "DNAPrint Test Results—East Asian vs Native American Minority Admixture Detection," PA Deutsch Ethnic Group DNA Project, created Jun. 26, 2004, updated May 27, 2005, pp. 1-9. [retrieved May 23, 2018].
Kidd, et al. "Population Genetic Inference from Personal Genome Data: Impact of Ancestry and Admixture on Human Genomic Variation," The American Journal of Human Genetics, vol. 91, Oct. 5, 2012, pp. 660-671.
Kirkpatrick, B., et al. "Perfect Phylogeny Problems with Missing Values," IEEE/ACM Transactions on Computational Biology and Bioinformatics (TCBB), vol. 11, No. 5, Sep./Oct. 2014, pp. 928-941.
Cavalli-Sforza et al., The History and Geography of Human Genes, 1994, pp. 77-81, 90-93, 169-171.
Extended European Search Report, European Patent Application No. 20843426.6, mailed Jul. 7, 2023.
International HapMap Consortium "A second generation human haplotype map of over 3.1 million SNPs" Nature 449 (764) Oct. 18, 2007, pp. 851-861.
Khatri et al., Ontological Analysis of Gene Expression Data, 2005, Bioinformatics, vol. 21, No. 18 2005, pp. 3587-3595.
Notice of Allowance, U.S. Appl. No. 17/444,989, mailed Jul. 19, 2023.
Notice of Allowance, U.S. Appl. No. 18/180,691, mailed Sep. 1, 2023.
Office Action, U.S. Appl. No. 17/444,989, mailed Jun. 7, 2023.
Office Action, U.S. Appl. No. 17/662,040, mailed Jul. 10, 2023.
Office Action, U.S. Appl. No. 18/157,595, mailed Aug. 24, 2023.
Roach JC, et al., Analysis of genetic inheritance in a family quartet by whole-genome sequencing. Science. Apr. 30, 2010;328(5978):636-9. doi: 10.1126/science.1186802. Epub Mar. 10, 2010. PMID: 20220176; PMCID: PMC3037280.
Advisory Action, U.S. Appl. No. 15/950,023, mailed Nov. 23, 2022.
Fujimura, J. H., et al., Different Differences: The Use of 'genetic Ancestry' versus Race in Biomedical Human Genetic Research, Soc. Stud Sci. Feb. 2011 ; 41(1): 5-30.
International Search Report, PCT App. No. PCT/US2020/042628, mailed Dec. 29, 2020.
International Search Report, PCT App. No. PCT/US2021/045880, mailed Nov. 15, 2021.
Notice of Allowance, U.S. Appl. No. 13/800,683, mailed Jan. 20, 2016.
Notice of Allowance, U.S. Appl. No. 13/800,683, mailed May 3, 2016.
Notice of Allowance, U.S. Appl. No. 13/801,653, mailed Dec. 28, 2017.
Notice of Allowance, U.S. Appl. No. 15/181,083, mailed Aug. 14, 2018.
Notice of Allowance, U.S. Appl. No. 15/181,083, mailed Nov. 15, 2018.
Notice of Allowance, U.S. Appl. No. 15/181,088, mailed Feb. 26, 2020.
Notice of Allowance, U.S. Appl. No. 16/044,364, mailed Nov. 12, 2019.
Notice of Allowance, U.S. Appl. No. 16/446,465, mailed Apr. 2, 2020.
Notice of Allowance, U.S. Appl. No. 17/161,140, mailed Aug. 23, 2022.
Notice of Allowance, U.S. Appl. No. 17/682,761, mailed Aug. 10, 2022.
Office Action, U.S. Appl. No. 12/381,992, mailed Aug. 2, 2011.
Office Action, U.S. Appl. No. 12/381,992, mailed Dec. 20, 2011.
Office Action, U.S. Appl. No. 12/381,992, mailed Aug. 6, 2013.
Office Action, U.S. Appl. No. 12/381,992, mailed Dec. 27, 2013.
Office Action, U.S. Appl. No. 12/381,992, mailed Aug. 7, 2014.
Office Action, U.S. Appl. No. 12/381,992, mailed Dec. 22, 2014.
Office Action, U.S. Appl. No. 12/381,992, mailed May 22, 2015.
Office Action, U.S. Appl. No. 12/381,992, mailed Nov. 3, 2015.
Office Action, U.S. Appl. No. 12/381,992, mailed Mar. 16, 2016.
Office Action, U.S. Appl. No. 13/800,683, mailed Aug. 12, 2015.
Office Action, U.S. Appl. No. 13/801,653, mailed Sep. 30, 2015.
Office Action, U.S. Appl. No. 13/801,653, mailed May 31, 2016.
Office Action, U.S. Appl. No. 13/801,653, mailed Apr. 19, 2017.
Office Action, U.S. Appl. No. 15/181,083, mailed Jan. 23, 2018.
Office Action, U.S. Appl. No. 15/181,088, mailed Jun. 25, 2019.
Office Action, U.S. Appl. No. 15/267,053, mailed Sep. 26, 2018.
Office Action, U.S. Appl. No. 15/950,023, mailed Dec. 30, 2020.
Office Action, U.S. Appl. No. 15/950,023, mailed Jan. 5, 2022.
Office Action, U.S. Appl. No. 15/950,023, mailed Aug. 12, 2022.
Office Action, U.S. Appl. No. 16/044,364, mailed Feb. 11, 2019.
Office Action, U.S. Appl. No. 16/226,116, mailed Nov. 1, 2021.
Office Action, U.S. Appl. No. 16/282,221, mailed Feb. 4, 2022.
Office Action, U.S. Appl. No. 16/446,465, mailed Oct. 11, 2019.
Office Action, U.S. Appl. No. 16/844,758, mailed Oct. 5, 2020.
Office Action, U.S. Appl. No. 16/844,758, mailed Oct. 1, 2021.
Office Action, U.S. Appl. No. 17/161,140, mailed Jun. 3, 2021.
Office Action, U.S. Appl. No. 17/161,140, mailed Oct. 1, 2021.
Office Action, U.S. Appl. No. 17/161,140, mailed Apr. 15, 2022.
Office Action, U.S. Appl. No. 17/682,761, mailed Jun. 7, 2022.
Office Action, U.S. Appl. No. 17/707,790, mailed Dec. 15, 2022.
Phillips, C., Forensic Genetic Analysis of Bio-Geographical Ancestry, Forensic Science International: Genetics, pp. 49-65, 2015.
U.S. Appl. No. 13/800,683, filed Mar. 13, 2013.
U.S. Appl. No. 16/282,221, filed Feb. 21, 2019.
U.S. Appl. No. 16/844,758, filed Apr. 9, 2020.
U.S. Appl. No. 17/161,140, filed Jan. 28, 2021.
U.S. Appl. No. 17/682,761, filed Feb. 28, 2022.
Browning, Sharon R., and Brian L. Browning. "High-resolution detection of identity by descent in unrelated individuals", The American Journal of Human Genetics, 86.4 (2010).
CentiMorgan, ISOGG Wiki, Jul. 10, 2010 (date of initial version), https://isogg.org/wiki/CentiMorgan.
Notice of Allowance, U.S. Appl. No. 13/801,056, mailed May 18, 2015.
Notice of Allowance, U.S. Appl. No. 13/801,056, mailed Aug. 12, 2015.
Notice of Allowance, U.S. Appl. No. 13/801,386, mailed Jul. 24, 2017.
Notice of Allowance, U.S. Appl. No. 13/801,552, mailed Feb. 4, 2015.
Notice of Allowance, U.S. Appl. No. 13/801,552, mailed Jun. 26, 2015.
Notice of Allowance, U.S. Appl. No. 13/801,552, mailed Aug. 12, 2015.
Notice of Allowance, U.S. Appl. No. 14/938,111, mailed Apr. 29, 2019.
Notice of Allowance, U.S. Appl. No. 14/938,111, mailed Jan. 9, 2020.
Notice of Allowance, U.S. Appl. No. 18/058,029, mailed Feb. 7, 2023.
Office Action, U.S. Appl. No. 13/801,056, mailed Jan. 29, 2015.
Office Action, U.S. Appl. No. 13/801,386, mailed Jul. 8, 2015.
Office Action, U.S. Appl. No. 13/801,386, mailed Jan. 11, 2016.
Office Action, U.S. Appl. No. 13/801,386, mailed Oct. 27, 2016.
Office Action, U.S. Appl. No. 13/801,552, mailed Mar. 16, 2015.
Office Action, U.S. Appl. No. 14/924,552, mailed Feb. 9, 2018.
Office Action, U.S. Appl. No. 14/924,552, mailed Sep. 4, 2018.
Office Action, U.S. Appl. No. 14/924,562, mailed Jan. 30, 2018.
Office Action, U.S. Appl. No. 14/924,562, mailed Sep. 13, 2018.
Office Action, U.S. Appl. No. 14/924,562, mailed Jun. 5, 2019.
Office Action, U.S. Appl. No. 14/924,562, mailed Jan. 8, 2020.
Office Action, U.S. Appl. No. 14/938,111, mailed Sep. 25, 2018.
Office Action, U.S. Appl. No. 14/938,111, mailed Jun. 24, 2019.
Office Action, U.S. Appl. No. 15/950,023, mailed Jun. 29, 2021.
Office Action, U.S. Appl. No. 16/240,641, mailed Nov. 19, 2021.
Office Action, U.S. Appl. No. 16/844,758, mailed Feb. 2, 2021.
Office Action, U.S. Appl. No. 16/915,868, mailed Oct. 20, 2020.
Office Action, U.S. Appl. No. 16/915,868, mailed Feb. 10, 2021.
Office Action, U.S. Appl. No. 16/946,829, mailed Nov. 16, 2022.
Office Action, U.S. Appl. No. 17/249,520, mailed Jun. 1, 2021.
Office Action, U.S. Appl. No. 17/249,520, mailed Dec. 29, 2021.
Office Action, U.S. Appl. No. 17/249,520, mailed Nov. 23, 2022.

(56) References Cited

OTHER PUBLICATIONS

Office Action, U.S. Appl. No. 17/249,520, mailed Feb. 7, 2023.
Office Action, U.S. Appl. No. 17/387,940, mailed Jan. 24, 2022.
U.S. Appl. No. 12/381,992, filed Mar. 18, 2009.
U.S. Appl. No. 15/181,083, filed Jun. 13, 2016.
U.S. Appl. No. 15/181,088, filed Jun. 13, 2016.
U.S. Appl. No. 15/950,023, filed Apr. 10, 2018.
U.S. Appl. No. 16/044,364, filed Jul. 24, 2018.
U.S. Appl. No. 16/219,597, filed Dec. 13, 2018.
U.S. Appl. No. 16/226,116, filed Dec. 19, 2018.
U.S. Appl. No. 16/915,868, filed Jun. 29, 2020.
U.S. Appl. No. 16/946,829, filed Jul. 8, 2020.
U.S. Appl. No. 17/387,940, filed Jul. 28, 2021.
U.S. Appl. No. 17/443,946, filed Jul. 28, 2021.
U.S. Appl. No. 17/444,989, filed Aug. 12, 2021.
U.S. Appl. No. 17/662,040, filed May 4, 2022.
U.S. Appl. No. 17/707,790, filed Mar. 29, 2022.
Upton et al., Review: High-Performance computing to detect epistasis in genome scale data sets, 2016, Briefings in Bioinformatics, 17(30, p. 368-379 (2016).
Do et al., "A scalable pipeline for local ancestry inference using thousands of reference individuals (Abstract)," From Abstract/Session Information for Program No. 3386W; Session Title: Evolutionary and Population Genetics), ASHG, Aug. 2012.
Office Action, U.S. Appl. No. 16/844,758, mailed Apr. 11, 2022.
Office Action, U.S. Appl. No. 16/844,758, mailed Sep. 1, 2022.
Patterson, et al., "Methods for High-Density Admixture Mapping of Disease Genes," AJHG, vol. 74, No. 5, May 2004, pp. 1-33.
Patterson, et al., "Population Structure and Eigenanalysis," PLoS Genetics, vol. 2, No. 12, e190, Dec. 2006, pp. 2074-2093.
Phelps, C.I., et al. "Signal Classification by probablistic reasoning," Radio and Wireless Symposium (RWS), 2013 IEEE Year: 2013, pp. 154-156.
Phillips, et al., "Inferring Ancestral Origin Using a Single Multiplex Assay of Ancestry-Informative Marker SNPs," Forensic Science International, Genetics, vol. 1, 2007, pp. 273-280.
Pirola, et al., "A Fast and Practical Approach to Genotype Phasing and Imputation on a Pedigree with Erroneous and Incomplete Information," IEEE/ACM Transactions on Computational Biology and Bioinformatics, vol. 9, No. 6. Nov./Dec. 2012, pp. 1582-1594.
Pool, et al., "Inference of Historical Changes in Migration Rate From the Lengths of Migrant Tracts," Genetics, 181(2), Feb. 2009, pp. 711-719.
Price, et al. "Sensitive Detection of Chromosomal Segments of Distinct Ancestry in Admixed Populations," PLoS Genetics, vol. 5, No. 6, Jun. 19, 2009 (e1000519) pp. 1-18.
Price, et al., "New approaches to population stratification in genome-wide association studies" Nature Reviews Genetics, 11(7): Jun. 2010, pp. 459-463.
Ralph, et al., "The Geography of Recent Genetic Ancestry across Europe" PLoS Biol 11(5): e1001555, May 7, 2013, pp. 1-20.
Ramstetter, et al., "Benchmarking Relatedness Inference Methods with Genome-Wide Data from Thousands of Relatives", Genetics, vol. 207, Sep. 2017, pp. 75-82.
Ramstetter, et al., "Inferring Identical-by-Descent Sharing of Sample Ancestors Promotes High-Resolution Relative Detection" The American Journal of Human Genetics 103, Jul. 5, 2018, pp. 30-44.
Ratsch, et al., "Learning Interpretable SVMs for Biological Sequence Classification" BMC Bioinformatics, Mar. 20, 2006, 7(Suppl1):S9, pp. 1-14.
Reddit.com [Webpage] "Potential Incoming Algorithm Update (Ancestry Composition v5.9)_23andme" posted by u/ Spacemutantl4 (Aug. 12, 2020) pp. 1-7.
Royal, et al. "Inferring Genetic Ancestry: Opportunities, Challenges, and Implications," The American Journal of Human Genetics, vol. 86, May 14, 2010, pp. 661-673.
Sampson, et al., "Selecting SNPs to Identify Ancestry" Ann. Hum. Genet. 2011, 75(4) Jul. 2011, pp. 539-553.
Sankararaman, et al., "Estimating Local Ancestry in Admixed Populations," The American Journal of Human Genetics, vol. 82, Feb. 2008, pp. 290-303.
Sankararaman, et al., "On the inference of ancestries in admixed populations," Genome Research, Mar. 2008, vol. 18, pp. 668-675.
Seidman, et al., "Rapid, Phase-free Detection of Long Identity by-Descent Segments Enables Effective Relationship Classification" The American Journal of Human Genetics 106, Apr. 2, 2020, pp. 453-466.
Seldin, et al., "New approaches to disease mapping in admixed populations" Nature Reviews Genetics, 12(8): Aug. 2011, pp. 523-528.
Sengupta, et al., "Polarity and Temporality of High-Resolution Y-Chromosome Distributions in India Identify Both Indigenous and Exogenous Expansions and Reveal Minor Genetic Influence of Central Asian Pastoralists," The American Journal of Human Genetics, vol. 78, Feb. 2006, pp. 202-221.
Shemirani, et al., "Rapid detection of identity-by-descent tracts for mega-scale datasets" bioRxiv, Sep. 8, 2019, pp. 1-21.
Shriver, et al., "Ethnic-Affiliation Estimation by Use of Population-Specific DNA Markers," American Journal of Human Genetics, vol. 60, 1997, pp. 957-964.
Shriver, et al., "Genetic ancestry and the Search for Personalized Genetic Histories," Nature Reviews Genetics, vol. 5, Aug. 2004, pp. 611-618.
Shriver, M.D. et al., "The Genomic Distribution of Population Substructure in Four Populations Using 8,525 Autosomal SNPs", Human Genomics, 2004, vol. 1, No. 4, pp. 274-286.
Sohn, et al. "Robust Estimation of Local Genetic Ancestry in Admixed Populations Using a Nonparametric Bayesian Approach," Genetics, vol. 191, Aug. 2012, pp. 1295-1308.
Sundquist, et al., "Effect of genetic divergence in identifying ancestral origin using HAPAA" Genome Research, vol. 18, No. 4, Apr. 2008, pp. 676-682.
Tang, et al., "Reconstructing Genetic Ancestry Blocks in Admixed Individuals," The American Journal of Human Genetics, vol. 79, No. 1, Jul. 2006, pp. 1-12.
The 1000 Genomes Project Consortium "A global reference for human genetic variation" Nature, 526(7571); 2015, pp. 68-74.
Thiele, H., et al., HaploPainter: a tool for drawing Pedigrees with complex haplotypes, vol. 21 No. 8, 2005, pp. 1730-1732.
Thompson, E. "Identity by Descent Variation in Meiosis; Across Genomes, and in Populations" Genetics, vol. 194, Jun. 2013, pp. 301-326.
Thornton, et al., "Local and Global Ancestry Inference, and Applications to Genetic Association Analysis for Admixed Populations" Genet. Epidemiol., Sep. 2014, 38(01): S5-S12.
Uddin, et al., "Variability of Haplotype Phase and Its Effect on Genetic Analysis," Electrical and Computer Engineering, 2008, CCECE 2008, Canadian Conference on, IEEE, 2008, pp. 000596-000600.
Underhill, et al., "Use of Y Chromosome and Mitochondrial DNA Population Structure in Tracing Human Migrations," Annu. Rev. Genet., vol. 41, 2007, pp. 539-564.
Vacic, V. et al., "Genome-wide mapping of IBD segments in an Ashkenazi PD cohort identifies associated haplotypes", Human Molecular Genetics, 2014, vol. 23, No. 17 pp. 4693-4702.
Van Rossum, G., "Python reference manual" Computer Science/Department of Algorithmics and Architecture, CS-R9525, Apr. 10, 1995, version 1.2, pp. 1-59.
Van Rossum, G., "The Python Language Reference", Release 3.2.3, Python Software Foundation, Jun. 18, 2012, pp. 1-125.
Vanitha, et al., "Implementation of an Integrated FPGA Based Automatic Test Equipment and Test Generation for Digital Circuits," Information Communication and Embedded Systems (ICICES), 2013 International Conference on. IEEE, 2013.
Ward, J.J. et al., "Secondary Structure Prediction with Support Vector Machines", Bioinformatics, 2003, vol. 19, No. 13, pp. 1650-1655.
Williams, et al., "A rapid, accurate approach to inferring pedigrees in endogamous populations" bioRxiv, Jan. 29, 2020, pp. 1-27.
Yang, et al., "Examination of Ancestry and Ethnic Affiliation Using Highly Informative Diallelic DNA Markers: Application to Diverse

(56) References Cited

OTHER PUBLICATIONS and Admixed Populations and Implications for Clinical Epidemiology and Forensic Medicine," Human Genetics, vol. 118, 2005, pp. 382-392.
Yang, X. et al., "Identity-by-Descent Analysis Reveals Susceptibility Loci for Severe Acne in Chinese Han Cohort" Journal of Investigative Dermatology 139, Mar. 25, 2019, pp. 2049-2051. doi:10.1016/j.jid.2019.03.1132.
Yoon, Byung-Jun, "Hidden Markov Models and their Applications in Biological Sequence Analysis," Current Genomics, vol. 10, 2009, pp. 402-415.
Yousef, Malik, et al., "Recursive Cluster Elimination (RCE) for Classification and Feature Selection From Gene Expression Data," BMC Bioinformatics, vol. 8, May 2007, pp. 1-12.
Yu, Haiyuan et al., "Total Ancestry Measure: quantifying the similarity in tree-like classification, with genomic applications" Bioinformatics, vol. 23, No. 16, May 31, 2007, pp. 2163-2173.
Zheng, X. and Weir, B. "Eigenanalysis of SNP data with an identity by descent interpretation" Theoretical Population Biology 107 (2016) pp. 65-76.
Zhou, et al., "A Fast and Simple Method for Detecting Identity by-Descent Segments in Large-Scale Data" The American Journal of Human Genetics 106, Apr. 2, 2020, pp. 426-437.
Zhou, Nina, et al., "Effective Selection of Informative SNPs and Classification on the HapMap Genotype Data," BMC Bioinformatics, vol. 8, No. 1, 2007, pp. 1-9.
23andMeBlog [webpage] "New Feature: Ancestry Painting," by 23andMe, Ancestry, published online Mar. 25, 2008, pp. 1. [retrieved May 23, 2018] .
Akbani, R. et al., "Applying Support Vector Machines to Imbalanced Datasets", In Machine Learning: ECML 2004; Boulicaut, J.-F., Esposito, F., Giannotti, F., Pedreschi, D., Eds.; Lecture Notes in Computer Science; Springer Berlin Heidelberg: Berlin, Heidelberg, 2004; vol. 3201, pp. 39-50.
Alexander, et al., "Fast model-based estimation of ancestry in unrelated individuals", Genome Research 19, (2009) pp. 1655-1664.
Assareh, A., et al., "Interaction Trees: Optimizing Ensembles of Decision Trees for Gene-Gene Interaction Detections," 2012 11th International Conference on Machine Learning and Applications, vol. 1, Dec. 2012, pp. 616-621.
Ball, C. et al., "ancestryDNA—AncestryDNA Matching White Paper—Discovering genetic matches across a massive, expanding genetic database" AncestryDNA, Jul. 15, 2020, pp. 1-34.
Ball, C. et al., "ancestryDNA—DNA Circles White Paper—2014" AncestryDNA 2014, pp. 1-43.
Ball, C. et al., [Webpage] "ancestryDNA—Genetic Communities White Paper: Predicting fine-scale ancestral origins from the genetic sharing patterns among millions of individuals" Ancestry.com, Genetic Communities, pp. 1-28. [retrieved on Jan. 22, 2021].
Baran, Y. et al., "Fast and accurate inference of local ancestry in Latino populations", Bioinformatics, 2012, vol. 28, Issue 10, pp. 1359-1367.
Behnel, et al., "Cython: The Best of Both Worlds" Computing in Science and Engineering 13(2) May 2011, pp. 31-39.
Belbin, et al., "Genetic identification of a common collagen disease in Puerto Ricans via identity-by-descent mapping in a health system" eLife, Sep. 2017, 6:e25060, pp. 1-28.
Bercovici, et al., "Ancestry inference in complex admixtures via variablelength Markov chain linkage models" In Proceedings of the 16th Annual Conference on Research in Computational Molecular Biology (RECOMB 2012), pp. 12-28.
Bettinger, B., [webpage] "AncestryDNA Launches New Ethnicity Estimate," The Genetic Genealogist (Internet Blog), published online Sep. 12, 2013, pp. 1-4. [retrieved May 23, 2018].
Bettinger, B., [webpage] "AncestryDNA Officially Launches," The Genetic Genealogist (Internet Blog), published online May 3, 2012, pp. 1-2. [retrieved May 23, 2018].

Bettinger, B., [webpage] "The Monday Morning DNA Testing Company Review â€ AncestryByDNA," The Genetic Genealogist (Internet Blog), published Feb. 26, 2007, p. 1. [retrieved May 23, 2018].
Bohringer, S., et al., "A Software Package for Drawing Ideograms Automatically," Online J Bioinformatics, vol. 1, 2002, pp. 51-61.
Boser, et al., "A training algorithm for optimal margin classifiers" In Proceedings of the fifth annual workshop on computational learning theory, ACM, 1992, pp. 144-152.
Brion, M., et al., "Introduction of a Single Nucleodite Polymorphism—Based Major Y-Chromosome Haplogroup Typing Kit Suitable for Predicting the Geographical Origin of Male Lineages," Electrophoresis, vol. 26, 2005, pp. 4411-4420.
Brisbin, et al., "PCAdmix: principal components-based assignment of ancestry along each chromosome in individuals with admixed ancestry from two or more populations" Human Biology, vol. 84, No. 4 (2012) pp. 343-364.
Browning, Brian L., and Sharon R Browning, "Efficient multilocus association testing for whole genome association 42 studies using localized haplotype clustering", Genetic Epidemiology: The Official Publication of the International Genetic Epidemiology Society 31, No. 5 (2007): 365-375.
Browning, et al., "A Fast, Powerful Method for Detecting Identity by Descent", The American Journal of Human Genetics 88, Feb. 11, 2011, pp. 173-182.
Browning, et al., "Ancestry-specific recent effective population size in the Americas", PLoS Genet 14(5): e1007385, May 24, 2018, pp. 1-22.
Browning, et al., "Detecting Rare Variant Associations by Identity-by-Descent Mapping in Case-Control Studies", Genetics, vol. 190, Apr. 2012, pp. 1521-1531.
Browning, et al., "Identity by Descent Between Distant Relatives: Detection and Applications", Annu. Rev. Genet., Sep. 17, 2012, 46:617-33.
Browning, et al., "Improving the Accuracy and Efficiency of Identity-by-Descent Detection in Population Data", Genetics, vol. 194, Jun. 2013, pp. 459-471.
Browning, S.R., et al., "Haplotype phasing: existing methods and new developments," Nature Reviews | Genetics, vol. 12, Oct. 2011, pp. 703-714. [URL: http://www.nature.com/reviews/genetics].
Browning, Sharon R, and Brian L. Browning,"Rapid and accurate haplotype phasing and missing-data inference for whole-genome association studies by use of localized haplotype clustering," The American Journal of Human Genetics, No. 5 (2007): 1084-1097.
Bryc, et al., "The Genetic Ancestry of African Americans, Latinos, and European Americans across the United States," The American Journal of Human Genetics, vol. 96, Jan. 8, 2015, pp. 37-53.
Burroughs et al., "Analysis of Distributed Intrusion Detection Systems Using Bayesian Methods," Performance, Computing and Communications Conference, 2002, 21st IEEE International. IEEE, 2002, pp. 329-334.
Bycroft, et al., "The UK Biobank resource with deep phenotyping and genomic data", Nature, 562(7726), pp. 203-209, Oct. 2018. ISSN 1476-4687.
Byrne, J. et al., "The simulation life-cycle: supporting the data collection and representation phase," Simulation Conference (WSC), 2014 Wincer, pp. 2738-2749.
Cann, et al., "A human genome diversity cell line panel" Science, 296(5566), Apr. 12, 2002, vol. 296 No. 5566, pp. 261-262.
Cao, et al., "Design of Reliable System Based on Dynamic Bayesian Networks and Genetic Algorithm," Reliability and Maintainability Symposium (RAMS), 2012 Proceedings—Annual. IEEE, 2012.
Cavalli-Sforza, L., "The Human Genome Diversity Project: past, present and future," Nature Reviews, Genetics, vol. 6, Apr. 2005, pp. 333-340.
Crawford, et al., "Evidence for substantial fine-scale variation in recombination rates across the human genome," Nature Genetics, vol. 36, No. 7, Jul. 2004, pp. 700-706.
Falush, et al., "Inference of population structure using multilocus genotype data:linked loci and correlated allele frequencies" Genetics 164, (2003) pp. 1567-1587.
Gusev, et al., "Whole population, genome-wide mapping of hidden relatedness," Genome Research, vol. 19, 2009, pp. 318-326.

(56) References Cited

OTHER PUBLICATIONS

Howie, et al., "A Flexible and Accurate Genotype Imputation Method for the Next Generation of Genome-Wide Association Studies," PLoS Genetics, vol. 5, No. 6, Jun. 2009, pp. 1-15.
Ma, et al., "PatternHunter: faster and more sensitive homology search" Bioinformatics, vol. 18, No. 3 (2002) pp. 440-445.
Porras-Hurtado, et al., "An overview of Structure: applications, parameter settings, and supporting software," Frontiers in Genetics, vol. 4, No. 96, May 29, 2013, pp. 1-13.
Pritchard, et al., "Association Mapping in Structured Populations," Am. J. Hum. Genet., vol. 67, 2000, pp. 170-181.
Pritchard, et al., "Inference of population structure using multilocus genotype data" Genetics 155, (2000) pp. 945-959.
Purcell, et al., "Plink: a toolset for whole-genome association and population-based linkage analysis", Am. J. Hum. Genet., vol. 81, Sep. 2007, pp. 559-575.
Rabiner, L., "A Tutorial on Hidden Markov Models and Selected Applications in Speech Recognition," Proceedings of the IEEE, vol. 77, No. 2, Feb. 1989, pp. 257-286.
Scheet, et al., "A Fast and Flexible Statistical Model for Large-Scale Population Genotype Data: Applications to Inferring Missing Genotypes and Haplotypic Phase," The American Journal of Human Genetics, vol. 78, Apr. 2006, pp. 629-644.
Stephens, et al., "A Comparison of Bayesian Methods for Haplotype Reconstruction from Population Genotype Data," Am. J. Hum. Genet., vol. 73, 2003, pp. 1162-1169.
Stephens, et al., "A New Statistical Method for Haplotype Reconstruction from Population Data," Am. J. Hum. Genet., vol. 68, 2001, pp. 978-989.
Stephens, et al., "Accounting for Decay of Linkage Disequilibrium in Haplotype Inference and Missing-Data Imputation," Am. J. Hum. Genet., vol. 76, 2005, pp. 449-462.
Tang, Hua, et al., "Estimation of Individual Admixture: Analytical and Study Design Considerations", Genetic Epidemiology 28: 289-301 (2005).
The International HapMap Consortium, "A haplotype map of the human genome" vol. 437, Oct. 27, 2005, pp. 1300-1320. doi:10.1038/nature04226.
The International HapMap Consortium, "A second generation human haplotype map of over 3.1 million SNPs," Nature, vol. 449, Oct. 18, 2007, pp. 851-860. <doi: 10.1038/nature06258>.
Office Action, U.S. Appl. No. 16/947,107, mailed Mar. 13, 2023.
Office Action, U.S. Appl. No. 16/947,107, mailed Aug. 17, 2023.
Office Action, U.S. Appl. No. 18/157,595, mailed May 1, 2023.
Kraak, M-J, "Visualising Spatial Distributions," Geographical Information Systems: Principles, Techniques, Applications and Management, New York, John Wiley and Sons, 1999, pp. 157-173.
Kumar, et al., "XGMix: Local-Ancestry Inference with Stacked XGBoost" bioRxiv, Apr. 21, 2020, 053876, pp. 1-8.
Lafferty, et al., "Conditional random fields: Probabilistic models for segmenting and labeling sequence data" Proceedings of the 18th International Conference on Machine Learning (ICML-2001), Jun. 28, 2001, pp. 1-10.
Lawson, et al., "Inference of Population Structure using Dense Haplotype Data," PLoS Genetics, vol. 8, No. 1, Jan. 2012, pp. 1-16.
Lazaridis et al., "Ancient Human Genomes Suggest Three Ancestral Populations for Present-Day Europeans," Nature, vol. 513, Sep. 18, 2014, doi:10.1038/nature 13673, pp. 409-413.
Lee, et al., "Comparing genetic ancestry and self-reported race/ethnicity in a multiethnic population in New York City," Journal of Genetics, vol. 89, No. 4, Dec. 2010, pp. 417-423.
Lei, X. et al., "Cloud-Assisted Privacy-Preserving Genetic Paternity Test," 2015 IEEE/CIC International Conference on Communications in China (ICCC), Apr. 7, 2016, pp. 1-6.
Li, et al. "Worldwide Human Relationships Inferred from Genome-Wide Patterns of Variation," Science, vol. 319, Feb. 22, 2008, pp. 1100-1104.
Li, et al., "Mapping short DNA sequencing reads and calling variants using mapping quality scores," Genome Research, Aug. 19, 2008, pp. 1851-1858.
Li, et al., "Modeling linkage disequilibrium and identifying recombination hotspots using single-nucleotide polymorphism data" Genetics 165, (2003) pp. 2213-2233.
Li, H., et al., "Relationship Estimation from Whole-Genome Sequence Data" PLoS Genet 10(1); (2014) e1004144.
Li, X., et al., "Integrating Phenotype-Genotype Data for Prioritization of Candidate Symptom Genes," 2013 IEEE International Conference on Bioinformatics and Biomedicine, Dec. 2013, pp. 279-280.
Liang et al., "A Deterministic Sequential Monte Carlo Method for Haplotype Inference," IEEE Journal of Selected Topics in Signal Processing, vol. 2, No. 3, Jun. 2008, pp. 322-331.
Liang et al., "The Lengths of Admixture Tracts," Genetics, vol. 197, Jul. 2014, pp. 953-967.
Lin et al. "Polyphase Speech Recognition," Acoustics, Speech and Signal Processing, IEEE International Conference on 2008, IEEE, 2008, 4 pages.
Lin, et al., "Identity-by-Descent Mapping to Detect Rare Variants Conferring Susceptibility to Multiple Sclerosis" PLoS One 8(3), Mar. 5, 2013, e56379, pp. 1-8. doi:10.1371/journal.pone.0056379.
Lipson, et al., "Reconstructing Austronesian population history in Island Southeast Asia," Nature Communications, 5:4689, DOI: 10.1038 /ncomms5689, 2014, pp. 1-7.
Loh, et al., "Fast and accurate long-range phasing in a UK Biobank cohort" Nature Genetics, vol. 48, No. 7, Jul. 2016, pp. 811-817.
Loh, et al., "Inferring Admixture Histories of Human Populations Using Linkage Disequilibrium," Genetics, 193(4), Apr. 2013, pp. 1233-1254.
Loh, et al., "Reference-based phasing using the Haplotype Reference Consortium panel" Nat. Genet. Nov. 2016; 48(11): pp. 1443-1448.
Lunter, G., "Fast haplotype matching in very large cohorts using the Li and Stephens model" bioRxiv, Apr. 12, 2016, pp. 1-19.
Lunter, G., "Haplotype matching in large cohorts using the Li and Stephens model" Bioinformatics, Aug. 25, 2018, pp. 1-9.
Mahieu, L., [webpage] "My (free) Ancestry.com DNA results—a comparison to FamilyTreeDNA," Genejourneys (Internet Blog), published online Mar. 6, 2012, pp. 1-3. [retrieved May 23, 2018].
Maples, et al. "RFMix: A Discriminitve Modeling Approach for Rapid and Robust Local-Ancestry Inference," American Journal of Human Genetics (AJHG) vol. 93, No. 2, Aug. 8, 2013, pp. 278-288. [retrieved Nov. 12, 2015].
Martin, et al., "Haplotype Sharing Provides Insights into Fine-Scale Population History and Disease in Finland", The American Journal of Human Genetics 102, May 3, 2018, pp. 760-775.
McCarthy, et al., "A reference panel of 64,976 haplotypes for genotype imputation" Nature genetics, 48(10), Oct. 2016, pp. 1279-1283.
McInnes, et al., "UMAP: Uniform Manifold Approximation and Projection for Dimension Reduction" arXiv preprint arXiv:1802.03426 (2018), pp. 1-63.
Mersha, Tesfaye et al. "Self-reported race/ethnicity in the age of genomic research: its potential impact on understanding health disparities," Human Genomics, vol. 9, No. 1 (2015) pp. 1-15.
Montinaro, Francesco et al. "Unraveling the hidden ancestry of American admixed populations," Nature Communications, Mar. 24, 2015, pp. 1-7.
Montserrat, et al., "LAI-Net: Local-ancestry inference with neural networks" ICASSP 2020-2020 IEEE International Conference on Acoustics, Speech and Signal Processing (ICASSP), May 2020, pp. 1314-1318.
Moore, C., [webpage] "LivingSocial's AncestrybyDNA Offer is Not the AncestryDNA Test!" Your Genetic Genealogist (Internet Blog), published online Sep. 18, 2012, pp. 1-2. [retrieved May 23, 2018].
Moore, C., [webpage] "New Information on Ancestry.com's AncestryDNA Product," Your Genetic Genealogist (Internet Blog), published online Mar. 30, 2012, pp. 1-3. [retrieved May 23, 2018].
Moreno-Estrada, et al., "Reconstructing the Population Genetic History of the Caribbean," PLoS Genetics, 9(11), e1003925, Nov. 14, 2013, pp. 1-19.
Moreno-Estrada, et al., "The Genetics of Mexico Recapitulates Native American Substructure and Affects Biomedical Traits" Science, Jun. 13, 2014, 344(6189), pp. 1280-1285.

(56) References Cited

OTHER PUBLICATIONS

Naseri, et al., "Efficient Haplotype matching between a query and panel for genealogical search", Bioinformatics, 35, 2019, pp. i233-i241. <doi: 10.1093/bioinformatics/btz347>.

Naseri, et al., "Personalized genealogical history inferred from biobank-scale IBD segments" bioRxiv, Dec. 20, 2019, pp. 1-27.

Naseri, et al., "RaPID: ultra-fast, powerful, and accurate detection of segments identical by descent (IBD) in biobank-scale cohorts" Genome Biology, 201:143 (2019) pp. 1-15.

Naseri, et al., "Ultra-fast Identity by Descent Detection in Biobank-Scale Cohorts using Positional Burrows-Wheeler Transform" bioRxiv, Jan. 26, 2017, pp. 1-13.

Ng, et al., "On discriminative vs. generative classifiers: A comparison of logistic regression and naive Bayes" Advances in neural information processing systems, 14:841, 2002.

Nievergeit, Caroline, et al., "Inference of human continental origin and admixture proportions using a highly discriminative ancestry informative 41-SNP panel," Investigative Genetics, vol. 4, No. 13 (2013), pp. 1-16.

Novembre, et al. "Recent advances in the study of fine-scale population structure in humans," Current Opinion in Genetics & Development, vol. 41 (2016), pp. 98-105.

Novembre, et al., "Perspectives on human population structure at the cusp of the sequencing era" Annual Review of Genomics and Human Genetics, 12(1); 2011, pp. 245-274.

O'Dushlaine, C. et al. "Genes Predict Village of Origin in Rural Europe", European Journal of Human Genetics 2010, vol. 18, No. 11, pp. 1269-1270.

Omberg, L., et al., "Inferring Genome-Wide Patterns of Admixture in Qataris Using Fifty-Five Ancestral Populations," BMC Genetics, 2012, ISSN 1471-2156, BioMed Central, Ltd., 18 pages.

Padhukasahasram, B., "Inferring ancestry from population genomic data and its applications" Front. Genet. Jul. 2014, vol. 5, Article 204, pp.

Palamara, et al., "Inference of historical migration rates via haplotype sharing" Bioinformatics, vol. 29 (2013) pp. i180-i188.

Palamara, et al., "Length Distributions of Identity by Descent Reveal Fine-Scale Demographic History" The American Journal of Human Genetics 91, Nov. 2, 2012, pp. 809-822.

Pasaniuc et al., "Highly Scalable Genotype Phasing By Entropy Minimization," Engineering in Medicine and Biology Society, 2006, EMBS'06, 28th Annual International Conference of the IEEE, 2006, 5 pages.

Pasaniuc, et al., "Inference of locus-specific ancestry in closely related populations," Bioinformatics, 25(12) Jun. 2009, pp. i213-i221.

Pathak, et al., "The Genetic Ancestry of Modern Indus Valley Populations from Northwest India" The American Journal of Human Genetics 103, Dec. 6, 2018, pp. 918-929.

Extended European Search Report, European Patent Application No. 21856763.4, mailed Nov. 16, 2023.

Office Action, U.S. Appl. No. 18/157,595, mailed Jan. 2, 2024.

Stasko et al., Focus+Context Display and Navigation Techniques for Enhancing Radial, Space-Filling Hierarchy Visualizations, Proc. of the IEEE Symposium on Information Visualization, Feb. 2000.

\* cited by examiner

FIG. 4

```
for i = 0 to t - 1 do
    for j = 0 to M - 1 do
        ppa_ij ← j                                      // initialize positional prefix array
        div_ij ← 0                                      // initialize divergence array
    end for
end for
for k = 0 to N - 1 do                                   // loop over all sites
    for i = 0 to t - 1 do                               // loop over all templates
        if T(i,k) == 1 then                             // templating function
            s_0 ← 0, s_1 ← 0
            create empty arrays m_0, m_1, p_0, p_1, d_0, d_1
            for j = 0 to M - 1 do                       // loop over all haplotypes
                if length (m_0) > 0 and length (m_1) > 0 then
                    update match between ppa_{i,m_0} and ppa_{i,m_1} in P_s and P_e
                end if
            end if
            empty arrays m_0, m_1
            if div_{i,k} > s_0 then
                s_0 ← div_{i,k}
            end if
            if div_{i,k} > s_1 then
                s_1 ← div_{i,k}
            end if
            if A_{j,k} == ? then                        // check for missing data
                A_{j,k} = A_{j-1,k} or A_{j+1,k}        // extend the current longest match
            end if
            if A_{j,k} == 0 then                        // check allele at site k for haplotype ppa_{i,j}
                p_0 = ppa_{i,j}
                d_0 = s_0
                m_0 = append j
                s_0 = 0
            end if
            if A_{j,k} == 1 then
                p_1 = ppa_{i,j}
                d_1 = s_1
                m_1 = append j
                s_1 = 0
            end if
        end for
        if div_ij > k - L_m then                        // check for matches with last haplotype
            if length(m_0) > 0 and length(m_1) > 0 then
                update match between ppa_{i,m} and ppa_{i,m} in P_s and P_e
            end if
        end if
        ppa_{i,k+1} concatenate p_0 and p_1
        div_{i,k+1} concatenate d_0 and d_1             // assemble ppa and div for k+1
        end if
    end for
end for
```

FIG. 5C

$$Q_\alpha = \begin{bmatrix}
0000 & - & \alpha_s & \alpha_s & \alpha_s & \alpha_s & \alpha_s^2 & \alpha_s^2 & \alpha_s^2 & \alpha_s^2 \\
0101 & \alpha_e & - & \alpha_s\alpha_e & \alpha_s\alpha_e & \alpha_s & \alpha_s & \alpha_s^2\alpha_e & \alpha_s^2\alpha_e & \alpha_s^2\alpha_e \\
1001 & \alpha_e & \alpha_s\alpha_e & - & \alpha_s\alpha_e & \alpha_s\alpha_e & \alpha_s^2\alpha_e & \alpha_s & \alpha_s^2\alpha_e & \alpha_s^2\alpha_e \\
0110 & \alpha_e & \alpha_s\alpha_e & \alpha_s\alpha_e & - & \alpha_s\alpha_e & \alpha_s^2\alpha_e & \alpha_s^2\alpha_e & \alpha_s & \alpha_s^2\alpha_e \\
1001 & \alpha_e & \alpha_s\alpha_e & \alpha_s\alpha_e & \alpha_s\alpha_e & - & \alpha_s^2\alpha_e & \alpha_s^2\alpha_e & \alpha_s^2\alpha_e & \alpha_s \\
1212 & \alpha_e^2 & \alpha_s\alpha_e^2 & \alpha_s^2\alpha_e^2 & \alpha_s^2\alpha_e^2 & \alpha_s^2\alpha_e^2 & - & \alpha_s^2\alpha_e^2 & \alpha_s^2\alpha_e^2 & \alpha_s^2\alpha_e^2 \\
2112 & \alpha_e^2 & \alpha_s^2\alpha_e^2 & \alpha_e & \alpha_s^2\alpha_e^2 & \alpha_s^2\alpha_e^2 & \alpha_s^2\alpha_e^2 & - & \alpha_s^2\alpha_e^2 & \alpha_s^2\alpha_e^2 \\
1221 & \alpha_e^2 & \alpha_s^2\alpha_e^2 & \alpha_s^2\alpha_e^2 & \alpha_e & \alpha_s^2\alpha_e^2 & \alpha_s^2\alpha_e^2 & \alpha_s^2\alpha_e^2 & - & \alpha_s^2\alpha_e^2 \\
2121 & \alpha_e^2 & \alpha_s\alpha_e^2 & \alpha_s\alpha_e^2 & \alpha_s\alpha_e^2 & \alpha_e & \alpha_s^2\alpha_e^2 & \alpha_s^2\alpha_e^2 & \alpha_s^2\alpha_e^2 & - \\
\end{bmatrix}$$

FIG. 9B

| IBD Analysis Type | Chromosomes | Number of Samples | Steps Performed | Memory Required (per core) | CPU Cores | CPU Time (minutes) | Wall Clock Time (minutes) |
|---|---|---|---|---|---|---|---|
| In-sample | 1 | 1M | 1) In-sample IBD compute and TPBWT compression for 20 batches of 50k samples | 80 Gb | 20 | 206.4 | 10.3 |
| | | | 2) Out-of-sample comparisons among all compressed batches | 80 Gb | 190 | 2527.0 | 13.3 |
| | | | Total | | | 2733.4 | 23.6 |
| Out-of-sample | 1 | 10k against 1M | 1) TPBWT- compression of 10k samples | 3.2 Gb | 1 | 1.1 | 1.1 |
| | | | 2) Compare compressed 10k to each compressed 50k batch | 16.0 Gb | 20 | 114.0 | 5.7 |
| | | | Total | | | 115.1 | 6.8 |
| In-sample | 1-22, X | 1M | 1) In-sample IBD compute and TPBWT compression for 20 batches of 50k samples | 80 Gb | 460 | 2889.6 | 10.3 |
| | | | 2) Out-of-sample comparisons among all compressed batches | 80 Gb | 920 | 35378.0 | 38.5 |
| | | | Total | | | 38267.6 | 48.8 |
| Out-of-sample | 1-22, X | 10k against 1M | 1) TPBWT- compression of 10k samples | 3.2 Gb | 23 | 15.4 | 1.1 |
| | | | 2) Compare compressed 10k to each compressed 50k batch | 16.0 Gb | 460 | 1596.0 | 5.7 |
| | | | Total | | | 1611.4 | 6.8 |
| Out-of-sample | 1-22, X | 10k against 10M | 1) TPBWT- compression of 10k samples | 3.2 Gb | 23 | 15.4 | 1.1 |
| | | | 2) Compare compressed 10k to each compressed 50k batch | 16.0 Gb | 920 | 15960.0 | 17.3 |
| | | | Total | | | 15975.4 | 18.4 |

FIG. 20B

IDENTITY-BY-DESCENT RELATEDNESS BASED ON FOCAL AND REFERENCE SEGMENTS

CROSS-REFERENCE TO RELATED APPLICATIONS

The present application is a continuation application claiming priority to Non-Provisional patent application Ser. No. 16/947,107, filed Jul. 17, 2020: which claims the benefit of Provisional Patent Application No. 62/876,497, filed Jul. 19, 2019. The contents of Non-Provisional patent application Ser. No. 16/947,107 and Provisional Patent Application No. 62/876,497 are hereby incorporated by reference in their entireties.

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND

Modern genetic data sets already number in the millions of genomes and are growing rapidly. Inferring the genomic location and length of identical-by-descent (IBD) segments among the related individuals in these data sets is a central step in many genetic analyses.

IBD estimates can best be exploited when they are made using phased haplotypes; this means each individual in the data set is represented by two sequences each of which consists of alleles co-located on the same chromosome and inherited from a different parent. IBD estimates that are phase aware can improve relationship and pedigree inference, allow health and trait inheritance to be traced, and make possible a range of other inferences regarding demographic history and ancestry that are not possible when IBD estimates are made using only unphased genotype data. Therefore, methods and systems that can improve performance of phase aware IBD estimates have significant value.

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

SUMMARY

The disclosed implementations concern methods, apparatus, systems, and computer program products for processing haplotype data to accurately estimate IBD segments between individuals.

A first aspect of the disclosure provides computer-implemented methods for estimating IBD segments between individuals.

Another aspect of the disclosure provides systems for estimating IBD segments. In some implementations, the system involves: a sequencer for sequencing nucleic acids of the test sample; a processor; and one or more computer-readable storage media having stored thereon instructions for execution on said processor to estimate IBD segments between individuals.

Another aspect of the disclosure provides a computer program product including a non-transitory machine readable medium storing program code that, when executed by one or more processors of a computer system, causes the computer system to implement the methods above for estimating IBD segments.

A computer implemented method of processing haplotypes to reduce genotyping errors when determining identity by descent (IBD) segments between haplotypes is provided, the method including: providing a first digital template including a first arrangement of masked and unmasked sites in a window of consecutive haplotype sites; providing a second digital template including a second arrangement of masked and unmasked sites in a window of consecutive haplotype sites, wherein the first and second arrangements are different; providing two or more haplotypes strings for identification of IBD segments therebetween, each of the two or more haplotype strings representing a sequence of allele values at polymorphic sites in a haplotype of an organism; and computationally identifying IBD segments between the two or more haplotype strings by (i) identifying first matches among alleles of the haplotype strings at unmasked sites produced by applying the first digital template to the two or more haplotype strings, (ii) identifying second matches among alleles of the haplotype at unmasked sites produced by applying the second digital template to the two or more haplotype strings, and (iii) merging the first and second matches among alleles to produce a merged set of IBD segments, wherein the merged set of IBD segments has reduced impact from genotyping errors compared to a set of IBD segments generated without applying the first and second digital templates.

In some embodiments, the first and second templates each have a size of at least four consecutive haplotype sites. In some embodiments, identifying the first matches among alleles at unmasked sites includes sequentially applying the first digital template to the two or more haplotype strings, each time moving to a next sequential section of the two or more haplotype strings. In some embodiments, computationally identifying IBD segments between the two or more haplotype strings further includes: computationally identifying additional matches among alleles at unmasked sites produced by applying one or more additional digital templates to the two or more haplotype strings, wherein the one or more additional digital templates have additional arrangements of masked and unmasked sites in windows of consecutive haplotype sites, and each of the additional arrangements is different from both the first and the second arrangements, and wherein merging the first and second matches among alleles to produce a merged set of IBD segments further includes computationally merging the additional matches with the first and second matches to produce the merged set of IBD segments. In some embodiments, computationally identifying additional matches among alleles at unmasked sites employs a third digital template, a fourth digital template, a fifth digital template, and a sixth digital template. In some embodiments, the first through sixth digital templates each include two masked sites and two unmasked sites. In some embodiments, the first digital template and the second digital template each have a ratio of masked sites to unmasked sites of between about 2:1 to about 1:2.

In some embodiments, the two or more haplotype strings include at least one thousand haplotype strings. In some embodiments, the two or more haplotype strings include at least one million haplotype strings. In some embodiments, computationally identifying IBD segments between the two or more haplotype strings includes performing a positional Burrows-Wheeler transform (PBWT) on the unmasked sites produced by applying the first and second templates to the two or more haplotype strings. In some embodiments, computationally merging the first and second matches among alleles is performed while considering individual polymorphic sites of the two or more haplotype strings using the PBWT. In some embodiments, the total number of digital templates is between 2 and k, where k is the number of haplotype sites in the window. In some embodiments, the total number of digital templates is k!/(m! *(k-m)!), where k is the number of haplotype sites in the window and m is the number of masked sites in the window. In some embodiments, applying the first digital template comprises a deterministic process employing the first arrangement of masked and unmasked sites.

In another aspect of the embodiments provided herein, a system for processing haplotypes to reduce genotyping errors when determining identity by descent (IBD) segments between haplotypes is provided, the system including: (a) one or more processors and associated memory; (b) computer readable instructions for: providing a first digital template including a first arrangement of masked and unmasked sites in a window of consecutive haplotype sites; providing a second digital template including a second arrangement of masked and unmasked sites in a window of consecutive haplotype sites, wherein the first and second arrangements are different; providing two or more haplotypes strings for identification of IBD segments therebetween, each of the two or more haplotype strings representing a sequence of allele values at polymorphic sites in a haplotype of an organism; and identifying IBD segments between the two or more haplotype strings by (i) identifying first matches among alleles of the haplotype strings at unmasked sites produced by applying the first digital template to the two or more haplotype strings, (ii) identifying second matches among alleles of the haplotype at unmasked sites produced by applying the second digital template to the two or more haplotype strings, and (iii) merging the first and second matches among alleles to produce a merged set of IBD segments, wherein the merged set of IBD segments has reduced impact from genotyping errors compared to a set of IBD segments generated without applying the first and second digital templates.

In some embodiments, the first and second templates each have a size of at least four consecutive haplotype sites. In some embodiments, the instructions for identifying the first matches among alleles at unmasked sites includes instructions for sequentially applying the first digital template to the two or more haplotype strings, each time moving to a next sequential section of the two or more haplotype strings. In some embodiments, the instructions for identifying IBD segments between the two or more haplotype strings further include instructions for: computationally identifying additional matches among alleles at unmasked sites produced by applying one or more additional digital templates to the two or more haplotype strings, wherein the one or more additional digital templates have additional arrangements of masked and unmasked sites in windows of consecutive haplotype sites, and each of the additional arrangements is different from both the first and the second arrangements, and wherein merging the first and second matches among alleles to produce a merged set of IBD segments further includes computationally merging the additional matches with the first and second matches to produce the merged set of IBD segments. In some embodiments, the instructions for identifying additional matches among alleles at unmasked sites employ a third digital template, a fourth digital template, a fifth digital template, and a sixth digital template. In some embodiments, the first through sixth digital templates each include two masked sites and two unmasked sites. In some embodiments, the first digital template and the second digital template each have a ratio of masked sites to unmasked sites of between about 2:1 to about 1:2.

In some embodiments, the two or more haplotype strings include at least one thousand haplotype strings. In some embodiments, the two or more haplotype strings include at least one million haplotype strings. In some embodiments, the instructions for identifying IBD segments between the two or more haplotype strings include instructions performing a positional Burrows-Wheeler transform (PBWT) on the unmasked sites produced by applying the first and second templates to the two or more haplotype strings. In some embodiments, the instructions for merging the first and second matches among alleles include instructions for performing the merging while considering individual polymorphic sites of the two or more haplotype strings using the PBWT. In some embodiments, the total number of digital templates is between 2 and k, where k is the number of haplotype sites in the window. In some embodiments, the total number of digital templates is k!/(m! *(k-m)!), where k is the number of haplotype sites in the window and m is the number of masked sites in the window.

In another aspect of the embodiments herein, a method of identifying IBD segments between two or more haplotypes strings, each of the two or more haplotype strings representing a sequence of allele values at polymorphic sites in a haplotype of an organism is provided, the method including: (a) computationally identifying IBD segments between the two or more haplotype strings by (i) identifying first matches among alleles of two or more haplotype strings at unmasked sites produced by applying a first digital template to the two or more haplotype strings, (ii) identifying second matches among alleles of the haplotype at unmasked sites produced by applying a second digital template to the two or more haplotype strings, and (iii) merging the first and second matches among alleles to produce a merged set of IBD segments, wherein the first digital template includes a first arrangement of masked and unmasked sites in a window of consecutive haplotype sites, wherein the second digital template includes a second arrangement of masked and unmasked sites in the window of consecutive haplotype sites, and wherein the first and second arrangements are different; and (b) identifying a potential phase switch error in at least one of the two or more haplotype strings; and (c) correcting the phase switch error. In some embodiments, identifying the potential phase switch error includes identifying proximate IBD segments in at least one pair of the two or more haplotype strings.

In another aspect of the embodiments herein, a computer implemented method of determining identity by descent (IBD) segments is provided, the method including: determining first potential IBD segments among phased haplotype data for a plurality of individuals, wherein the first potential IBD segments have an end site; determining second potential IBD segments among haplotype data for the plurality of individuals, wherein the second potential IBD segments have a start site; determining that the end site of the first potential IBD segments and the start site of the second potential IBD segments are within a threshold number of sites of each other; and merging the first potential IBD segments and the second potential IBD segments to form a combined potential IBD segment.

In some embodiments, the first potential IBD segments and the second potential IBD segments are on different haplotypes for an individual of the plurality of individuals, and the method further includes: determining a phase switch error occurred at a site between the first potential IBD segment and the second potential IBD segment for the individual; and swapping the haplotypes for the individual from the position of the phase switch error. In some embodiments, the first potential IBD segments and the second potential IBD segments overlap for an individual of the plurality of individuals. In some embodiments, the first potential IBD segment and the second potential IBD segment each span at least the threshold number of sites. In some embodiments, the threshold number of sites is between about 0 and 500 SNPs. In some embodiments, the plurality of individuals do not share a parent-child relationship.

In some embodiments, the method further includes: determining a third potential IBD segments among phased haplotype data for a plurality of individuals, wherein the third potential IBD segments have a start site; determining that the end site of the combined potential IBD segments and the start site of the third potential IBD segments are within the threshold number of SNPs of each other; and merging the combined potential IBD segments and the third potential IBD segments. In some embodiments, the combined potential IBD segments and the third potential IBD segments are on different haplotypes for an individual of the plurality of individuals, and the method further includes: determining a phase switch error occurred at a site between the combined potential IBD segment and the third potential IBD segment for the individual; and swapping the haplotypes for the individual from the position of the phase switch error. In some embodiments, the method further includes determining that the combined potential IBD segments have a minimum length in centimorgans and storing the combined potential IBD segments as IBD segments for the plurality of individuals.

In another aspect of the embodiments herein, a computer implemented method of processing haplotypes to reduce errors when determining identity by descent (IBD) segments between haplotypes is provided, the method including: providing two or more paired haplotypes strings for identification of IBD segments therebetween, each of the two or more paired haplotype strings representing a sequence of allele values at polymorphic sites in a haplotype of an organism; and computationally iterating through the two or more paired haplotype strings by: (i) identifying a first potential IBD segment between the two or more haplotype strings by identifying matches among alleles of the haplotype strings; (ii) comparing the first site of the first potential IBD segment to the last site of a previously identified second potential IBD segment (iii) determining that the last site of the second potential IBD segment and the first site of the first potential IBD segment are within a threshold number of sites of each other; and (iv) merging the first potential IBD segment and the second potential IBD segment to form a combined potential IBD segment.

In another aspect of the embodiments disclosed herein, a computer implemented method of processing haplotypes to reduce errors when determining identity by descent (IBD) segments between haplotypes is provided, the method including: (a) computationally identifying initial IBD segments between two or more haplotype strings by identifying first matches among alleles of the haplotype strings using a plurality of templates, each including a unique arrangement of masked and unmasked sites in a window of consecutive haplotype sites; and (b) providing information characterizing the initial IBD segments to a hidden Markov model (HMM) which removes potential phase switch errors to produce final IBD segment, wherein the HMM analyzes the information characterizing the initial IBD segments using distances between consecutive haplotype sites on a chromosome, one or more rates of recombination based on meiosis, and one or more rates of phase switch error based on a phasing method employed to phase the haplotypes.

In some embodiments, the method further includes, after (a) and before (b), removing some initial IBD segments determined to belong to haplotypes having less than a threshold amount of initial IBD segments, wherein the initial IBD segments provided to the HHM in (b) have had some initial IBD segments removed. In some embodiments, the threshold amount of initial IBD segments is less than two initial IBD segments per chromosome.

In another aspect of the embodiments described herein, a computer implemented method of determining identical-by-descent (IBD) segments is provided, the method including: (a) for each polymorphic site in a series of polymorphic sites of two individuals, obtaining an IBD state that indicates whether alleles of the two individuals at the polymorphic site are part of an IBD segment, and, if so, which of the two individuals' phased haplotypes are part of the IBD segment, wherein the series of polymorphic sites are included in one or more pairs of chromosomes; and (b) applying a hidden Markov model (HMM) to the IBD states to produce one or more error-corrected IBD segments, wherein the HMM model takes as input, in addition to the IBD states as observed IBD states, (i) a rate of recombination based on a number of meioses, and (ii) at least one rate of phase switch error based on a phasing method employed to phase the haplotypes; wherein applying the HMM removes likely phase switch errors and produces the error-corrected IBD segments based on a most likely sequence of hidden IBD states; and wherein operations (a) and (b) are performed by one or more processors of a computer system.

In some embodiments, the HMM takes as input: (iii) genetic distances between consecutive sites on a chromosome. In some embodiments, transition rates of the HMM are based on a rate at which IBD segments start, which rate is modeled as a function of the number of meioses. In some embodiments, the rate at which IBD segments start ($\alpha_s$) is modeled as follows:

$$\alpha_s = \frac{1}{1 + (100.0 \times m)}$$

wherein m is the number of meioses. In some embodiments, transition rates of the HMM are based on a rate at which IBD segments end. In some embodiments, the rate at which IBD segments end is modeled as a function of the number of meioses. In some embodiments, the rate at which IBD segments end ($\alpha_e$) is modeled as follows:

$$\alpha_e = \frac{m}{100.0}$$

wherein m is the number of meioses. In some embodiments, the IBD states include nine different IBD states, which indicate nine conditions of zero IBD, half IBD, and full IBD. In some embodiments, transition rates of the HMM are based on a transition matrix $Q_\alpha$ in FIG. 8B. In some embodiments, transition rates of the HMM are weighted by a probability that full IBD between the two individuals is truly present. In some embodiments, the probability that full IBD between the two individuals is truly present is modeled as a logistic function of an amount of estimated full IBD. In some embodiments, the probability that full IBD between the two individuals is truly present ($\beta$) is modeled as follows:

$$\beta = \frac{1}{1 + e^{\eta(0.125-\iota_2)}}$$

wherein $\iota_2$ is the amount of estimated full IBD, and $\eta$ is an empirical parameter defining the steepness of the logistic function. In some embodiments, the transition rates are weighted by weighting transitions into full IBD states with $\beta$, and weighting transitions out of full IBD states with $1/\beta$. In some embodiments, the IBD states include 9 different IBD states, and the transition rates are based on a transition matrix $Q_\beta$ in (Eq. 5). In some embodiments, transition rates of the HMM are based on the at least one rate of phase switch error. In some embodiments, the at least one rate of phase switch error includes a rate of phase switch error for each of the two individuals, there are 4 types of phase switch errors, the IBD states include 9 different IBD states, and the transition rates are based on a 36×36 transition matrix Q in (Eq. 6). In some embodiments, transition probabilities of the HMM are based on the genetic distances between consecutive sites on a chromosome.

In some embodiments, the transition probabilities are obtained by exponentiating a transition matrix. In some embodiments, transition probabilities of hidden IBD states $Y_{\iota+1}$ given hidden IBD states $Y_\iota$ are modeled as: $P(Y_{\iota+1}|Y_\iota, m, \mu_0, \mu_1, \iota_2)=e^{Qd\iota}$ wherein m is the number of meioses, $\mu_0$ is a phase switch error rate for a first individual of the two individuals, $\mu_1$ is a phase switch error rate for a second individual of the two individuals, $\iota_2$ is an amount of estimated full IBD, Q is a transition matrix described by Eq. (Q), and $d_\iota$ is the genetic distances between sites 1 and $\iota+1$.

In some embodiments, emission probabilities of the HMM are dependent on phase switch errors. In some embodiments, the emission probabilities are defined by a uniform error term that weights probabilities of observed IBD states based on four different ways the two individuals may be in phase switch errors. In some embodiments, (b) includes using transition probabilities and emission probabilities of the HMM to identify the most likely sequence of hidden IBD states given the observed states. In some embodiments, the mostly likely sequence of hidden IBD states is identified using a Viterbi dynamic programming process. In some embodiments, the method further includes: performing (a) and (b) for a plurality of iterations, each iteration using a different number of meioses for the rate of recombination, thereby producing a plurality of sets of error-corrected IBD segments; and selecting a set of error-corrected IBD segments having a highest likelihood or probability in the plurality of sets as a final estimate of one or more IBD segments. In some embodiments, the different numbers of meioses are in a range from 1 to 14. In some embodiments, the method is initiated when the two individuals' IBD segments including the series of polymorphic sites meet a criterion. In some embodiments, the two individuals' IBD segments include two or more IBD segments on a single chromosome. In some embodiments, the two individuals' IBD segments exceed a minimum total amount of shared IBD Although the examples herein concern humans and the language is primarily directed to human concerns, the concepts described herein are applicable to genomes from any biological organism. These and other objects and features of the present disclosure will become more fully apparent from the following description and appended claims in conjunction with the associated drawings.

BRIEF DESCRIPTION OF THE DRAWINGS

The accompanying drawings, which are included as part of the present specification, illustrate embodiments and, together with the general description given above and the detailed description of the embodiment given below, serve to explain and teach the principles described herein.

FIG. 4 illustrates haplotype strings, a positional prefix array, and a divergence array in accordance with various embodiments discussed herein.

FIG. 5C presents pseudocode for an algorithm according to various embodiments herein.

FIG. 9B illustrates a transition matrix that may be used as part of a HMM according to various embodiments herein.

FIGS. 20A and 20B illustrate the runtime of various methods and the parameters used for assessing runtime.

DETAILED DESCRIPTION

Figure 1:
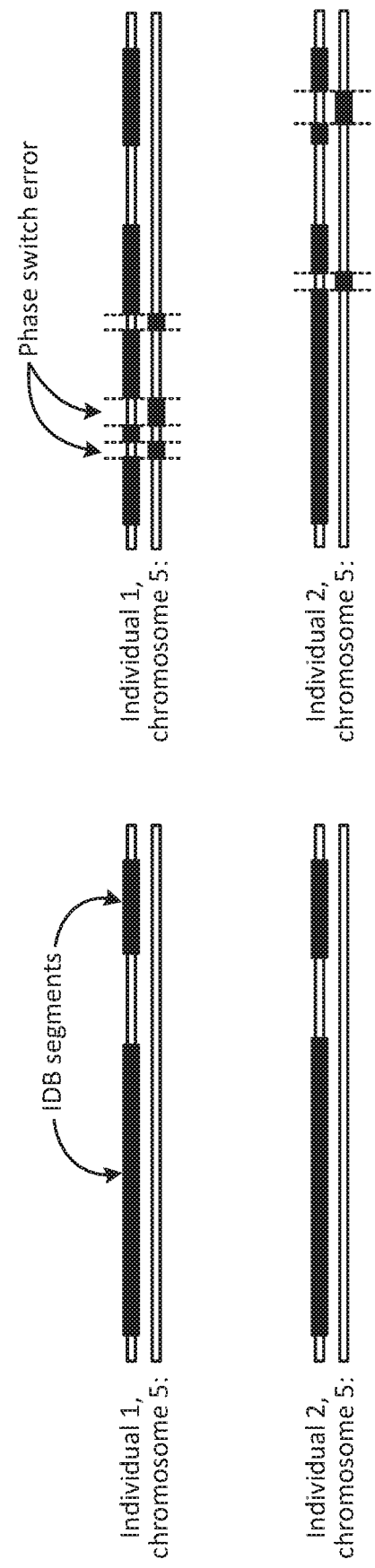
FIG. 1 presents possible phase switch errors in long IBD segments.

The disclosure concerns methods, apparatus, systems, and computer program products for estimating IBD segments between individuals using haplotype data.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art.

Definitions

As used herein, the singular terms "a," "an," and "the" include the plural reference unless the context clearly indicates otherwise.

Unless otherwise indicated, nucleic acids are written left to right in 5' to 3' orientation and amino acid sequences are written left to right in amino to carboxy orientation, respectively.

The term "plurality" refers to more than one element. For example, the term is used herein in reference to a number of nucleic acid molecules or sequence reads that is sufficient to identify significant differences in repeat expansions in test samples and control samples using the methods disclosed herein.

A DNA segment is identical by state (IBS) in two or more individuals if they have identical nucleotide sequences in this segment. An IBS segment is identical by descent (IBD) in two or more individuals if they have inherited it from a common ancestor without recombination, that is, the segment has the same ancestral origin in these individuals. DNA segments that are IBD are IBS per definition, but segments that are not IBD can still be IBS due to the same mutations in different individuals or recombinations that do not alter the segment.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cell-free DNA (cfDNA) molecules. The term "polynucleotide" includes, without limitation, single- and double-stranded polynucleotides.

The term "parameter" herein refers to a numerical value that characterizes a physical property. Frequently, a parameter numerically characterizes a quantitative data set and/or a numerical relationship between quantitative data sets. For example, a ratio (or function of a ratio) between the number of sequence tags mapped to a chromosome and the length of the chromosome to which the tags are mapped, is a parameter.

The term "site" refers to a unique position (i.e. chromosome ID, chromosome position and orientation) on a reference genome. In some embodiments, a site may be a residue, a sequence tag, or a segment's position on a sequence.

The term "based on" when used in the context of obtaining a specific quantitative value, herein refers to using another quantity as input to calculate the specific quantitative value as an output. The specific quantitative value may be based on multiple other quantities, not just the one identified.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

Introduction and Overview

Modern genetic data sets already number in the millions of genomes and are growing rapidly. Inferring the genomic location and length of identical-by-descent (IBD) segments among the related individuals in these data sets is a central step in many genetic analyses. IBD estimates can best be exploited when they are made using phased haplotypes; this means each individual in the data set is represented by two sequences each of which consist of alleles co-located on the same chromosome and inherited from a different parent. IBD estimates that are phase aware can improve relationship and pedigree inference, allow health and trait inheritance to be traced, and make possible a range of other inferences regarding demographic history and ancestry that are not possible when IBD estimates are made using only unphased genotype data.

Estimating phase aware IBD segments is challenging not only because of the large sizes of the genomic data sets but also due to two types of error that break up IBD segments: genotyping error and phase switch/phasing error. Because IBD segments are broken up by meiotic recombination events they are expected to be longer for close relatives. However, long IBD segments are more likely to be impacted by genotype and phasing errors compared to short segments. Thus, errors are particularly problematic when detecting IBD among individuals that are closely related (e.g. first, second, and third degree relatives) since long IBD segments are more likely to be fragmented by these errors. This makes accurate inference of phase aware IBD among close relatives particularly problematic.

Genotyping error is error introduced via genotyping (e.g., sequencing) in which an allele that is actually of one type (e.g., a T) gets called a different allele (e.g., an A). This commonly has the effect of prematurely terminating a sequence of matches that would otherwise be long enough to be considered an IBD segment. Phase switch error is error introduced by phasing: maternal and paternal copies are reversed. See FIG. 1. In some typical cases, statistical phasing processes introduce a phase switch error, on average, about every 12 centimorgans.

FIG. 1 illustrates phase switch error in fragment long IBD segments. As shown in the left panel, two IBD segments (thicker lines) are shared on a single chromosome in two related individuals (top and bottom). As shown in the right panel, phase switch errors (illustrated by vertical dashed lines) occur at different positions along the chromosome in the two individuals, fragmenting the true IBD segments into many erroneous false IBD segments. The individual represented by the top two haplotypes has six phase switch errors and the individual represented by the bottom two haplotypes has four phase switch errors.

Various embodiments disclosed herein address phase shift and/or genotyping error and thereby improve IBD segment identification using phased haplotype data. In certain embodiments, computational methods employ different templates of masked and unmasked regions to exclude certain haplotype sites during IBD segment identification. By combining results using different templates, the computational methods mitigate genotyping error. In certain embodiments, a probabilistic model considering meiotic rates, phase switch error in phased data, and distance between adjacent haplotype sites is used to identify and remove some phase shift error. In some implementations, phased haplotype data is processed using a method based on the positional Burrows-Wheeler transform (PBWT) and a probabilistic hidden Markov model (HMM). In some implementations, phased haplotype data is processed using a method based on the PBWT and a heuristic to correct phase switch errors. These approaches have been found to make fast and accurate phase aware IBD estimates.

Various IBD segment finding methods to compute phase aware IBD segments are disclosed herein. These methods may minimize genotyping and phasing error using one or more of the following techniques:

1. To handle genotyping error, an IBD segment computation procedure passes multiple digital templates over phased haplotypes to differentially mask haplotype sites, thereby temporarily ignoring different sites of potential genotype error. The IBD segments being generated by the different templates are combined to effectively remove fragmentation caused by genotyping error. In some embodiments, the procedure is a templated positional Burrows-Wheeler transform. This is the positional Burrows-Wheeler transform (PBWT; Durbin 2014) with substantial modifications to handle genotyping errors and missing data.

2. To handle phase switch error reduction, IBD segments that are likely fragmented by phase switch errors introduced during statistical phasing are addressed using a heuristic that recognizes likely occurrences of phase switch errors and/or a probabilistic model that accounts for error rates of the phasing techniques.

In certain embodiments, the model is applied to haplotype/IBD segment data generated using the templating approach described in 1. Some implementations apply a hidden Markov model (HMM) that accounts for both recombination and the phase switching process to reduce these errors. The HMM passes along the chromosomes of the two individuals "stitching" fractured IBD segments together.

In some embodiments, a heuristic is applied that identifies fractured IBD segments based on potential IBD segments that start or end within a distance of the start or end of another IBD segment. The heuristic may stitch the IBD segments together by, for example, swapping haplotype segments in a target individual. In some embodiments, the heuristic may be applied as potential IBD segments are generated using the templating approach described in 1 without a separate iteration over the IBD segment data. In some embodiments, the heuristic assumes that IBD segments within a threshold distance of each other are likely to be a single IBD segment fractured by one or more phase switch errors.

Figure 2A:
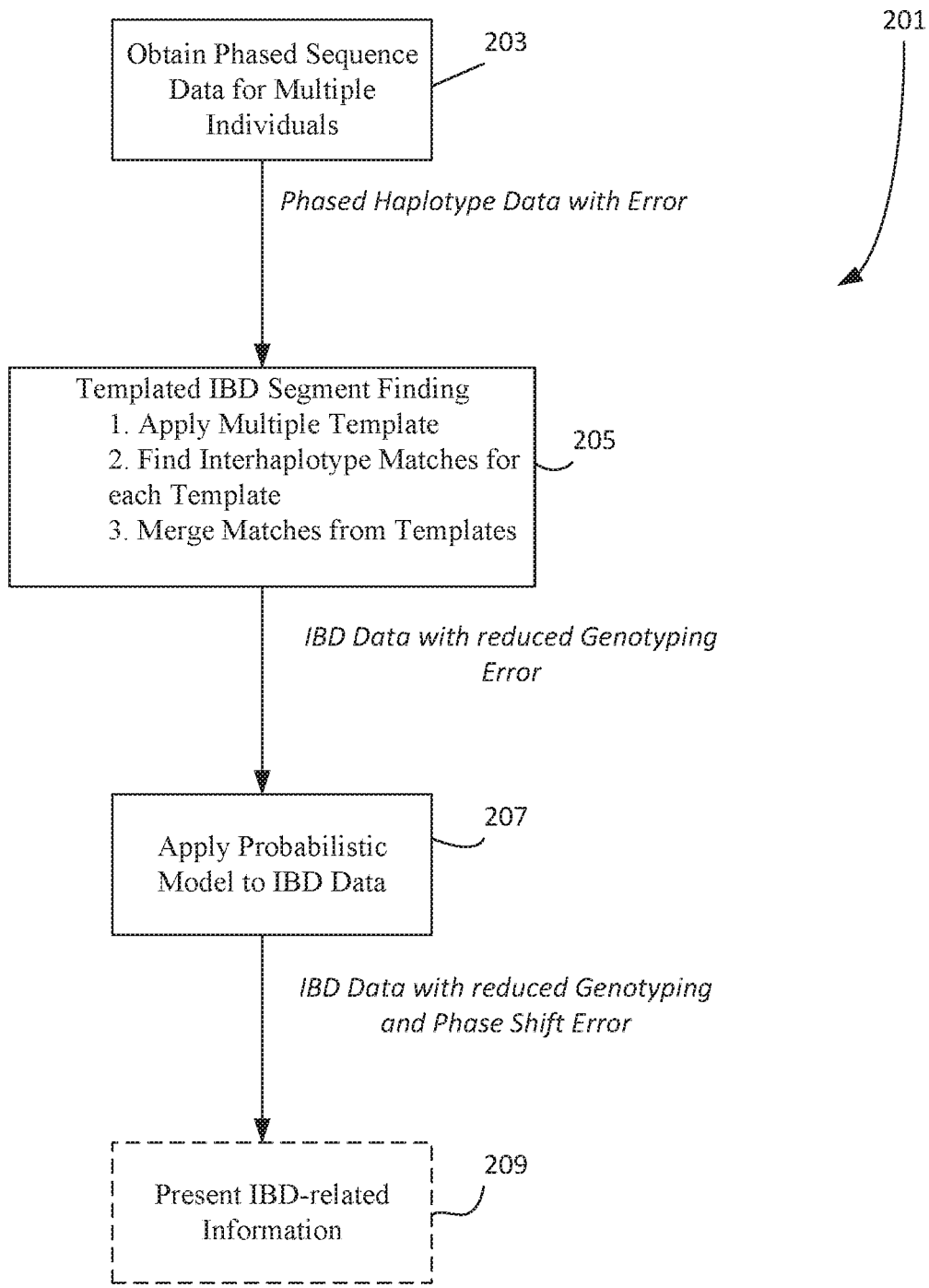
FIGS. 2A and 2B present example process flows according to various embodiments discussed herein.

An example workflow is illustrated in the flow chart of FIG. 2A. As shown, a process 201 begins by initially obtaining phased sequence data for two or more individuals who are to be compared to detect IBD segments. See block 203. In various embodiments, phased data for many more individuals is obtained. In some contexts, hundreds, thousands, or even millions of individuals have their phased haplotype data compared using methods disclosed herein. In some implementations data for greater than about 10 million individuals' phased haplotype data are compared. In any event, the operation 203 involves identifying individuals or haplotypes on which an IBD comparison is to be run.

The phased data includes two strings of haplotype data for each individual (one per chromosome). In other words, there are four haplotypes to be considered for two individuals. Phased haplotype data may be obtained from various sources including statistical techniques such as BEAGLE, FINCH, EAGLE, and other known techniques. An example discussion of phasing techniques is presented in U.S. Pat. No. 9,836,576, filed Mar. 13, 2013, and incorporated herein by reference in its entirety.

The haplotype data may be represented as strings of allele values (e.g., 1s and 0s) for sites in the haplotype, each of which is the site of a polymorphism. Each such site may be referred to as an index in the haplotype string. In various embodiments, the process assumes that each haplotype site is a biallelic site on a chromosome. It may be given a value of, e.g., 0 for one allele and a value of 1 for the other allele. A typical chromosome may provide hundreds of thousands of sites. Each haplotype may be given its own unique identifier, which may be arbitrarily set.

The phased haplotype data is provided to a first processing block as illustrated by a block 205. This processing may reduce the fragmenting impact of genotyping error in IBD segment finding. In the first processing block, multiple operations are performed in parallel, sequentially, or in some combination thereof. In various embodiments, significant computational efficiency is realized by performing these operations together for a given haplotype (e.g., in an inner loop of a software routine as illustrated in the sample code below). The operations performed in the first phase include the following: (a) applying digital templates with masked and unmasked positions to exclude certain haplotype sites along the length of the haplotype, (b) identifying matching allele values at unmasked positions along the haplotypes to identify putative IBD segments for the various digital templates, and (c) merging the resulting IBD segments (e.g., as they are being generated) from the various digital templates.

As explained in more detail elsewhere herein, the IBD segment finding logic may be implemented using the PBWT method. Regardless of whether PBWT or another IBD segment finding process is used, the method produces multiple putative IBD sub-segments, one for each different digital template used. The method also merges or stitches together the IBD sub-segment as generated using each of the various templates. As suggested, in some embodiments, the templating, comparing, and merging operations are performed at a given site, before considering the next site, where the three operations are again performed.

There are many different ways to construct the digital templates. In various embodiments, they are constructed as small windows that can be "slid" or "ratcheted" along the length of the haplotype strings, considering consecutive sub-segments of the haplotype sites as they go. Criteria to consider in choosing template structures are the length of the template, the number of masked or null sites in the template, and the arrangement of masked and unmasked sites in the template. Typically, full sets of templates are used in the process that contain all possible arrangements of masked and unmasked sites in a template length. An example set of four site digital templates, each employing two masked and two unmasked positions is described below. Of course, the process may alternatively employ larger (or smaller) templates and/or use templates having a higher or lower proportion of null positions per template.

The output of the first processing block implemented in operation 205 is a set of IBD segments or other haplotype matching data for combinations of the various individuals whose phased haplotype data is processed. This data is then passed to a second processing block for processing as illustrated in an operation 207. A goal of this second operation may involve reducing the fragmenting impact of phase switch error in IBD segment finding.

In operation 207, the haplotype/IBD data is subjected to a probabilistic model that accounts for recombination rates based on meioses, which vary based on degree or relatedness of any two individuals, and rates of phase switch errors introduced by the phasing technique(s) employed to generate the phased haplotype data. The model may also account for other inputs such as the genetic distance between adjacent sites on the haplotype and/or the probability of having full IBD state. As exemplified below, a hidden Markov model may be used to implement the probabilistic model.

An optional last operation of the process 201 involves presenting the processed IBD information in a way that can show the degree of relatedness of the two or more haplotypes that are compared. See the operation represented in block 209.

Figure 2B:
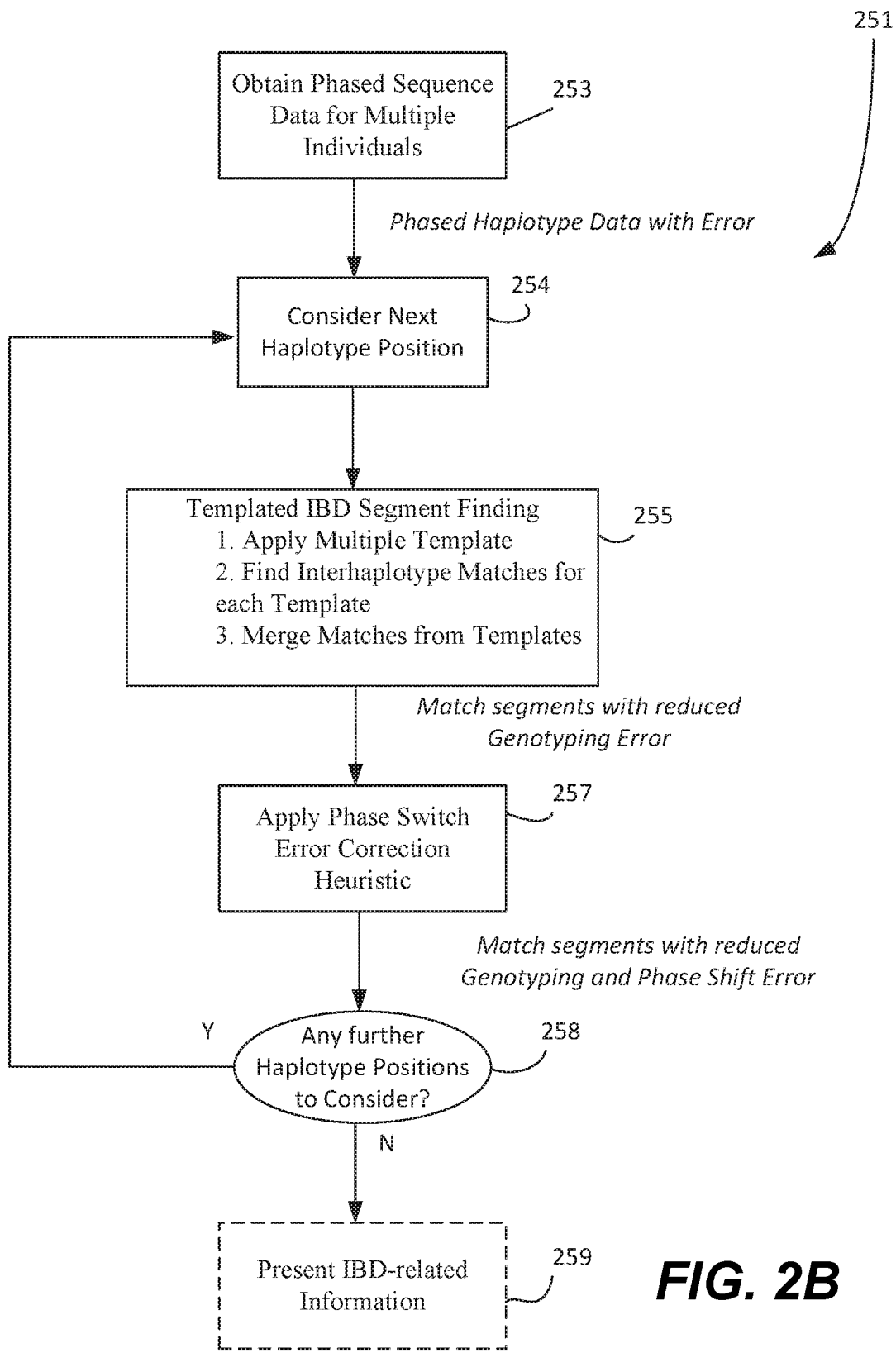

Another example workflow is illustrated in the flow chart of FIG. 2B. As shown, a process 251 begins by initially obtaining phased sequence data for two or more individuals who are to be compared for identifying IBD segments. See block 253. As with other embodiments, phased data for many more individuals may be obtained, e.g., hundreds to millions of individuals. Regardless, the operation of block 253 involves identifying individuals and/or haplotypes on which an IBD comparison is to be run.

Computational aspects of process 251 include sequentially considering haplotype positions for genotype errors and phase switch errors within individual haplotypes while keeping track of match segments between haplotypes. Processing each new haplotype position is initiated at a process operation 254, which selects the next position in the haplotypes under consideration.

For a given haplotype position, a first processing operation 255 considers possible errors in the individual haplotypes using multiple templates such as those described elsewhere herein. Haplotype position matches are determined using these templates, and, from these results, an overall decision on matching segments is made. In some implementations, the resulting match segments have reduced genotyping error.

The haplotype position under consideration is then analyzed in a processing operation as illustrated in block 257.

A result of this operation may involve reducing the fragmenting impact of genotyping error in IBD segment finding.

In operation 257, the haplotype/IBD data may be analyzed by one or more phase switch heuristics and/or models that identify situations where phase switch errors are likely to have occurred. As an example, a heuristic may identify situations where one or more IBD segments between individuals end at a first position and then new IBD segments begin at a second position within a threshold distance from the first position. An identified likely phase switch error may be corrected by joining the IBD segments in an individual identified to possess the likely phase switch error. In some cases, error is corrected by swapping haplotype segments within the identified individual. Regardless of the technique implemented in operation 257, a result of the operation may involve reducing the fragmenting impact of phase switch error in IBD segment finding. In operation 258 the process may loop back to operation 254 if there are any further haplotype positions to consider.

An optional last operation of the process 251 involves presenting the processed IBD information in a way that can show the degree of relatedness of the two or more haplotypes that are compared. See the operation represented in block 259.

IBD Segments

Various repeat expansion analyses using DNA samples involve aligning or mapping sequence reads from a sequencer to a reference sequence. A reference sequence may be the sequence of a whole genome, the sequence of a chromosome, the sequence of a sub-chromosomal region, etc. From a computational perspective, repeats create ambiguities in alignment, which, in turn, can produce biases and errors even at the whole chromosome counting level. Paired end reads coupled with adjustable insert length in various embodiments can help to eliminate ambiguity in alignment of repeating sequences and detection of repeat expansion.

In various embodiments, a goal of the process is to use alignment of multiple haplotypes to determine genetic relationship(s) between two or more individuals, or in some cases that potentially involve inbreeding, within a single individual. Fundamentally, the process determines relationships between two haplotypes. IBD may be used for this purpose.

IBD can be understood in the context of meiosis and recombinable DNA. Because of recombination and independent assortment of chromosomes, the autosomal DNA and X chromosome DNA (collectively referred to as recombinable DNA) from the parents is shuffled at the next generation, with small amounts of mutation. Thus, only relatives will share long stretches of genomic regions where their recombinable DNA is completely or nearly identical. Such regions are referred to as "identical-by-descent" (IBD) regions because they arose from the same DNA sequences in an earlier generation/common ancestor.

In some embodiments, locating IBD regions includes sequencing the entire genomes of the individuals and comparing the genome sequences. In some embodiments, locating IBD regions includes assaying a large number of markers that tend to vary in different individuals and comparing the markers. Examples of such markers include Single Nucleotide Polymorphisms (SNPs), which are points along the genome with two or more variations; e.g., Short Tandem Repeats (STRs), which are repeated patterns of two or more repeated nucleotide sequences adjacent to each other; and Copy-Number Variants (CNVs), which include longer sequences of DNA that could be present in varying numbers in different individuals. Long stretches of DNA sequences from different individuals' genomes in which markers in the same locations are the same indicate that the rest of the sequences, although not assayed directly, are also likely identical.

Techniques for matching individual haplotypes, e.g., by using IBD are known. Some of them cannot efficiently handle large numbers of haplotypes and even those that can, do not adequately account for errors. Some discussion of IBD segments may be found in U.S. Pat. No. 8,463,554 filed Dec. 22, 2009, and incorporated herein by reference in its entirety. Templated PBWT To initially detect IBD segments one may extend the positional Burrows-Wheeler transform (PBWT; Durbin 2014). In certain embodiments, a PBWT process is implemented according to the following description. Initially, each haplotype under consideration is given its own unique identifier, which may be arbitrarily set. Then, during execution, the method steps through the sites of all haplotypes under consideration, position-by-position, starting at a first position, which may be identified as position 0. As the method steps through the haplotype sites, it keeps track of two arrays, which are updated for every position (index) in the haplotypes. Also, during a pass through the haplotype sites, a templated PBWT process may apply one, some, or all of the digital templates at each position.

The first array is a "positional prefix array" that contains a list of all haplotypes under consideration. It is populated with IDs of all the haplotypes. A separate instance of the positional prefix array is produced each time a new site is encountered while traversing the haplotype string. Over the course of the process, and while certain haplotypes have identical allele values from one position to the next, these haplotypes are grouped together in the positional prefix array. In other words, haplotypes having matching allele values, remain together (in the same block) within the positional prefix array for as long as their alleles match. By keeping the haplotypes together while alleles match, the positional prefix array contains information about putative IBD segments.

The second array is a "divergence array" that indicates where matches between any two haplotypes under consideration began. It reflects how many positions/sites back in the haplotype string until there was a difference. In other words, this matrix keeps track of the last time that two haplotypes did not match by, e.g., providing the index value of the last mismatch for any two haplotypes.

Figure 3:
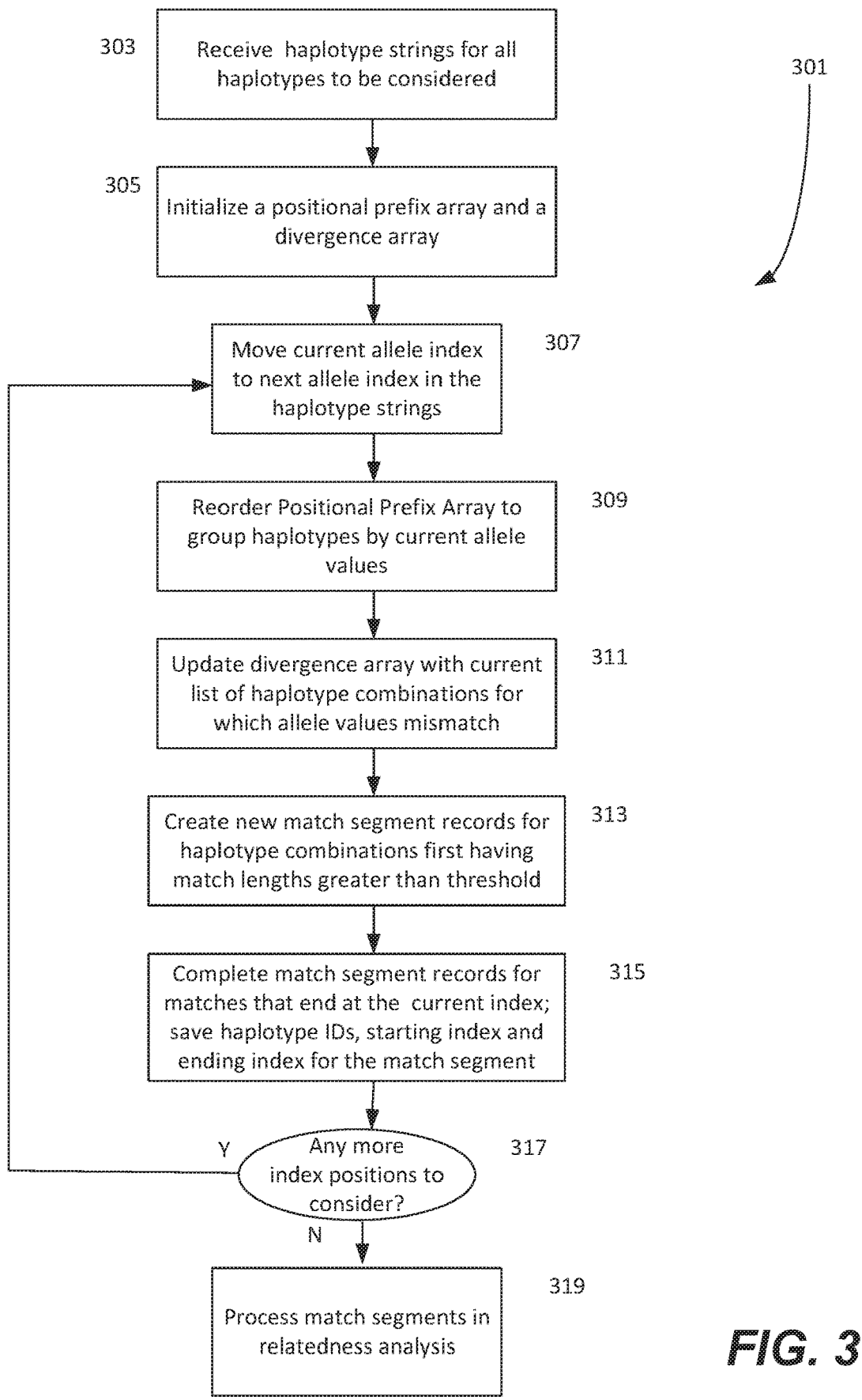
FIG. 3 presents an example process for finding IBD segments.

An example of a general IBD segment finding process 301 is depicted in FIG. 3. As illustrated, the process begins by receiving haplotype strings representing allele values across all haplotypes to be considered in the process. See block 303. This may correspond to block 203 in FIG. 2A and/or block 253 of FIG. 2B.

Before considering the first site in the haplotypes, the process lists all haplotypes in the positional prefix array. It may do this randomly or in some order, but typically it does not yet account for the allele values at any haplotype site. The individual haplotypes may be listed by unique identifiers. Further, before considering the first site on the haplotype, the values in divergence array are all set 0 because there are no previous sites that have been considered. The array initializations are illustrated by operation 305 in process 301 of FIG. 3.

Figure 4:
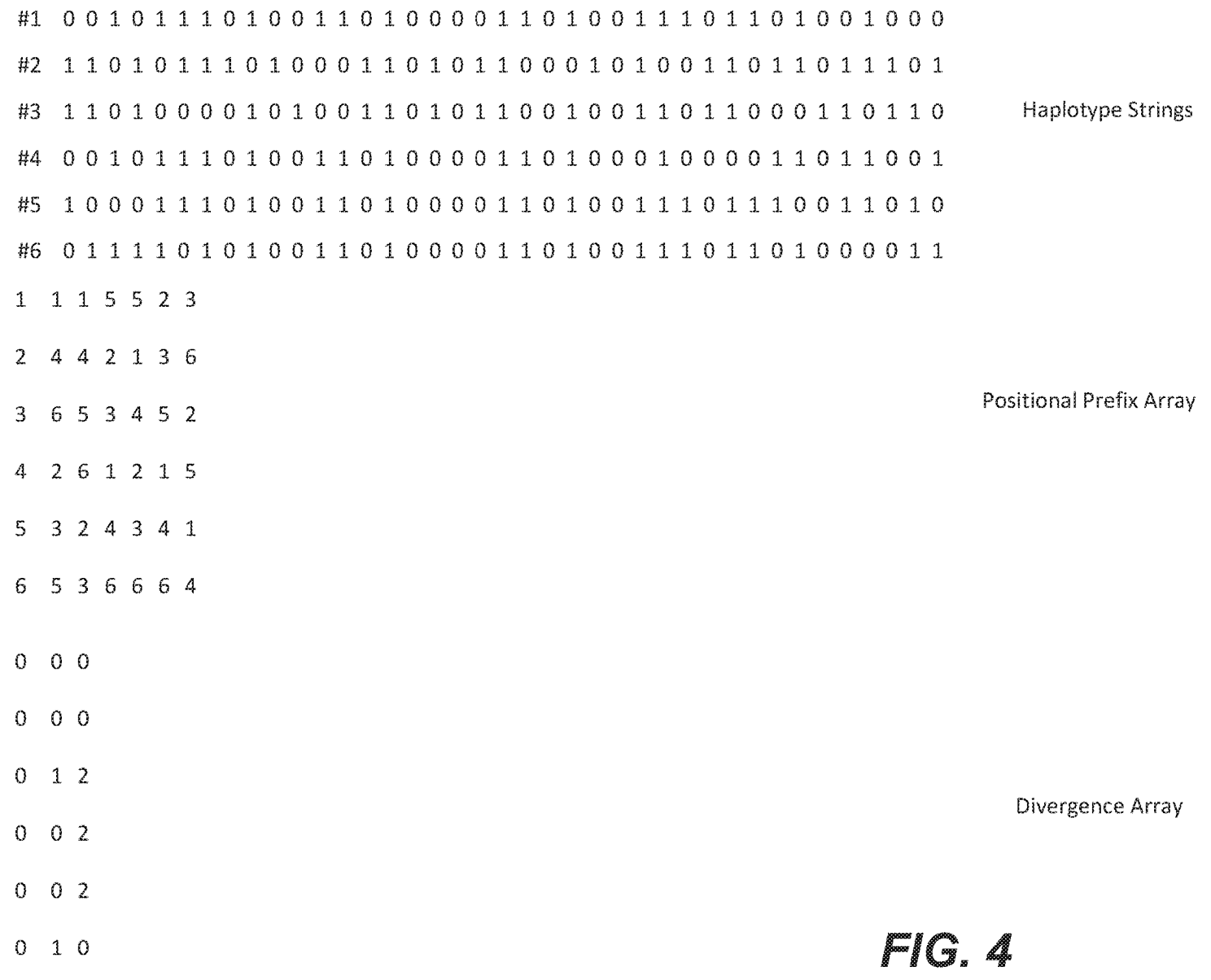

At the first site of the haplotype strings (which may be reflected as the first column in an aligned set of the haplotype strings), the process goes through all haplotypes in the order of the positional prefix array (which may initially be random or otherwise arbitrary) and orders the haplotypes such that those that have a first allele value (e.g., 0) in the current position are grouped together at the top, and all that have a second allele value (e.g., 1) in the position are grouped together at the bottom. See operation 309. Of course, this order could be reversed or even extended in the case of multiallelic sites. Either way, this operation produces a new positional prefix array in which all haplotype indexes that have a 0 at the current position are grouped together in the array, and all haplotype indexes that have a 1 at the position are grouped together. By "grouped together," it is meant that haplotype identifiers are provided in adjacent positions in the positional prefix array. This is illustrated in FIG. 4 which shows a group of six haplotype strings and the associated positional prefix array at a few haplotype sites. Obviously, a typical haplotype has many more sites than illustrated for the haplotypes in FIG. 4. Further, a typical IBD segment finding process may simultaneously evaluate many more haplotype strings (e.g., hundreds, thousands, or millions).

Regarding the divergence array, by considering the allele values at the first index position with those in the previous position (which does not exist in this iteration), the process notes that all potential IBD segments begin at site 0 and therefore they effectively have a mismatch at position 0. Therefore, the first entry in the divergence array is all zeros. See operation 311 in process 301 and the first column in the divergence array of FIG. 4.

The order of haplotypes in the divergence array is the same as in the positional prefix array. Using this order of haplotypes in the divergence array, the values in the divergence array are, for currently matching haplotypes, the sites (index values) of the first matching position between the two adjacent haplotypes within the array. Thus, for adjacent haplotypes that currently match, the value in the divergence array is the first matching position of the current segment. However if two adjacent haplotypes no longer match at the current site the method assigns the next site to the new div array even though it has not peeked ahead and checked if the two haplotypes actually match at the next site. If, in the next iteration, the method learns that the segments still do not match, the relevant value in the divergence array simply gets updated again.

Returning to FIG. 3 and ignoring for now operations 313 and 315, when the process has completed operations on a given haplotype site, it determines whether there are any further sites to consider. See operation 317. If there are such sites, the process loops back to an operation 307, where the next site/index is selected for consideration.

At the next column (associated with the next site in the aligned haplotype strings), the process again goes through the haplotypes and again rearranges the haplotype identifiers in the positional prefix array so that those having the same allele value at the current position are grouped together, e.g., all haplotypes having a 0 allele value in the current position are grouped at the top of the array and all those having a 1 allele value are grouped at the bottom. Haplotype strings that have the same alleles over multiple consecutive positions stay near one another in the positional prefix array.

The divergence array uses the new arrangement of haplotypes (from the positional prefix array), flags any mismatches between adjacent haplotypes and the current position and inserts the next haplotype site number for mismatching pairs. The next site number is the location of the next possible start position for a new match segment.

Thus, in some implementations, element i in the divergence array indicates when a current segment match began between the haplotype at ppa[i] and the haplotype at ppa[i–

1]. For purposes of example, consider the case where at position 5 in the haplotype alignment, the positional prefix array has the following values:

2
3
1
4

And the divergence array has the following values:

0
0
3
2

In this example haplotypes 2 and 3 have a match that extends from the beginning of the alignment (position 0) to the current position (position 5). Haplotype 1 matches with haplotype 3 from position 3 to position 5 (which also implies haplotype 1 and haplotype 2 have the same match). And haplotype 4 matches with haplotype 1 from position 2 to position 5 (which also implies haplotype 4 matches haplotypes 1, 2, and 3 between positions 3 and 5). There are no mismatched haplotypes at the current site in this example. The routines use the alleles at the current position in the alignment to construct the divergence array for the next position. So, in the above example, if at position 5 two haplotypes do not match, the routine inserts 6 into the position of the haplotypes in the divergence array. Note that the method does not check whether the two haplotypes actually match at position 6, which is why the divergence array does not always contain the beginning position of matches. Once the method actually visits position 6 this value will be overwritten if the haplotypes do not match at site 7. The method continues in this fashion (overwriting values in the divergence array) until actual matches are found.

Over the course of the process, the lengths of matching segments of all haplotype pairs are tracked. When the match length of two haplotypes is greater than a preset threshold, the process flags the two haplotypes as having a potential IBD segment. In the example of process 301, it does this by creating new match segment records when two haplotypes have a number of consecutive shared matches that is greater than threshold number of consecutive sites. See operation 313. The threshold value may be chosen to balance speed and sensitivity. In certain examples, the threshold number is between about 50 and 1000 sites (e.g., about 200 matching sites). Similarly, the process may complete a match segment record when two matching haplotypes finally diverge in allele values, thereby ending the match segment. See operation 315. To this end, the process may maintain a separate report populated with matches of greater than the threshold length. The matches may be identified by start position and end position (indexes) and the haplotypes involved in the match (e.g., haplotype ID #11 and haplotype ID #5). In certain embodiments, the match segment includes both the starting and ending sites of the match segment.

In cases where a match segment does not end—such as when the end of a haplotype string ends and there are no further sites to consider—the process may still flag the match segment for further consideration. As with matches having defined end points, the match is identified by the two matching haplotypes and their starting index for the match segment. The ending index for the match region is the site at the end of the haplotype.

For the sake of clarity, the example of FIG. 3 does not illustrate treatment of the haplotype strings by different digital templates. This will be discussed below.

The process 301 proceeds through operations 307-315 for each successive haplotype site and reorders the haplotype IDs in the positional prefix array based on matches (the haplotypes having a 0 at the current position are grouped together and those having a 1 are grouped together).

In general, the haplotypes that have long stretches of matched sites stay together in the positional prefix array for long durations. This is because all matching haplotypes stay together in the positional prefix array until one of them has a different allele value at a particular haplotype position. At that point, the one or more haplotypes that diverge from the larger group are moved to a different position in the positional prefix array. By preserving the positional prefix arrays for each position in the haplotype, the method keeps sufficient information to reconstruct all IBD segments for any two haplotypes. This includes all haplotypes under consideration, including the first and last haplotypes in the positional prefix array.

In the divergence array, the values for two adjacent haplotypes (in the array) remain at a value of their first match until they again mismatch, at which time the corresponding divergence array value is marked with the next index position after the new mismatch. FIG. 4 presents an example of positional prefix array values and divergence array values for a few sites on an alignment of haplotype strings.

When there are no further haplotype sites to consider, as indicated by process block 317, potential IBD segments have been identified and these may be processed in various ways such as, optionally, being used in a relatedness analysis of individuals whose haplotypes were considered in the analysis. See operation 319. Alternatively, and as described with reference to FIG. 2A and as further described below, the potential IBD segments may be further processed by a model such as an HMM model to correct for phase shift errors. However, it should be understood that this additional processing is optional, particularly in situations where phased haplotype data can be expected to have relatively few phase shift errors. In some embodiments, potential IBD segments that are flagged by the PBWT process, but are shorter than a defined genetic length, are excluded from further consideration. An example of a threshold genetic length is between about 1.5 and 3 centimorgans. Thus, for example, if a segment extends over 200 sites but does not extend the full required genetic distance, the method discards the segment.

The PBWT process, as well as many other IBD segment finding processes, assumes that there are no errors. If there is in fact an error, it may prematurely truncate a sequence of matches and/or artificially prolong a sequence. Typically, long matches that in fact exist (e.g., between close relatives) are prematurely broken due to genotyping and/or phase switch errors.

As mentioned, integrating digital templates into an IBD segment finding process can mitigate the impact of some errors, particularly genotyping errors. One approach employs a digital template that shifts over the haplotype strings and masks certain haplotype sites from consideration as it goes. This approach takes a normal haplotype alignment but applies the template to skip over some sites that would otherwise be considered. With the excluded sites removed from consideration, the process identifies putative IBD segment matches using a general approach such as PBWT. By masking some sites from comparison, sites of erroneous calls may be ignored. Some templates may consider the erroneously called alleles while others exclude them. By considering putative IBD segments created using all the templates, the process can remove breaks and more accurately identify complete IBD segments.

The template provides a sliding window of consecutive sites having, in some embodiments, a fixed mask pattern. The template is moved successively along the haplotype string, typically with no overlap of sites between one application of the template and the next. Other than masking some sites, the process is similar to a generic IBD segment finding method such as the PBWT process. That is, in some embodiments, the process generates a positional prefix array and a divergence array for haplotype strings modified by the template. In the course of the process, the computational system flags and records matching segments as before. But the matching segments produced by single templates have some sites excluded. In alternative embodiments, the templating function employs a probabilistic function to pick mask sites.

In some embodiments, the mask pattern is deterministic based on the template. The masking of sites may follow a specific pattern, based on each template, rather than a random selection or masking of sites. For example, the mask pattern may remain fixed as the process moves from one haplotype site to the next. In some cases, however, the mask pattern may vary as the process moves over haplotype sites, but such variation may be deterministic rather than random.

In certain embodiments, the process employs multiple fixed templates for a given matching problem. Examples of templates include ØhØh (all odd sites), hØhØ (all even sites), ØØhh, hhØØ, ØhhØ, and hØ↑7h, where sites at Ø will be masked out and only sites at h will be used to construct the method. The choice of templates to use together in a process may be made such that for the fixed length of the templates (e.g., the four site templates exemplified here), may guarantee that if there were any errors (e.g., two errors) within this window, at least one of these templates correctly report a match. For example, if there were errors at sites 2 and 4 at one application of a four site template, only the hØhØ would give an error-free read.

Depending on the number of indexes/sites in a template and the number excluded within a window, different numbers of templates may be used in a given process. Broadly, the total number of digital templates may be between 1 and k, where k is the number of haplotype sites in the window. In some implementations, the total number of digital templates is k!/(m! *(k-m)!), where k is the number of haplotype sites in the window and m is the number of masked sites in the window.

In certain embodiments, such as the case of a four site template with two null sites, six templates may be used. However, other template combinations may be employed; e.g., at least two templates, at least six templates, at least eight templates, at least ten templates, etc. In various embodiments, the templates are characterized by a ratio of masked to unmasked sites which ranges between about 1/w and (w−1)/w, where w is the length of the template window In various embodiments, the templates are characterized by a length equivalent to the total size of the haplotype alignment. As examples, a range of template lengths is between about three and ten consecutive sites.

A templating function can be tuned to alter sensitivity to error. As suggested, one templating function may be implanted as a decision tree that uses a window size of 4 haplotype sites and 6 templates, and so guarantees any matches within that 4 site window as long as there are no more than 2 errors. If i is the current template (range 0 to 5) and k is the current position within a template window (range 0 to 3), then this templating function T(i, k) may be represented as:

T(i, k):
  if i==0 and (k==0 or k==2):
    return 1
  else if i==1 and (k==1 or k==3):
    return 1
  else if i==2 and (k==0 or k==1):
    return 1
  else if i==3 and (k==2 or k==3):
    return 1
  else if i==4 and (k==0 or k==3):
    return 1
  else if i==5 and (k==1 or k==2):
    return 1
  else
    return 0

Figure 5A:
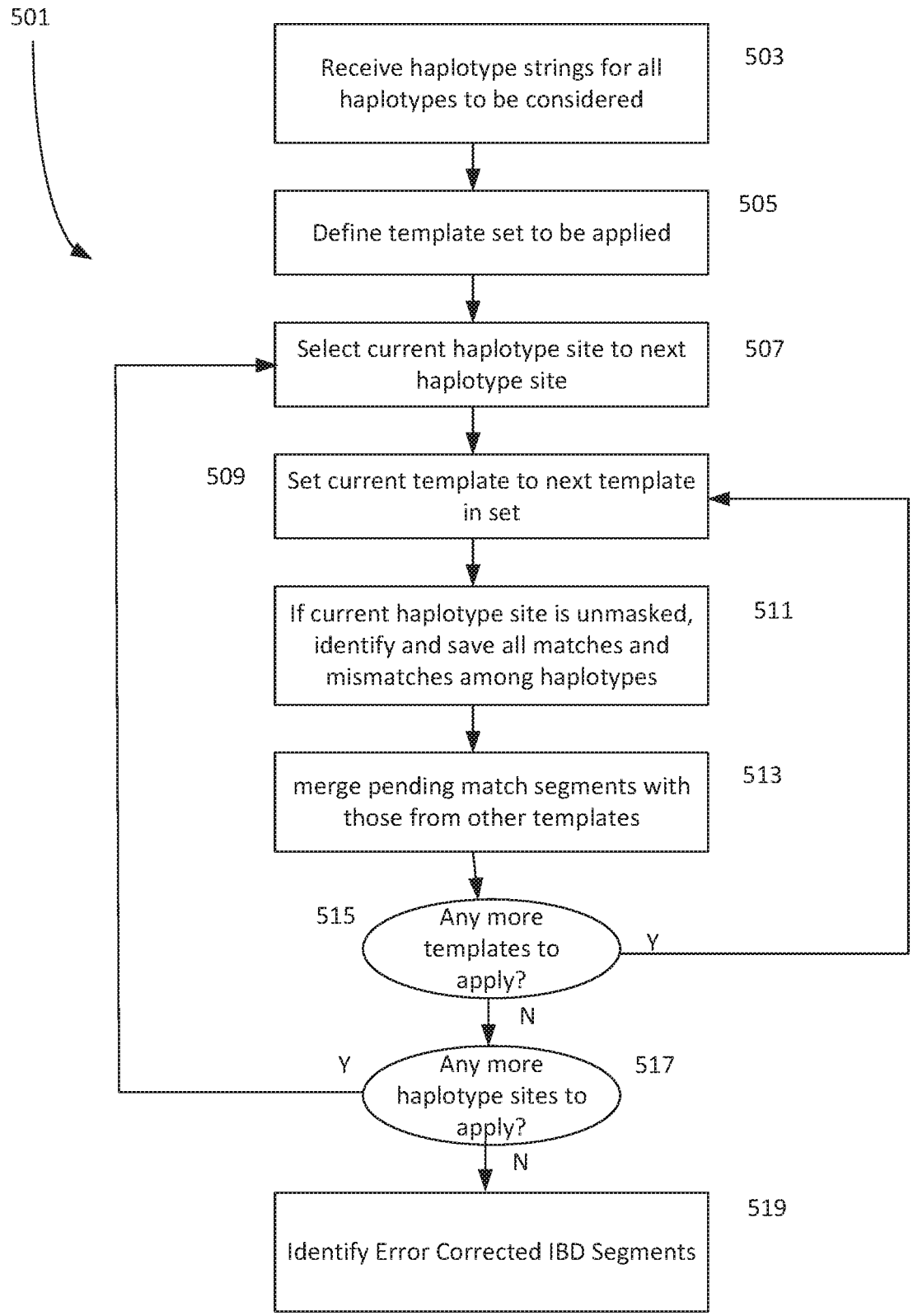
FIGS. 5A and 5B present process flows according to various embodiments herein.

FIG. 5A illustrates application of templates to an IBD segment finding method. The depicted process 501 begins by receiving data and setting up parameters for the routine. This may involve receiving phased haplotypes to be used in the templated matching routine (block 503), defining templates to apply (block 505), and setting up any needed matrices and arrays such as a positional prefix array and a divergence array. The depicted process loops over the various sites of the haplotypes, and at each site it loops over the available templates. This is depicted as follows.

The process increments to the next haplotype site at an operation 507, and while at the current site, it iterates over the various templates, starting by incrementing to the next template at an operation 509. While the routine is fixed at a particular template, the process identifies matches and mismatches among the haplotype strings (block 511) and merges match segments for the various templates (block 513). Operation 511 identifies matches only if the current haplotype site is unmasked in the current template. Assuming that the current site is unmasked, operation 511 may be implemented in various ways such as by updating positional prefix and divergence arrays. Note that each template may have its own match segment information. Using this information, operation 513 may merge currently pending segments (at the current haplotype site) from among the various templates.

Operation 515 serves to iterate over all the templates while the process is fixed at a given haplotype site and operation 517 serves to iterate over all haplotype sites. Ultimately all haplotype sites are considered and the error-corrected IBD segments are completed. See operation 519.

Figure 5B:
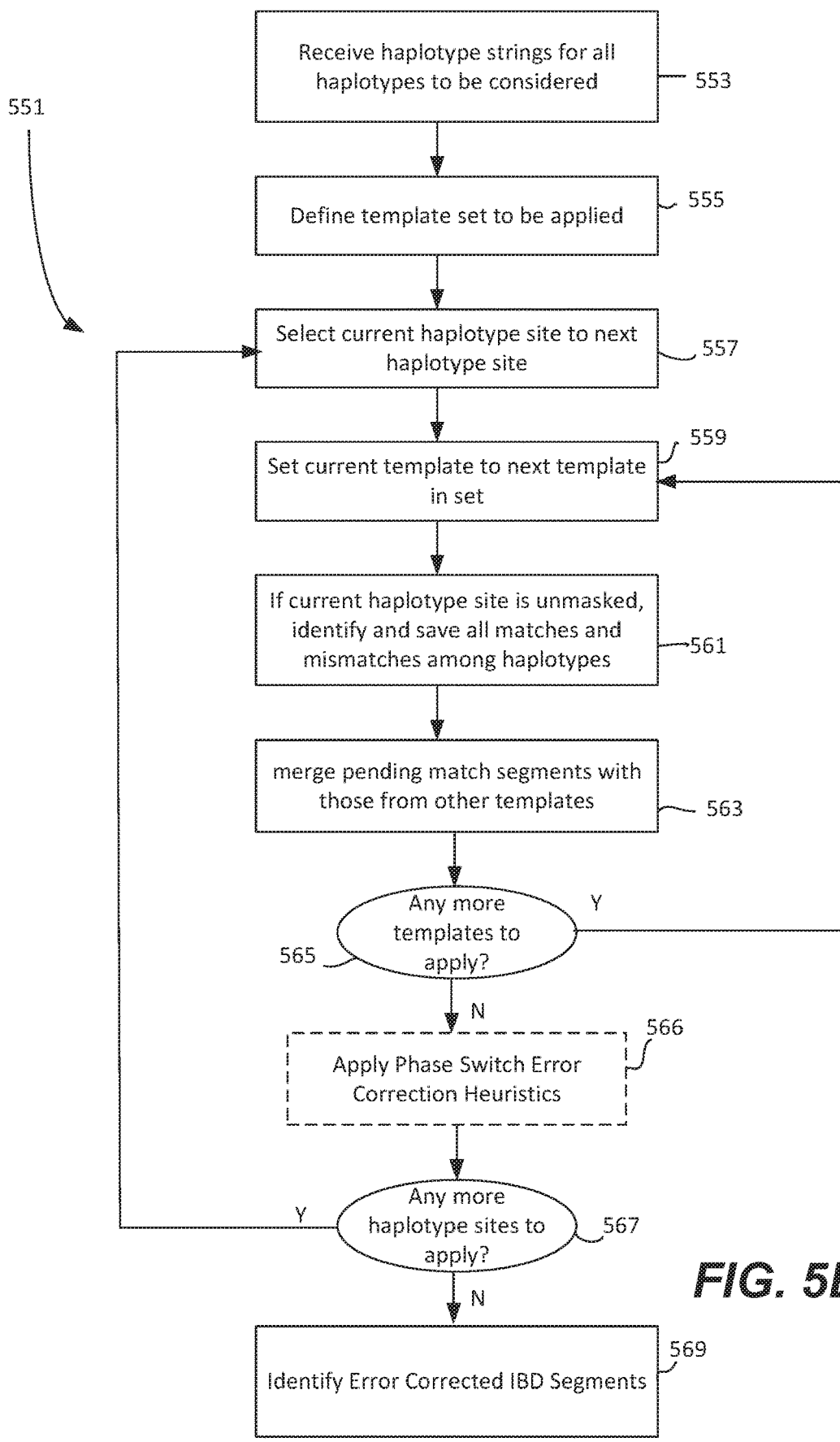

FIG. 5B illustrates another application of templating to an IBD segment finding method. The depicted process 551 begins by receiving data and set up parameters for the routine. This may involve receiving phased haplotypes (block 553) to be used in the templated matching routine, defining templates to apply (block 555), and setting up any needed matrices and arrays such as a positional prefix array and a divergence array.

The depicted process loops over the various sites of the haplotypes, and at each site it loops over the available templates. This is depicted in the figure as follows. The process increments to the next haplotype site (the current haplotype site) at an operation 557, and while at the current site, it iterates over the various templates, starting by incrementing to the next template at an operation 559. While the routine is fixed at a particular template, the process identifies matches and mismatches among the haplotype strings (block 561) and merges match segments for the various templates (block 563). An operation 561 identifies matches only if the current haplotype site is unmasked in the current template. Assuming that the current site is unmasked, operation 561 may be implemented in various ways such as by updating positional prefix and divergence arrays. Note that each template may have its own match segment information. Using this information, operation 563 may merge currently pending segments (at the current haplotype site) from among the various templates. Operation 565 serves to iterate over all the templates while the process is fixed at a given haplotype site.

An optional operation 566 identifies and addresses phase switch errors at the current haplotype position. As indicated, in some embodiments, phase switch errors may be addressed using a heuristic that recognizes typical phase switch errors.

An operation 567 serves to iterate over all haplotype sites. If any of the templates indicates a continuous sequence of matching sites including the current site or sites adjacent to the current site, the match sequence is deemed to continue, even if one or more of the templates indicates a gap in the match sequence. Ultimately all haplotype sites are considered and the error-corrected IBD segments are completed. See operation 569.

While processes 501 and 551 are implemented in a manner in which all templates are considered at one site before incrementing to the next site, the templating process need not be implemented in this manner. A different approach considers all sites for one template, saves that template's putative IBD segments, considers all sites for a second template, saves that template's putative IBD segments, and so on until all templates are considered. The resulting putative, template-specific IBD segments may then be merged.

Merging may involve aligning the putative IBD segments from each templated result, and then scanning through the template-specific segments for pairs of haplotypes. During this process, as long as one of the six templates (or however many are used) still shows a continuing segment, the method keeps a merged IBD segment intact.

In various embodiments, the methods assume that any IBD start or end points within an otherwise continuous IBD segment are caused by errors. This is a reasonable assumption because the comparison is made between two individuals. There is a very low probability that two haplotypes will match, for greater than a threshold length, by chance.

In some embodiments, an additional filtering operation to remove some putative IBD segments is performed after one of the above-described processes such as process 301 or process 501. For example, the filter may operate by discarding putative IBD segments of size below three centimorgans.

To help illustrate the range of implementations, the following example description of templated PBWT is provided. Given M haplotypes with N bi-allelic sites, the PBWT algorithm can identify identical subsequences of the haplotypes in O(NM) time. A limitation of PBWT is that it requires exact subsequence matches with no errors or missing data. To reduce sensitivity to error and missing data, a templated PBWT may be used. A templated PBWT may be designed or configured to identify matching subsequences of the haplotypes despite missing data and genotyping errors with only a small linear increase in computational time compared to the PBWT.

One approach for extending PBWT to report matching haplotypes that include some errors involves constructing multiple replicates of the PBWT data structure. Each of these PBWTs is built by masking the haplotype alignment using a different repeating template. Each PBWT may then be individually swept through identifying exact subsequence matches. The matching subsequences from all PBWTs (each from a different template) may then be merged to produce all matching subsequences within the full (unmasked) haplotype alignment.

Many different digital template repeating structures may be used. One example uses different repeating templates: for example ØhØh, hØhØ, ØØhh, hhØØ, ØhhØ, and hØØh, where sites at Ø will be masked out and only sites at h are used to construct the IBD segments using, e.g., PBWT. These example templates address haplotype data with no more than two errors per four site window. The design of these six specific templates guarantees that all matches across any given four site window will be found as long as there are no more than two errors within the window. This is because given any possible arrangement of two errors across four sites in the original haplotype alignment at least one of the PBWT replicates will have those errors masked out and therefore still deliver the match correctly.

This method's sensitivity to errors may be modified by changing the arrangement and number of templates. For example, more templates could be utilized to ensure matches across longer windows; indeed (n/k) templates are required to ensure all matches across windows of size n with no more than k errors per window. In practice genotyping errors are often low enough that six templates would be adequate (templates of length 4 with two sites masked); even with a genotyping error rate as high as 0.001 the probability of three errors within a four site window is $3.996 \times 10^{-9}$. Running each templated PBWT replicate can be easily parallelized.

Templating the PBWT as described above to handle errors and return subsequence matches can be executed in linear time by passing through the data only once and avoiding the need for a post-hoc merging algorithm. In some PBWT implementations, at each position k within the haplotype alignment two arrays are constructed: ppak the positional prefix array and divk the divergence array (Durbin 2014). ppak is a list of the haplotypes sorted so that their reversed prefixes (from k−1 to 0) are ordered. This ordering ensures that haplotypes that match through position k−1 will end up adjacent to one another in ppak. The divergence array divk keeps track of where those matches began, the ith element in divk represents the beginning of the match between the ith element in ppak and the i−1th element in ppak.

In certain embodiments, to create a templated PBWT, the method constructs a separate ppaj,k and divj,k for each template j used at site k. In this approach, a set of templates (as described above) may be formalized as an indicator function T (j, k) with the value 0 when the template j skips over site k and 1 if template j processes site k. As the haplotype alignment is passed through, T (j, k) is called for each template j; if T (j, k) is 1 then ppaj,k and divj,k are assembled accordingly. When a matching subsequence of at least Lm sites terminates at site k under template j the start and end positions of the match are stored in auxiliary data structures Ps and Pe, respectively. Ps and Pe are both M by M two dimensional arrays in which the position x, y holds the start/end positions of the match between haplotype x and haplotype y. If another subsegment has already been stored the routine checks to see if the new matching subsegment overlaps and possibly extends the existing subsegment. If they do not overlap, the routine checks if the old matching segment has a genetic length (in cM) of at least Lf and then reports it. The new matching subsegment is then stored in its place. In this way the "templating" of the haplotype alignment is performed within this modified form of the PBWT itself, and matching subsegments from each template are merged and extended directly as the haplotype alignment is passed through. Depending on the choice of T (j, k), the templated PBWT has a worst-case time complexity of O(NMt) where t represents the number of templates defined within T (j, k); thus the method represents a linear tradeoff between the speed of PBWT and sensitivity to error. However, using the templates described in the paragraphs above the templated PBWT takes time O(NM3) because t=6 and N becomes N/2 since each template only processes 2 out of every 4 positions in the alignment.

An example templated PBWT is further detailed as pseudocode in Algorithm 1. The algorithm employs 2 parameters: (1) Lm is the minimum number of sites that a sub-segment must span within the haplotype alignment to be merged and extend other sub-segments, and (2) Lf is the final minimum length (in cM) that a segment must have to be reported by the algorithm. Notably the algorithm handles missing data by extending the current longest match. At site k the longest matching haplotype to haplotype ppaj,k will be either ppaj−1,k or ppaj+1,k, so if missing data in ppaj,k is encountered it is simply assumed the haplotype continues to extend the longest match. One additional detail is omitted in Algorithm 1 for space considerations; after passing through all sites in the haplotype alignment the routine loops through the haplotypes one last time to report any "trailing" matches (matches that extend all the way through the end of the haplotypes).

Figure 5D:
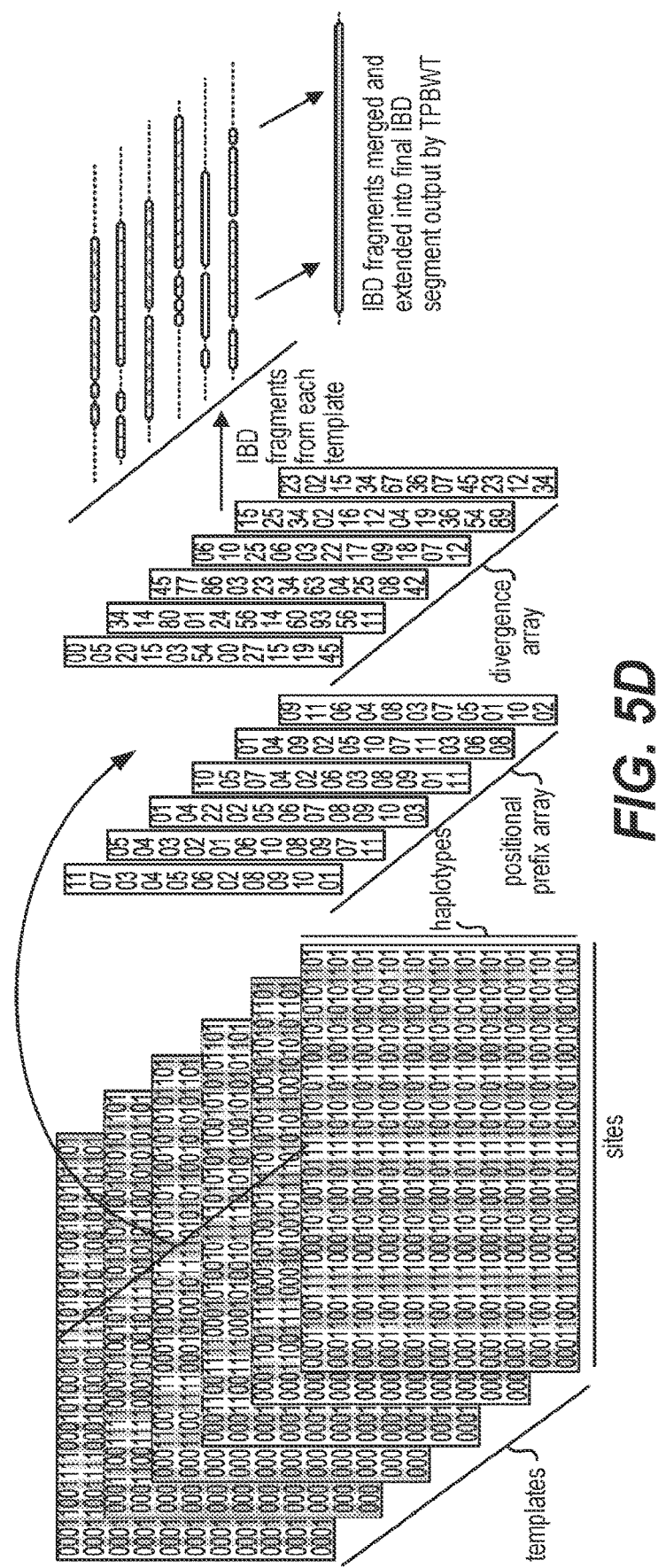
FIG. 5D presents an illustration of the various data structures used in accordance with a Templated PBWT process as described herein.

FIG. 5D illustrates the Templated PBWT data structures. To identify haplotype sharing among a large panel of haplotypes, the TPBWT passes once through an M by N by t three-dimensional structure where M is the number of haplotypes, N is the number of bi-allelic sites, and t is the number of templates. Each template is a pattern at which sites are masked out (shaded out in the figure). During the left-to-right pass through this structure, at each site k, two arrays are updated. The positional prefix array ppa and the divergence array div are both two dimensional arrays of size M by t. At site k, each of the t columns of ppa and div are updated for the templates that are not masked out. Each of the t columns in ppa contains the haplotypes sorted in order of their reversed prefixes. Similarly, each of the t columns in div contains the position at which matches began between haplotypes adjacent to one another in the sorted order of ppa. During the left-to-right pass through this structure, short fragments of IBD shared between haplotypes i and j, broken up by errors, are identified by each of the t templates (green arrows). As these fragments are identified they are merged and extended with one another in the current match arrays $P_s$ and $P_e$. While merging and extending IBD fragments a heuristic may be used to scan for and fix putative phase switch errors, as will be discussed further herein.

Algorithm 1

Templated PBWT algorithm to find matching subsequences. Here t represents the number of templates defined within the templating function T(t, k), N is the number of sites in the haplotype alignment, and M is the number of haplotypes. Additionally $A_{j,k}$ is the allele at position k for haplotype $ppa_{r,j}$. FIG. 5C shows pseudocodes of the algorithm.

Phase Correction Heuristic

As noted above, long IBD segments may be fractured by phase switch errors introduced by phasing techniques used to phase the haplotype data of the individuals. The locations and frequencies of such fractures may occur in predictable ways. In some embodiments a heuristic is employed to correct phase switch errors as IBD segments are identified.

As noted herein in FIG. 5B and operation 566, a heuristic may be applied to identify and correct potential phase switch errors by analysis of sequential haplotype sites. In certain embodiments, a heuristic involves merging adjacent potential IBD segments (matching segments) that end within a threshold distance and then joining or swapping haplotype segments of a given individual, as necessary, to correct phase switch errors. While not wishing to be bound by any particular theory, this heuristic may improve IBD determination because it is biologically unlikely that two IBD segments on the same or opposite haplotypes of an individual both end within a particular distance (e.g., about 500 or fewer SNPs on the same or opposite haplotypes).

In some embodiments, the phase switch heuristic is turned off between closely related pairs of individuals, e.g., between parent and child. For example, if an individual is trio-phased (phasing a child's genotype compared to the parent's genotype), the phasing is considered highly accurate and there are few to no phase switch errors. While the phase switch heuristic is discussed in the context of a Templated PBWT process, the heuristic may be used alone or in conjunction with any of various other algorithms that identify IBD segments for phased haplotype data. Such other algorithms may or may not include analyses that identify and/or correct genotyping and similar errors.

As a new IBD segment is identified, the start position of the new IBD segment is compared to the end position of an adjacent IBD segment. In some cases, the start position of the new IBD segment and the end position of the adjacent IBD segment are on the same haplotype with a gap between them. In some cases, the start position of the new IBD segment and the end position of the adjacent IBD segment are on opposing haplotypes with either a gap between them or an overlap.

If the length of the gap or overlap between adjacent IBD segments is within a threshold value, then the two IBD segments may be merged to form a single IBD segment. In some embodiments, the threshold value is between about 0-500 SNPs, about 0-300 SNPs, about 200-300 SNPs, or about 0-100 SNPs. In some embodiments, the threshold value for merging adjacent IBD segments is the same threshold value for determining that two haplotypes have a minimum number of sites that a sub-segment spans to be considered a potential IBD segment (Lm). If the two IBD segments are on opposite haplotypes, portions of the haplotypes (i.e., haplotype segments) may be swapped starting at the location of a break in the IBD segments. Thus, as the process proceeds to the next haplotype site and beyond, the haplotypes remain swapped unless/until the heuristic determines another phase switch error has occurred and swaps the haplotypes. As the Templated PBWT continues along the chromosome sites, the haplotypes used to identify potential IBD segments remain swapped. In effect, in some embodiments the heuristic is used to correct the actual haplotypes for phase switch errors in addition to correcting IBD segments.

In some implementations, the merged potential IBD segment must have a minimum length Lf to be deemed an IBD segment. Of course, a merged segment that does not initially qualify as an IBD segment may grow to a length required to be an IBD segment.

Figure 6A:
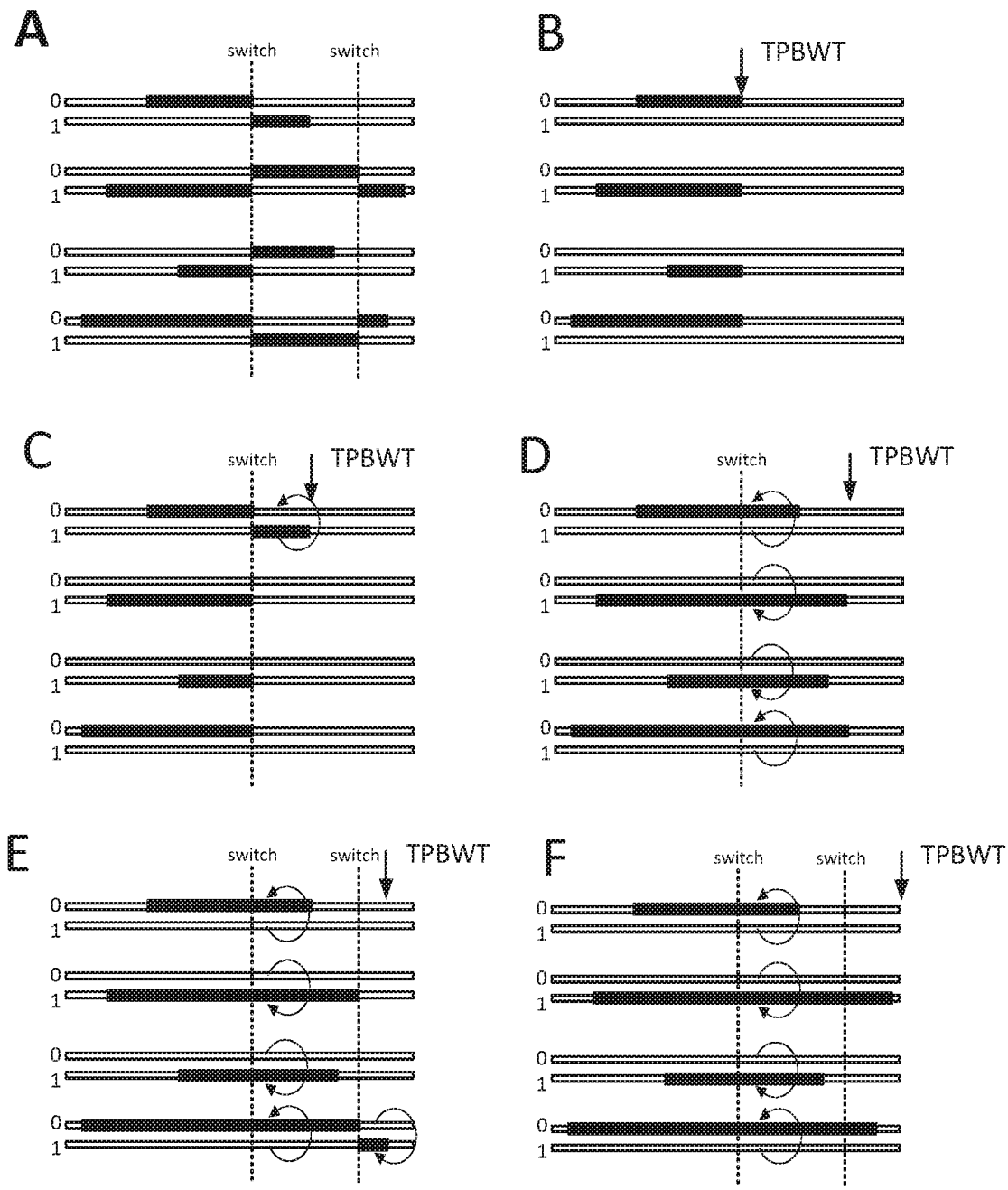
FIGS. 6A and 6C present process flows for a phase switch error correction heuristic according to various embodiments herein.

FIG. 6A illustrates via a series of diagrams how the heuristic may be applied for four individuals that share IBD segments with a focal person. Each pair of haplotypes (0 and 1; dotted lines) represents a copy of the haplotypes of the focal person, while the grey bars represent the IBD segments the focal person shares with four other individuals. In other words, the top pair of haplotypes shows IBD segments of the focal person and another individual, the second pair of haplotypes shows IBD segments of the same focal person but with a second other individual, and so on. While a focal person is provided for purposes of illustrating the heuristic, in some embodiments the heuristic is applied to correct phase switch errors in multiple or all individuals simultaneously. In such embodiments, there may not be a focal person, per se. However, to simplify illustration of such embodiments, correcting phase switch errors may be presented with reference to a "focal" individual. In some embodiments, the process is implemented using one or more focal individuals. For example, a focal person may be a new user or customer that is added to the database of, e.g., a person genetics platform. In some implementations, the process runs using the new user or customer as the focal individual against the entire database.

Panels B through F represent the TPBWT's sweep along the chromosome from left to right, with the black arrow labeled TPBWT representing the current position. As the TPBWT sweeps along the haplotypes identifying IBD matches it uses a heuristic to identify and fix putative phase switch errors. In diagram A, two haplotypes (0 and 1; dotted lines) of the focal person and the IBD segments they share with the four other individuals in the haplotype alignment are plotted. The focal person has two phase switch errors (red dashed lines) that break up long IBD segments. In diagram B, the Templated PBWT scans left to right along the chromosome, keeping track of IBD segments shared among all pairs of individuals. When a phase switch error is encountered in the focal person all IBD segments shared with the focal person are fragmented at the position of the switch error. In diagram C, the Templated PBWT continues to scan left to right and finds another IBD segment. If the new segment begins near the end of all the old segments but on the complementary haplotype of the focal person, then the Templated PBWT infers a phase switch error to have occurred. In diagram D, since a phase switch error is inferred within the focal person, the focal person's haplotypes are now swapped (at or near the point of the phase switch error) so new IBD segments now merge and extend the fragments on the complementary haplotype that were broken up by the phase switch error. If instead the phase switch error is inferred within one of the other individuals, then that other individual's haplotypes are swapped, and the focal person's haplotypes remain unswitched. In diagram E, when the arrangement of IBD segments on the complementary haplotypes again suggests another phase switch error has been encountered the algorithm swaps the focal person's haplotypes again, but this time at the location of the other phase switch error. In diagram F, the Templated PBWT continues to the end of haplotypes after successfully identifying phase switch errors and "stitching" IBD fragments back into correct long IBD segments.

In some embodiments, the heuristic is applied to correct phase switch errors when a new potential IBD segment is identified. As described above, a potential IBD segment is identified when the Templated PBWT reaches the rightmost end of the potential IBD segment. For example, in diagrams C and E only a single new potential IBD segment is identified because the TPBWT has not reached the end of the other IBD segments, triggering their identification as potential IBD segments and application of the heuristic. To illustrate this point, note that in panel E the rightmost fragment in the second from top haplotype pair has not yet been identified since the TPBWT operation has not reached the fragment's rightmost end. However, by panel F, the TPBWT has scanned further right along the chromosome and identified that fragment and applied the heuristic to it (which merged it into the long IBD segment).

As may be appreciated by FIG. 5B, the heuristic is applied as the Templated PWBT iterates through successive sites along all chromosomes. As potential IBD segments are identified, the proximity of the identified IBD segment to a prior IBD segment on either haplotype is determined to infer whether there is a phase switch error and the IBD segments should be 'stitched' together to form a single IBD segment.

Figure 6B:
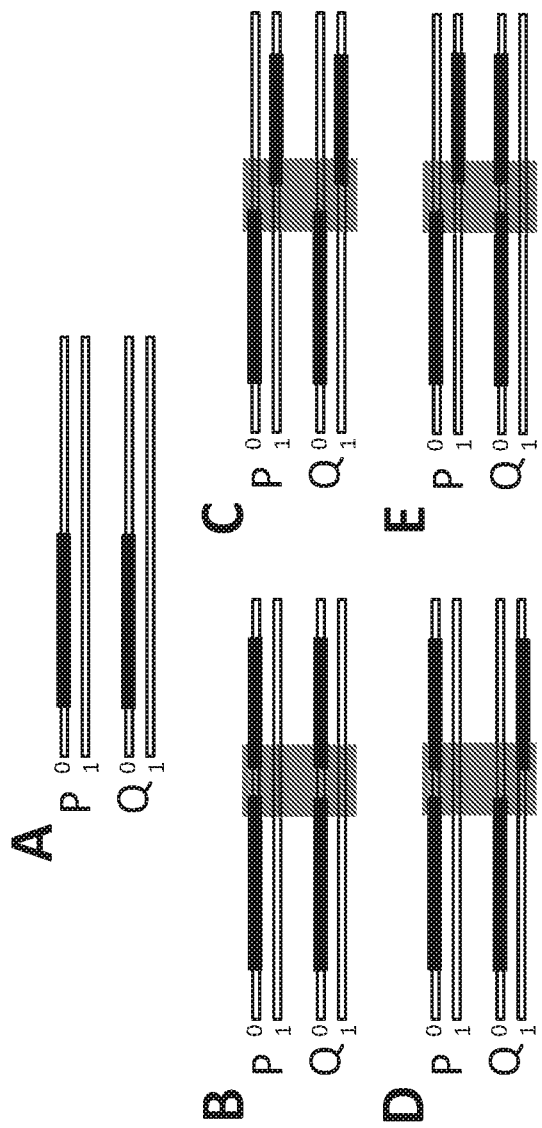
FIG. 6B presents various types of phase switch errors that may occur between two pairs of haplotypes.

FIG. 6B illustrates the possible scenarios considered by the Templated PBWT for adjacent IBD segments. Diagram A shows a first IBD segment shared by P and Q. Diagrams B-E show the various combinations of second IBD segments between P and Q that may be considered by the heuristic (the grey box indicates the two potential IBD segments are within a threshold length of each other). The second IBD segments are within a threshold number of SNPs of the first IBD segments. In Diagram B, all IBD segments are on the same haplotype, but are separated by a gap. This may result from an even number of phase switch errors, causing the haplotypes to be swapped at both ends of the gap such that the potential IBD segments are on the same haplotype. It should also be understood that the exact number of phase switch errors within the gap may be unknown and is not necessary to infer which individual harbors the phase switch error(s). For example, in Diagram B phase switch errors may have occurred in P, Q, or P and Q, and the heuristic may be applied as a result of two potential IBD segments being identified within a threshold range of each other, as discussed herein.

It should be also be understood that while the Templated PBWT may be used to correct for short gaps, e.g., 1-3 SNPs, the gap illustrated here may be larger, for example up to about 100 SNPs, or about 300 SNPs, or about 500 SNPs. This may be caused by various errors, including multiple phase switch errors within the gap, such that the matching sites are insufficiently long to be considered potential IBD segments. The heuristic as described herein infers that two segments within the threshold distance are likely to be a single segment broken up by errors, and thus merges them despite the gap.

Diagram C illustrates the second IBD segments being on opposite haplotypes for both P and Q, which may be the result of a phase switch error in both individuals. In such cases, the haplotypes may be swapped in both individuals. Diagrams D and E illustrate either Q or P, respectively, having second IBD segments on the opposite haplotype. In these scenarios, if the second IBD segments are within a threshold distance of the first IBD segments but on the opposite haplotype, a phase switch error is inferred and the haplotypes from the second IBD segments forward may be swapped and the first and second IBD merged. In cases D and E, the individuals having the first and second IBD segments on opposite haplotypes are the ones inferred to have the phase switch error, and only those individuals' haplotypes are swapped. The swaps begin at the points on or near where the breaks between the first and second IBD segments occur.

As described above, the Templated PBWT handles haplotype error (miscalls) and missing data. It is also robust to "blip" phase switch errors in which the phase at a single site is swapped. However, phase switch errors spaced out along the chromosome will cause long regions of the haplotypes to be swapped and fragment IBD segments as illustrated in FIG. 1. To handle these errors the Templated PBWT may apply a phase correction heuristic that scans for certain patterns of haplotype sharing to identify and correct phase switch errors. Note that for haploid data sets such as human male sex chromosomes this heuristic can be turned off. Large cohorts of samples have patterns of haplotype sharing that are highly informative regarding the location of phase switch errors. The phase switch errors in an individual will fragment all IBD segments shared with that individual at the position of the switch error. Each IBD segment that spans the switch error will be broken into two fragments at the position of the error: these fragments will be on complementary haplotypes within the individual with the error and yet may remain on the same haplotype within the other individual. For some closely related pairs (parent-child) this pattern of haplotype sharing may be the result of actual recombination patterns, however for the majority of more distantly related individuals the pattern can be used to identify phase switch errors.

Figure 6C:
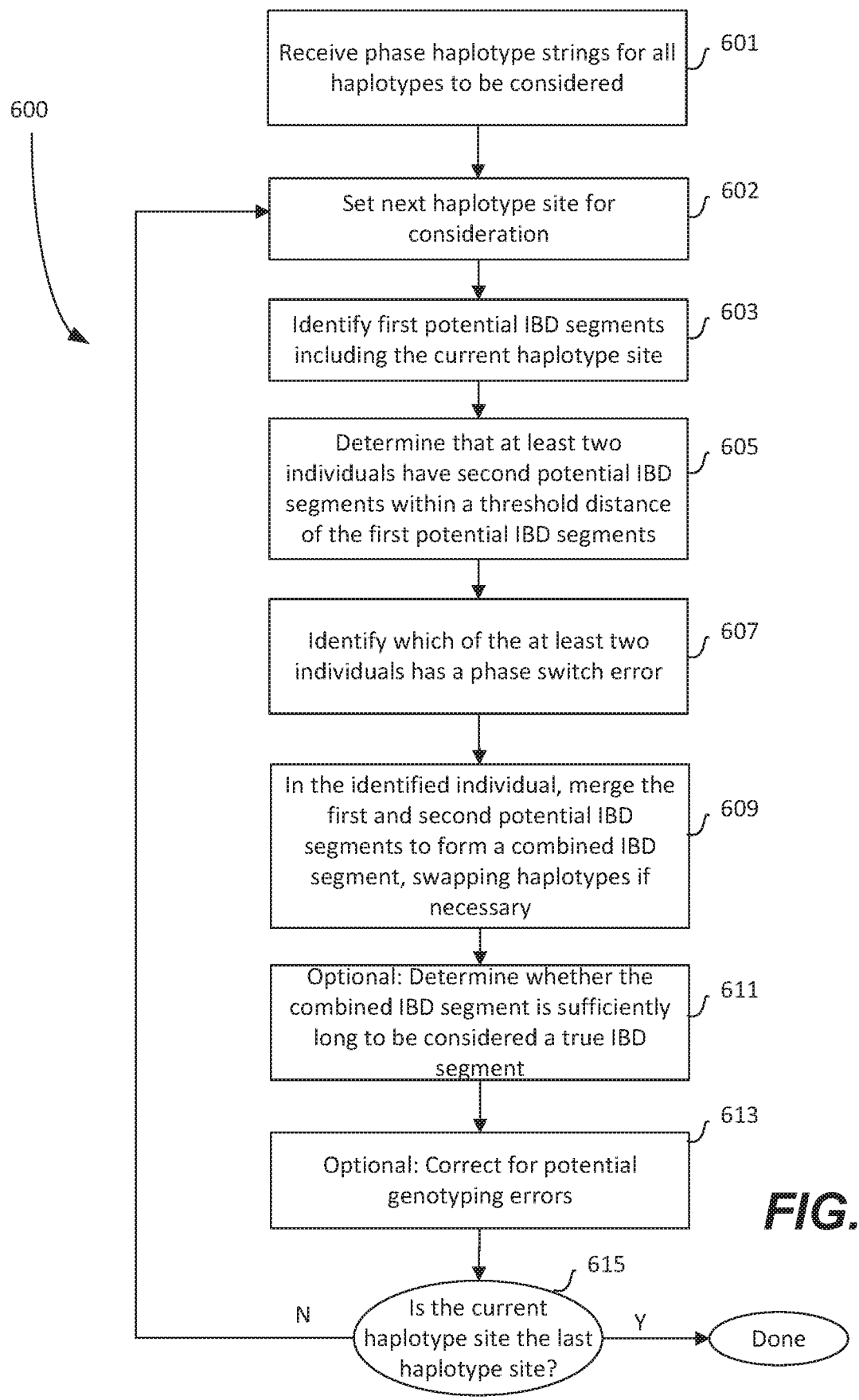

As the TPBWT scans left to right through the haplotype alignment finding new IBD segments it keeps track of previously found IBD segments shared among pairs of haplotypes in $P_s$ and $P_e$. When a new segment shared between two individuals P and Q is found to be adjacent to an existing segment (either slightly overlapping or with a small gap between them; determined by the parameter Lm) there are a number of possible scenarios (FIG. 6C). If the new segment is on the same haplotypes as the existing segment, then possibly the two segments are fragments of a longer segment broken up by error and should be merged. If the new segment begins near the end of the existing segment and the new segment is not on the same haplotypes as the old segment, then possibly there was a phase switch error in both individuals. If the new segment begins near the end of the existing segment and the new segment is on the same haplotype as the existing segment in individual P but on the complementary haplotypes in individual Q, then possibly there was a phase switch error in individual Q. And of course, the opposite pattern could exist suggesting a phase switch error in individual P. If a phase switch error has been identified in either individual P, Q, or both, then the TPBWT will swap the haplotypes for the individuals containing the error (See FIG. 6B). Now the new IBD segments merge and extend the fragments on the complementary haplotype that were broken up by the phase switch error. When the arrangement of IBD segments on the complementary haplotypes again suggests another phase switch error has been encountered the algorithm stops swapping the individual's haplotypes. This simple heuristic continues to the end of haplotypes "stitching" short stretches of IBD fragmented by errors back into the correct long IBD segments.

FIG. 6C illustrates a process for using a phase switching error correction heuristic as described herein. The process 600 begins at operation 601 by receiving haplotype data for a plurality of individuals. The process 600 may be performed while scanning the haplotype data using a method such as a Templated PBWT (e.g., during operation 566 in FIG. 5B) or may be performed as a standalone process. The process begins by receiving phased haplotype data to be considered. The process loops over multiple haplotype sites, considering each one separately, but also considering adjacent and/or near sites that contain IBD segments, particularly nearly terminated IBD segments along with newly started IBD segments. An operation 602 sets the next haplotype site for consideration. In embodiments where this heuristic is integrated with another analysis, e.g., Templated PBWT, this site incrementing operation may already have been performed. An operation 603 determines phased haplotypes of at least two individuals have first potential IBD segments that terminate at a first location. In some embodiments, first potential IBD segments may be identified after a matching subsequence having at least Lm sites terminates. The subsequences must possess more than a threshold length Lm to be considered possible IBD segments. The first potential IBD segments terminate at a first location which may be stored for later reference.

An operation 605 determines that the at least two individuals have second IBD segments that start at a second location within a threshold distance of where the first IBD segment ended. The threshold distance may be as described above. In some implementations, the distance may be either a gap or an overlap between the first and second potential IBD segments.

An operation 607 identifies or infers which individual, from among those having second IBD segments that starts at a location within the threshold distance of where the first IBD segment ended, likely has a phase switch error. The second potential IBD segments may be between any combination of haplotypes of the at least two individuals. See FIG. 6B. When the second potential IBD segment begins on the opposite haplotype as the first potential IBD segment in at least one of the individuals, a phase switch error is implied in the individual that has the first and second IBD segments on opposite haplotypes. In various embodiments, where two fragments of a fragmented IBD segment occur on opposite haplotype strings of single individual, the operation infers that that individual has the phase switch error, and only that individual's haplotypes need correction for the phase switch error. In cases where both individuals sharing an IBD segment have IBD fragments on opposite haplotype strings, the operation may infer that both individuals have phase switch errors at the same or proximate positions. In some cases operation 607 may be skipped. For example, as shown in diagram B of FIG. 6B, above, the potential IBD segments to be merged are on the same haplotype. In such embodiments it may be difficult to determine which individual had a phase switch error and also unnecessary to properly merge the potential IBD segments (as swapping the haplotypes is not necessary to have the potential IBD segments on the same haplotype).

In operation 609, based on the first potential IBD segments and the second potential IBD segments being within the threshold distance of each other, the first potential IBD segments and the second potential IBD segments are merged. If the first potential IBD segments and the second potential IBD segments are on opposite haplotypes for any of the at least two individuals (i.e., a phase switch error occurred for those individuals), the haplotypes may be swapped for those individuals. The swap may occur at the location of the phase switch error.

Operation 611 is an optional operation to determine whether each potential IBD segment is sufficiently long and/or meets other criteria to be considered a true IBD (e.g., a minimum length Lf). If the criteria are met, the potential IBD segments are determined to be actual IBD segments.

Operation 613 is an optional operation to correct for potential genotyping errors. See e.g., the discussion of the Templated PBWT.

In block 615 the current haplotype site is checked for whether it is the last haplotype site. If it is the last haplotype site, the process finishes. If it is not the last haplotype site, the process returns to operation 602 to select the next haplotype site and continue scanning for IBD segments. In some embodiments where process 600 is part of another method to identify IBD segments, e.g., a Templated PBWT, the loop may also allow for the Templated PBWT algorithm to continue scanning the next haplotype site.

Error Correction Using Hidden Markov Model (HMM)

Description and Application of HMM

Figure 7:
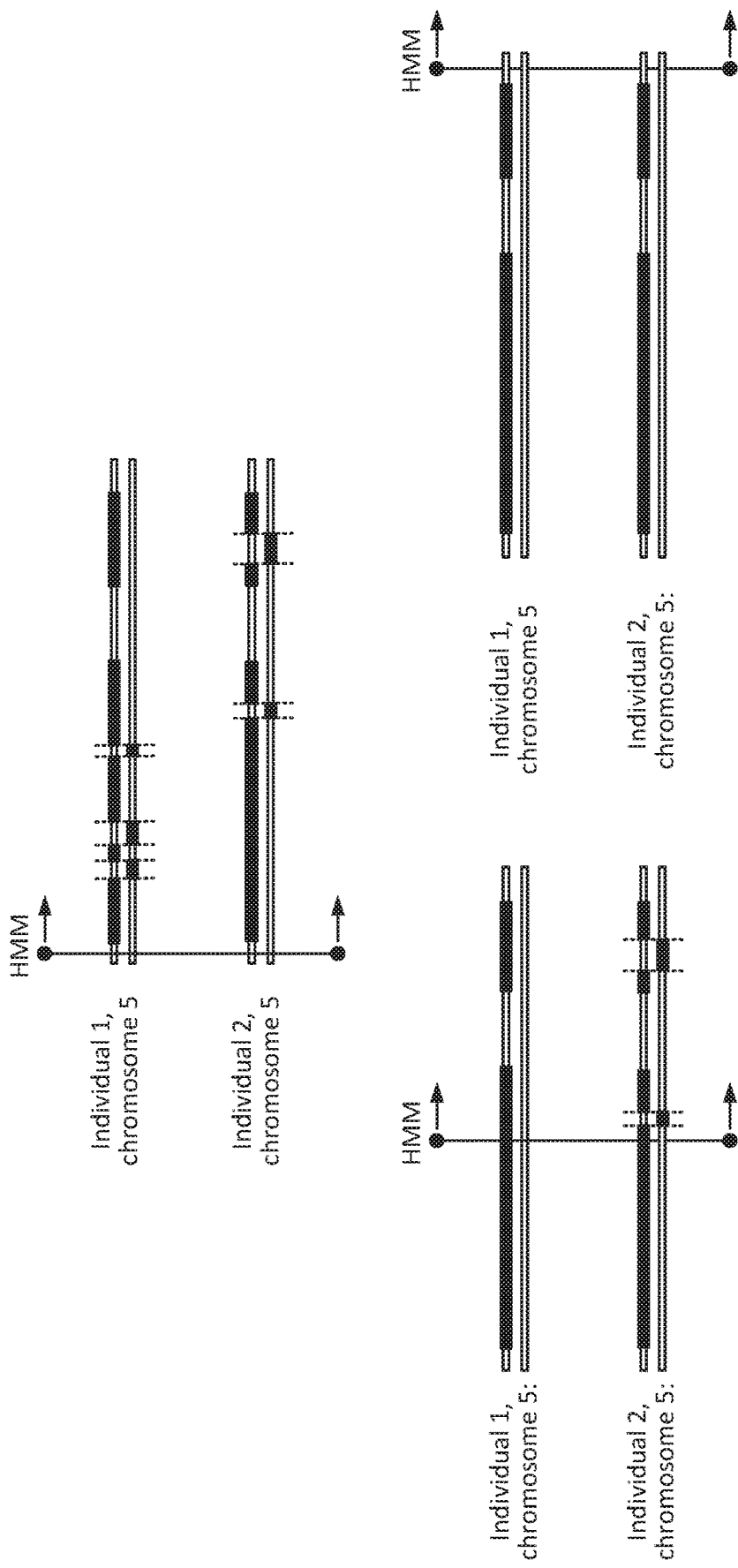
FIG. 7 illustrates using a HMM to process four haplotypes of two individuals to correct phase switch errors.

As shown in FIG. 1, long IBD segments are likely fractured by phase switch errors introduced by phasing techniques used to phase the haplotype data of the individuals. FIG. 7 schematically illustrates using a HMM to process four haplotypes of two individuals (individual 1 and individual 2, two haplotypes for each individual on chromosome 5) to correct phase switch errors, "stitching" IBD segments fractured by phase switch errors. The HMM process covers the full span of the four haplotypes from left to right shown sequentially in the top panel, lower left panel, and lower right panel.

Figure 8:
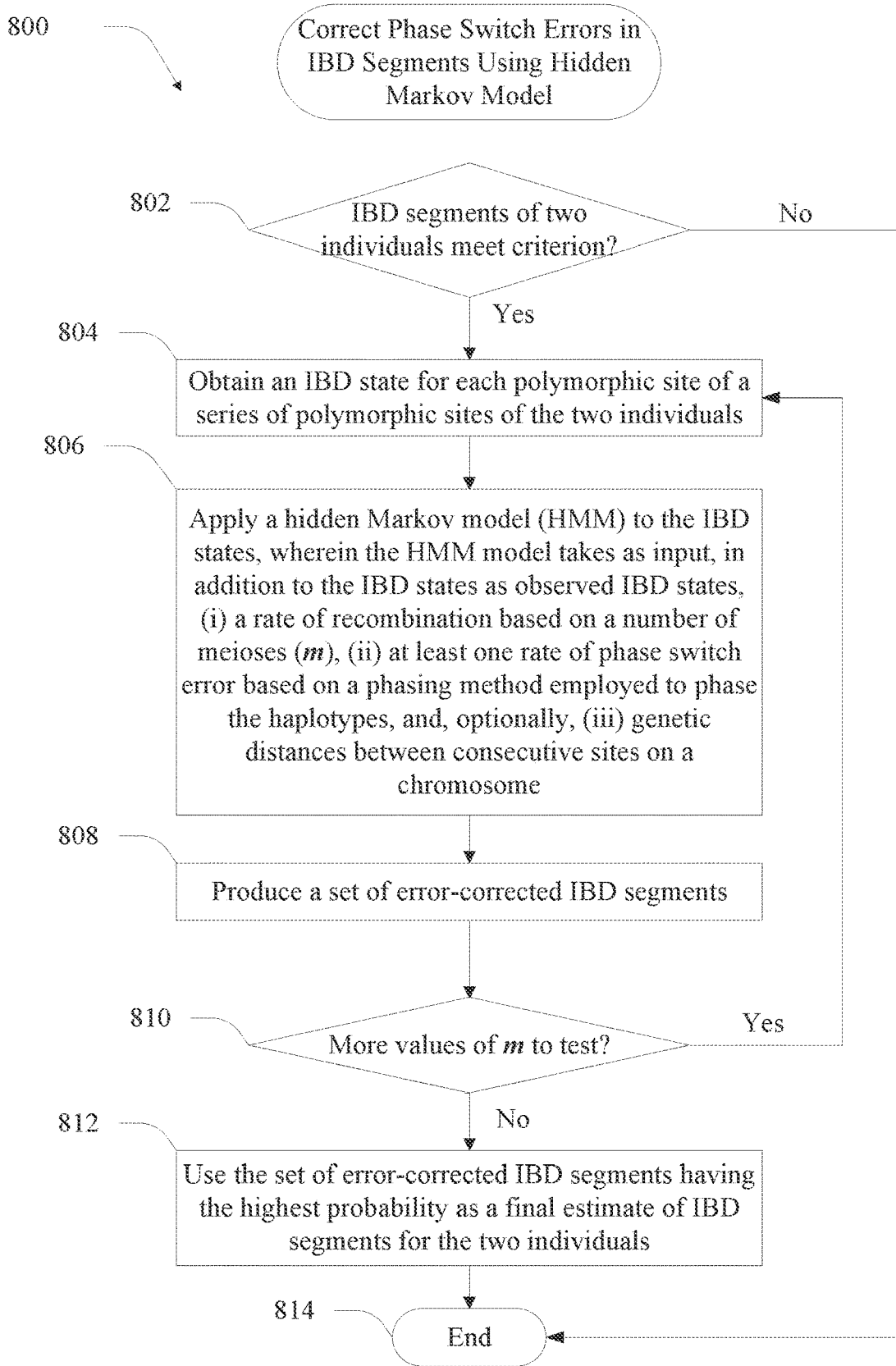
FIG. 8 presents a flow diagram for correcting phase switch errors in IBD segments using a HMM according to various embodiments.

FIG. 8 shows a flow diagram illustrating process 800 for correcting phase switch errors in IBD segments using a hidden Markov model (HMM) according to some implementations. In some implementations, the error correction optionally is initiated or triggered when IBD segments of the two individuals being compared meet one or more criteria. See decision box 802. This conditional trigger can avoid processing IBD segments that may not need corrections. In some implementations, for example, the HMM error correction process is triggered when the two individuals' IBD segments include two or more IBD segments on a single chromosome. This can avoid applying error correction when there is only a single IBD segment on a single chromosome where no phase switch errors have occurred. In some implementations, the criterion is met when the two individuals' IBD segments exceed a minimum total amount of shared IBD.

In these implementations, if the IBD segments of two individuals do not meet the criterion or criteria, the process ends. See box 802, "No" branch, and box 814. If the IBD segments of the two individuals meet the criterion or criteria, process 800 proceeds to obtain an IBD state for each polymorphic site of a series of polymorphic sites of the two individuals. See the box 802, "Yes" branch and box 804. The IBD state indicates whether alleles of the two individuals at the polymorphic site are part of an IBD segment, and if so, which of the two individuals' phased haplotypes are part of the IBD segment. The series of polymorphic sites are located in one or more pairs of chromosomes of each individual. In some implementations, the polymorphic sites are biallelic sites. In other implementations, more than two alleles may be implemented at a site. In some implementations, the IBD states indicate different conditions of zero IBD, half IBD, and full IBD. In some implementations when the polymorphic site is a biallelic site, the IBD states include nine different IBD states corresponding to nine conditions of zero IBD, half IBD, and full IBD as further described in examples hereinafter.

Process 800 then involves applying the HMM to the IBD states. Box 806. The HMM model takes the IBD states as inputs and uses them as observed states of the model. The HMM model also takes as input (i) a rate of recombination based on a number of meioses (m), (ii) at least one rate of phase switch error based on a phasing method employed to phase the haplotypes, and, optionally, (iii) genetic distances between consecutive sites on a chromosome. In some implementations, genetic distances between consecutive sites on a chromosome may be omitted. The term "model input" herein refers to both variables and parameters. The HMM model's transmission rates or probabilities depend on (i) and (ii), and optionally (iii). The application of the HMM model removes likely phase switch errors and produces error corrected IBD segments based on a most likely sequence of hidden IBD states given the observed IBD states. See block 808. Applying the HMM involves using transition probabilities and emission probabilities of the HMM to identify the most likely sequence of hidden IBD states given the observed IBD states. In some implementations, the most likely sequence of hidden IBD states is identified using the Viterbi dynamic programming process.

Process 800 is implemented using a computer. It is not practical or feasible to apply the model without a computer due to the complexity of the model. For example, applying the HMM requires using a 36×36 transmission matrix and a 36×36 emission matrix for each polymorphic site, often at hundreds of thousands of polymorphic site, to calculate a most likely sequence. It can take many years and errors for a person to calculate just a single Viterbi sequence.

In some implementations, the error correction process involves only the operations illustrated in boxes 804, 806, and 808. Such implementations include: (a) for each polymorphic site in a series of polymorphic sites of two individuals, obtaining an IBD state that indicates whether alleles of the two individuals at the polymorphic site are part of an IBD segment, and, if so, which of the two individuals' phased haplotypes are part of the IBD segment, wherein the series of polymorphic sites are comprised in or lie along one or more pairs of chromosomes; and (b) applying a hidden Markov model (HMM) to the IBD states to produce one or more error-corrected IBD segments, wherein the HMM model takes as input, in addition to the IBD states as observed IBD states, (i) a rate of recombination based on a number of meioses, (ii) at least one rate of phase switch error based on a phasing method employed to phase the haplotypes, and (iii) genetic distances between consecutive sites on a chromosome. In some implementations, genetic distances between consecutive sites on a chromosome may be omitted.

Some implementations of the disclosure include multiple iterations of applying the HMM to test different numbers of meioses (m). As illustrated in FIG. 8, process 800 determines whether there are additional values of m that need to be tested. If so, the process loops back to box 804 to obtain IBD states and apply the HMM using a different value of m. In some implementations, the different numbers of meioses are in the range from 0.1 to 14 crossovers. In some implementations, the values of m are in the range from 1 to 14. See block 810, "Yes" branch. If there are no additional values of m to be tested, process 800 proceeds to use the set of error corrected IBD segments having the highest probability as a final estimate of IBD segments for the two individuals. See decision block 810, "No" branch, and block 812. Thereafter, process 800 ends at block 814.

In some implementations, m is fixed at 1, requiring no multiple iterations. In other implementations, m=1 provides the set of error corrected IBD segments with the highest probability among multiple values of m.

Figure 9A:
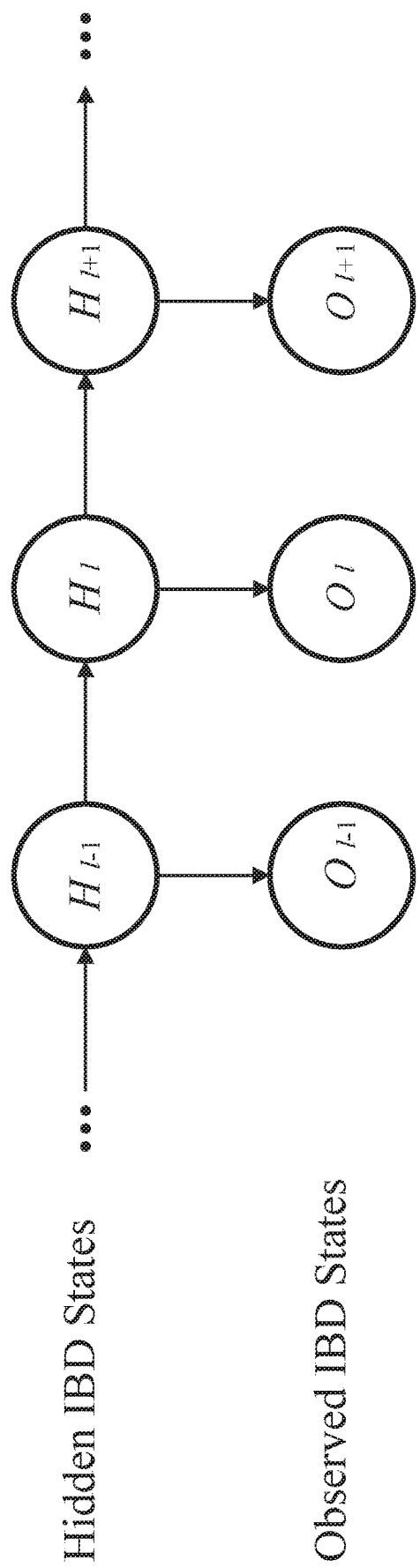
FIG. 9A illustrates the structure of an example HMM model.

FIG. 9A schematically illustrates the structure of the HMM model. It includes a series of hidden states (illustrated as circles on top) representing the ground-truth IBD states at a series of polymorphic sites and a series of observed states (illustrated as circles at the bottom) representing the observed IBD states based on phased haplotype data of the two individuals. The arrows in the diagram denote conditional dependencies. The hidden states obey the Markov property, such that the hidden state at any site depends on only the hidden state at the immediately previous site. In other words, $H_t$ depends only on $H_{t-1}$. Moreover, the observed state at a particular site depends only on the hidden state at the particular site. In other words, $O_\iota$ depends on only $H_\iota$.

In the standard type of hidden Markov model considered here, the state space of the hidden variable is discrete. The parameters of a HMM are of two types, transition probabilities and emission probabilities. The transition probabilities between site l–1 and site ι determine the probability of $H_\iota$ given $H_{\iota-1}$. The emission probabilities at site ι determine the probability of $O_\iota$ given $H_\iota$.

The probability of a series of observed states and a series of hidden states is:

$$Pr(H_1,H_2,H_3, \ldots ,O_1,O_2,O_3, \ldots )=Pr(H_1)Pr(O_1|H_1)\\Pr(H_2|H_1)Pr(O_2|H_2)Pr(H_1|H_2)Pr(O_3|H_3) \quad (Eq.\ 1)$$

where probabilities $Pr(O_i|H_i)$ are emission probabilities/parameters, and probabilities $Pr(H_i|H_{i-1})$ are the transition probabilities/parameters.

The hidden state space assumes one of N possible values, modeled as a discrete distribution. For each of the N possible states that a hidden variable at point/can be in, there is a transition probability from this state to each of the N possible states of the hidden variable at point l+1, for a total of $N^2$ transition probabilities. Note that the set of transition probabilities for transitions from any given state must sum to 1. As such, the N×N matrix of transition probabilities is a Markov matrix.

In addition, for each of the N possible states, there is a set of emission probabilities governing the distribution of the observed variable at a particular point given the state of the hidden variable at that point. The size of this set depends on the nature of the observed variable. For example, if the observed variable is discrete with M possible values, governed by a discrete distribution, there will be a total of N×M emission probabilities.

In some implementations, each polymorphic site is biallelic, and the IBD states at any site can include nine different IBD states, indicating nine conditions of zero IBD, half IBD, and full IBD. Considering 4 phased haplotypes for 2 individuals there are 9 different ways site l can be observed as IBD between the two individuals. In some implementations, the IBD state at site ι notated as $c_{*\iota}$ is represented by a string of 4 integers each corresponding to the 4 haplotypes. The first two integers refer to the maternal and paternal haplotypes in individual 0 and the last two integers refer to the maternal and paternal haplotypes in individual 1. When the haplotype at site l is not IBD practitioners represent it as a 0. Therefore, $c_{*\iota}$=0000 indicates that the two individuals at site ι are not IBD, or zero IBD. Accordingly, there are 4 different ways the two individuals could be half IBD: 0101 is when the individuals are IBD through their paternal haplotypes, 1001 is when the individual 0's maternal haplotype is IBD with individual 1's paternal haplotype, 0110 is when the individual 0's paternal haplotype is IBD with individual 1's maternal haplotype, and 1010 is when the individuals are IBD through their maternal haplotypes.

Similarly there are 4 different ways the two individuals could be full IBD: 1212, 2112, 1221, and 2121. According to the model IBD segments follow a Markovian process in which segments begin and end independently. This means that when modeling full IBD practitioners must keep track of the identity of each of the two IBD segments so one cannot simply represent full IBD as 1111.

Of course, other notations may be used to represent the nine different IBD conditions to a similar effect.

In some implementations, the IBD states are expanded by multiplying these different 9 conditions of IBD with four types of phase switch errors. But if one disregards the phase switch error types, there would be 9×9 transition rates between hidden states of two consecutive sites.

In some implementations, transition rates of the HMM are based upon a rate at which IBD segments start. In some implementations, the rate at which IBD segments start is modeled as a function of the number of meioses. See box 706, input (i). In some implementations, the rate at which IBD segments start ($\alpha_s$) is modeled as follows.

$$\alpha_s = \frac{1}{1+(100.0 \times m)} \quad (Eq.\ 2)$$

wherein m is the number of meioses, and the recombination rate is assumed to be 1 crossover per 100 cM.

In some implementations, transition rates of hidden IBD states are based on a rate at which IBD segments end. In some implementations, the rate at which IBD segments end is modeled as a function of the number of meioses. In some implementations, the rate at which IBD segments ends ($\alpha_e$) is modeled as follows.

$$\alpha_e = \frac{m}{100.0} \quad (Eq.\ 3)$$

wherein m is the number of meioses.

In some implementations, the IBD states include nine different IBD states, and transition rates are based on a transition matrix $Q_\alpha$ in FIG. 9B. In matrix $Q_\alpha$, each row includes rates for transitioning from the IBD state denoted by the four-letter string at site/to nine IBD states at ι+1.

In some implementations, the transition rates of hidden IBD states are weighted by a probability that full IBD between the two individuals is truly present. In some implementations, the probability that the full IBD between the two individuals is truly present is modeled as a logistic function of an amount of estimated full IBD. In some implementations, the probability that full IBD between the two individuals is truly present (β) is modeled as follows.

$$\beta = \frac{1}{1+e^{\eta(0.125-\iota_2)}} \quad (Eq.\ 4)$$

wherein $\iota_2$ is the amount of estimated full IBD, and η is an empirical parameter defining the steepness of the logistic function.

In some implementations, the transition rates of hidden IBD states are weighted by weighting transitions into full IBD states with β, and waiting transitions out of full IBD states with 1/β. In some implementations, the IBD states include nine different IBD states, and the transition rates of hidden IBD states are based on a transition matrix as follows.

$$Q_{\beta_{ij}} = \begin{cases} Q_{\alpha_{ij}} \times \beta, & \text{if } i \le 5 \text{ and } j > 5 \\ Q_{\alpha_{ij}} \times \frac{1}{\beta}, & \text{if } i > 5 \text{ and } j \le 5 \\ Q_{\alpha_{ij}}, & \text{otherwise} \end{cases} \quad (Eq.\ 5)$$

In some implementations, the transition rates of hidden IBD states are based on the at least one rate of phase switch error. See block 706, model input (ii). In some implementations, there are four types of phase switch errors in the two individuals: no switch error in either individual, switch error in individual 0, switch error in individual 1, and switch error in both individuals. The IBD states include nine different IBD states as described herein. The at least one rate of phase switch error includes a rate of phase switch error for each of the two individuals, $\mu_1$ and $\beta2$, respectively. In some implementations, the phase switch error rates for the two individuals are the same when the same phasing method is used for both individuals. In some implementations, the transition rates are based on the 36×36 transition matrix described as follows.

$$Q = \begin{bmatrix} \text{no switch} \\ \text{switch in 0} \\ \text{switch in 1} \\ \text{switch in both} \end{bmatrix} \begin{bmatrix} Q_\beta & \mu_0 Q_\beta & \mu_1 Q_\beta & \mu_0 \mu_1 Q_\beta \\ \mu_0 Q_\beta & Q_\beta & \mu_0 \mu_1 Q_\beta & \mu_1 Q_\beta \\ \mu_1 Q_\beta & \mu_0 \mu_1 Q_\beta & Q_\beta & \mu_0 Q_\beta \\ \mu_0 \mu_1 Q_\beta & \mu_1 Q_\beta & \mu_0 Q_\beta & Q_\beta \end{bmatrix} \quad \text{(Eq. 6)}$$

In some implementations, transition probabilities of hidden IBD states are based upon genetic distances between consecutive sites on a chromosome. See box 706, model input (iii). In some implementations, transition probabilities of hidden IBD states are obtained by exponentiating a transition matrix. In some implementations, transition probabilities of hidden IBD states $Y_{\iota+1}$ given hidden IBD states $Y_\iota$ are modeled as:

$$P(Y_{\iota+1}|Y_\iota, m, \mu_0, \mu_1, l_2) = e^{Q d_\iota} \quad \text{(Eq. 7)}$$

where m is the number of meioses, $\mu_0$ is a phase switch error rate for a first individual of the two individuals, $\mu_1$ is a phase switch error rate for a second individual of the two individuals, $\iota_2$ is an amount of estimated full IBD, Q is a transition matrix described by Eq. 6, and $d_\iota$ is the genetic distances between sites $\iota$ and $\iota+1$.

In some implementations, the emission probabilities of the HMM are dependent on phase switch errors. In some implementations, the emission probabilities are defined by a uniform error term that weights probabilities of observed IBD states based on the four different ways the two individuals may be in phase switch errors.

Example HMM Implementation

To help illustrate the range of implementations, the following example description of using HMM to determine IBD segments, correcting phase switch error is provided. Under the model, IBD segments shared between two related individuals are generated by passing along the four haplotypes of the two individuals. IBD segments begin and end following a Poisson process with rates that are determined by the number of meioses m that occurred on the pedigree between the two individuals. Phase switch errors occur following a Poisson process with a rate p determined by empirically testing statistical phasing methods.

Let $c_\iota = \{c_{*1}, \ldots, c_{*L}\}$ be the L sites observed along a chromosome. Practitioners represent the different ways site $\iota$ can be observed as IBD between the two individuals as $c_{*\iota}$. Additionally, let $\vec{d} = \{d_1, \ldots, d_L\}$ be a vector of genetic distances where the distance between sites $\iota$ and $\iota+1$ is $d_\iota$. Finally, let F be an error term that captures the probability that the IBD state practitioners observed at site $\iota$ is incorrect due to phasing and/or genotyping errors. The conditional probability $P(c_*|m, \mu, \underline{d}, \varepsilon)$ is structured as a hidden Markov model (HMM) with latent variables $\vec{Y} = \{Y_1, \ldots, Y_L\}$. Here $Y_\iota$ represents the different ways site $\iota$ could be observed as IBD plus the different ways the two individuals may be in a phase switch error.

State Space

When considering the 4 phased haplotypes for 2 individuals, there are 9 different ways site $\iota$ can be observed as IBD between the two individuals. Practitioners notate the IBD state at site $\iota$ as $c_{*\iota}$, which is represented by a string of 4 integers each corresponding to the 4 haplotypes. The first two integers refer to the maternal and paternal haplotypes in individual 0 and the last two integers refer to the maternal and paternal haplotypes in individual 1. When the haplotype at site 1 is not IBD inventors represent it as a 0.

Therefore, $c_{*\iota} = 0000$ indicates that the two individuals at site 1 are not IBD, or zero IBD. Accordingly, there are 4 different ways the two individuals could be half IBD: 0101 is when the individuals are IBD through their paternal haplotypes, 1001 is when the individual 0's maternal haplotype is IBD with individual 1's paternal haplotype, 0110 is when the individual 0's paternal haplotype is IBD with individual 1's maternal haplotype, and 1010 is when the individuals are IBD through their maternal haplotypes.

Similarly there are 4 different ways the two individuals could be full IBD: 1212, 2112, 1221, and 2121. According to the model IBD segments follow a Markovian process in which segments begin and end independently. This means that when modeling full IBD practitioners must keep track of the identity of each of the two IBD segments so one cannot simply represent full IBD as 1111.

For this HMM, hidden states $Y_\iota$ represents the different ways site I could be observed as IBD and also includes information about the different ways in which the two individuals may or may not be in a switch error. There are 4 ways in which the two individuals may or may not be in a switch error: neither are in a switch error, individual 0 is in a switch error, individual 1 is in a switch error, or both individuals could be in a switch error. Since there are 9 ways site $\iota$ could be observed to be IBD and 4 ways phase switch errors could obfuscate the true IBD state, there are a total of 36 states for the latent variables Yi.

IBD Segment Model

Practitioners model the transitions among hidden states $Y_\iota$ with an instantaneous transition rate matrix. If, for a moment, practitioners do not consider transitions in which phase switch errors may occur and practitioners only consider transitions among the 9 IBD states that can be observed, practitioners can define the transition matrix $Q_\alpha$ shown in FIG. 9A.

The matrix $Q_\alpha$ defines the way the model moves between zero, half, and full IBD states. As the model passes along the chromosome as is the rate at which IBD segments begin $$\alpha_s = \frac{1}{1 + (100.0 \times m)} \quad \text{(Eq. 2)}$$

which depends on the number of meioses m on the pedigree between the two individuals being compared.

Similarly, the rate at which IBD segments end is $$\alpha_e = \frac{m}{100.0} \quad \text{(Eq. 3)}$$

Another way to interpret $\alpha_e$ is that it represents the length of the IBD segments shared between individuals 0 and 1.

Likewise $\alpha_s$ represents the length of segments with no IBD shared between the two individuals.

Full IBD Error Model

Phase switch errors break up half IBD segments into shorter adjacent half IBD segments on different haplotypes. Since the templated PBWTs procedure described above imperfectly estimates the start and end positions of IBD segments, when the lengths of the two adjacent half IBD segments are over estimated this can result in a short region of erroneous full IBD. Since full IBD is not expected for most pairs of relatives we model the error in the observed proportion of full IBD using a simple logistic function. Practitioners indicate the probability of full IBD truly being present as $\beta$, which is defined as $$\beta = \frac{1}{1+e^{\eta(0.125-\iota_2)}} \quad \text{(Eq. 4)}$$

Here $\iota_2$ is the amount of full IBD estimated by the templated PBWTs. When $\iota_2 \geq 25\%$ (the amount expected for full siblings) then the probability of there truly being full IBD is $\beta=1$. As the amount of full IBD estimated by the templated PBWTs $\iota_2$ approaches zero, $\beta$ also approaches zero. The steepness of the logistic curve is defined by $\eta$. Simulation tests showed $\eta=192$ was sufficient to reduce the error in full IBD introduced by the templated PBWTs.

We incorporate $\beta$ into the HMM by weighting the transitions into full IBD states with $\beta$ and by weighting the transitions out of full IBD states $1/\beta$. More explicitly, practitioners define $Q_\beta$ as:

$$Q_{\beta_{ij}} = \begin{cases} Q_{\alpha_{ij}} \times \beta, & \text{if } i \leq 5 \text{ and } j > 5 \\ Q_{\alpha_{ij}} \times \frac{1}{\beta}, & \text{if } i > 5 \text{ and } j \leq 5 \\ Q_{\alpha_{ij}}, & \text{otherwise} \end{cases} \quad \text{(Eq. 5)}$$

When $\beta=1{:}0$ note that $Q_\beta$ is equal to $Q_\alpha$.

Phase Switch Error Model

Finally practitioners are ready to incorporate phase switch errors into the HMM. Practitioners now expand the 9 state $Q_\beta$ matrix into the full 36 states that are possible among the hidden states $Y_\iota$.

$$Q = \begin{bmatrix} \text{no switch} & Q_\beta & \mu_0 Q_\beta & \mu_1 Q_\beta & \mu_0\mu_1 Q_\beta \\ \text{switch in 0} & \mu_0 Q_\beta & Q_\beta & \mu_0\mu_1 Q_\beta & \mu_1 Q_\beta \\ \text{switch in 1} & \mu_1 Q_\beta & \mu_0\mu_1 Q_\beta & Q_\beta & \mu_0 Q_\beta \\ \text{switch in both} & \mu_0\mu_1 Q_\beta & \mu_1 Q_\beta & \mu_0 Q_\beta & Q_\beta \end{bmatrix} \quad \text{(Eq. 6)}$$

Here practitioners incorporate two switch error rates $\mu_0$ and $\mu_1$ for individual 0 and individual 1, respectively. If both individuals were phased using the same method then one may set $\mu_0=\mu_1$. Given the genetic distance $d_\iota$ between sites $\iota$ and $\iota+1$, the number of meioses m, the switch error rates $\mu_0$ and $\mu_1$, and the amount of full IBD observed $\iota_2$, practitioners can find the probability of transitioning between the states $Y_\iota$ and $Y_{\iota+1}$ by exponentiating matrix Q:

$$P(Y_{\iota+1}|Y_\iota,m,\mu_0,\mu_1,\iota_2)=e^{Qd_\iota} \quad \text{(Eq. 7)}$$

Probability of Observed States

The probability of observing the IBD state $c_{*\iota}$ given the possible phase switch errors at site $\iota$ is $P(c_{*\iota}|Y_\iota)$, which are emission probabilities. Practitioners define these emission probabilities using a simple uniform error term $\varepsilon \geq 1$ that weights observed states based upon the 4 different ways the two individuals may be in phase switch errors. For example, when there are no phase switch errors in either individual, practitioners weight the emission probability so that it is more probable that the observed IBD state is the "true" hidden state:

$$P(c_{*\iota}|Y_\iota)=P(0101|0101;\text{no switch errors})=\varepsilon \times P\\(0101|1001;no \text{ switch errors}) \quad \text{(Eq. 8)}$$

Conversely, when there is a switch error in one or both of the two individuals practitioners do not expect the "true" hidden IBD state to be the same as the observed IBD state. For example, if there is a switch error in individual 0 then if the "true" IBD state is 1001 practitioners would most probably observe the state 0101:

$$P(c_{*\iota}|Y_\iota)=P(0101|1001;\text{switch error in ind0})=\varepsilon \times P\\(0101|0101;\text{switch error in ind0}) \quad \text{(Eq. 9)}$$

Similarly if there were switch errors in both individuals, when the "true" IBD state is 2121 practitioners would observe 1212 with the highest probability. As $\varepsilon \to \infty$, the phase switch errors will entirely determine what IBD state can be observed. If $\varepsilon=1$, all IBD states can be observed with equal probability regardless of the hidden state $Y_\iota$.

Integrating the templated PBWT and the HMM

An implementation described here is named Phased IBD. It is used in the experiments described hereinafter. It has two stages: First the templated PBWT and then the phase-correcting HMM. The templated PBWT stage generates the IBD segments among all haplotypes very quickly and efficiently. However, if run on many pairs (e.g., thousands or millions pairs) of individuals, the second stage of the algorithm (the HMM) would be prohibitively slow for large datasets. In those datasets, though, most individuals will not share any IBD and so they do not require any phase switch error correction. Moreover, the vast majority of related individuals will only be distantly related and share few IBD segments. If they share at most one IBD segment per chromosome then phase switch errors have not broken up their observed IBD segments and so the HMM does not apply. The HMM, the slow stage of the 2-part algorithm, is thus only applied to the small number of individuals within the dataset that are closely related. Practitioners require a pair of individuals to have at least 2 observed IBD segments on a single chromosome before running them through the phase-correcting HMM, though additionally we can require a minimum total amount of shared IBD (in cM) to increase the speed of the entire algorithm.

Processing IBD Segments

Identified IBD segments can be used for a wide range of purposes. For instance, the amount (length and number) of IBD sharing depends on the familial relationships between the tested individuals. Therefore, one application of IBD segment detection is to quantify relatedness. For example, methods for using IBD segments to quantify relatedness are described in U.S. Pat. No. 8,463,554, issued Jul. 11, 2013, which is incorporated by reference in its entirety for all purposes.

In some implementations, the number of shared IBD segments and the amount of DNA shared by two users are computed based on the IBD segments obtained as described above. In some implementations, the longest IBD segment is determined. In some implementations, the amount of DNA shared includes the sum of the lengths of IBD regions and/or percentage of DNA shared. The sum is referred to as IBDhalf or half IBD because the individuals share DNA identical by descent for at least one of the homologous chromosomes. The predicted relationship between the users, the range of possible relationships, or both, is determined using the IBDhalf and number of segments, based on the distribution pattern of IBDhalf and shared segments for different types of relationships. For example, in a first degree parent/child relationship, the individuals have IBDhalf that is 100% the total length of all the autosomal chromosomes and 22 shared autosomal chromosome segments; in a second degree grandparent/grandchild relationship, the individuals have IBDhalf that is approximately half the total length of all the autosomal chromosomes and many more shared segments; in each subsequent degree of relationship, the percentage of IBDhalf of the total length is about 50% of the previous degree. Also, for more distant relationships, in each subsequent degree of relationship, the number of shared segments is approximately half of the previous number.

There is a statistical range of possible relationships for the same IBDhalf and shared segment number. In some implementations, the distribution patterns are determined empirically based on survey of real populations. Different population groups may exhibit different distribution patterns. For example, the level of homozygosity within endogamous populations is found to be higher than in populations receiving gene flow from other groups. In some implementations, the bounds of particular relationships are estimated using simulations of IBD using generated family trees. Based at least in part on the distribution patterns, the IBDhalf, and shared number of segments, the degree of relationship between two individuals can be estimated.

IBD segments can also be used determine ethnicity or ancestry. See, e.g., U.S. patent application Ser. No. 15/664,619, filed Jul. 31, 2017, which is incorporated by reference in its entirety for all purposes.

Moreover, IBD can be used to perform genotype imputation. Genotype imputation refers to the statistical inference of genotype information not directed assayed. This is especially helpful because many individuals only have sparsely assayed genotype data, usually targeting a limited number of genetic markers in the genome. If IBD segments are determined between two individuals, it can be inferred that the genotype of the two individuals are the same in the IBD segments. Thus the known genotype information of an IBD segment of one of the two individuals can be "imputed" into that of the other individual. This further allows association study between phenotypes and genotypes even using individuals that have only the phenotype data collected but not the genotype data assayed. See, e.g., U.S. patent application Ser. No. 15/256,388, filed Sep. 2, 2016, which is incorporated by reference in its entirety for all purposes.

Apparatus and Systems

Figure 10:
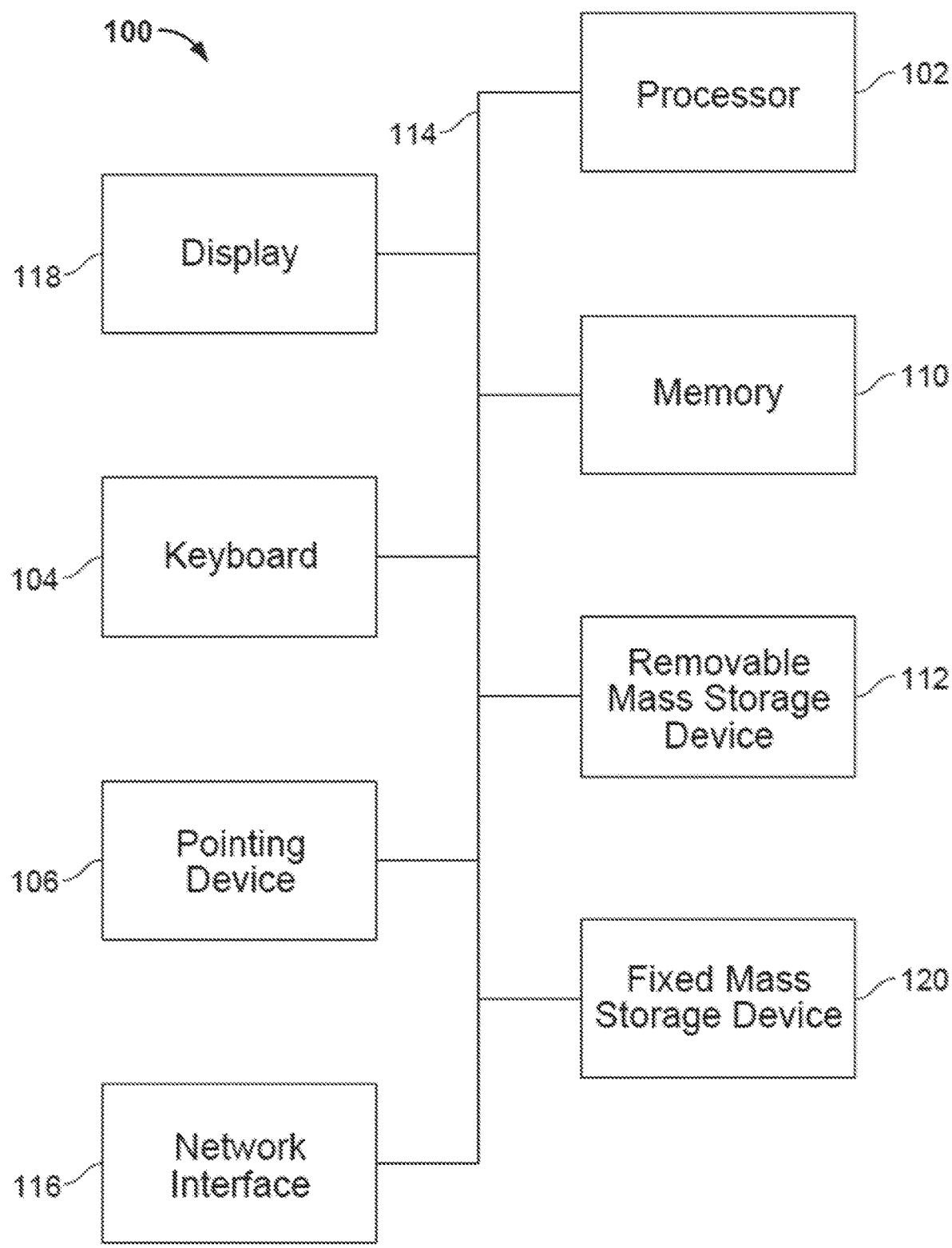
FIG. 10 presents a functional diagram of a computer system for performing various embodiments disclosed herein.

FIG. 10 is a functional diagram illustrating a programmed computer system for performing the pipelined ancestry prediction process in accordance with some implementations. Computer system 100, which includes various subsystems as described below, includes at least one microprocessor subsystem (also referred to as a processor or a central processing unit (CPU)) 102. For example, processor 102 can be implemented by a single-chip processor or by multiple processors. In some implementations, processor 102 is a general purpose digital processor that controls the operation of the computer system 100. Using instructions retrieved from memory 110, the processor 102 controls the reception and manipulation of input data, and the output and display of data on output devices (e.g., display 118). In some implementations, processor 102 includes and/or is used to provide phasing, genotype error correction, and/or phasing error correction, etc. as described herein.

Processor 102 is coupled bi-directionally with memory 110, which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 102. Also as is well known in the art, primary storage typically includes basic operating instructions, program code, data, and objects used by the processor 102 to perform its functions (e.g., programmed instructions). For example, memory 110 can include any suitable computer-readable storage media, described below, depending on whether, for example, data access needs to be bi-directional or uni-directional. For example, processor 102 can also directly and very rapidly retrieve and store frequently needed data in a cache memory (not shown).

A removable mass storage device 112 provides additional data storage capacity for the computer system 100, and is coupled either bi-directionally (read/write) or uni-directionally (read only) to processor 102. For example, storage 112 can also include computer-readable media such as magnetic tape, flash memory, PC-CARDS, portable mass storage devices, holographic storage devices, and other storage devices. A fixed mass storage 120 can also, for example, provide additional data storage capacity. The most common example of mass storage 120 is a hard disk drive. Mass storage 112, 120 generally store additional programming instructions, data, and the like that typically are not in active use by the processor 102. It will be appreciated that the information retained within mass storage 112 and 120 can be incorporated, if needed, in standard fashion as part of memory 110 (e.g., RAM) as virtual memory.

In addition to providing processor 102 access to storage subsystems, bus 114 can also be used to provide access to other subsystems and devices. As shown, these can include a display monitor 118, a network interface 116, a keyboard 104, and a pointing device 106, as well as an auxiliary input/output device interface, a sound card, speakers, and other subsystems as needed. For example, the pointing device 106 can be a mouse, stylus, track ball, or tablet, and is useful for interacting with a graphical user interface.

The network interface 116 allows processor 102 to be coupled to another computer, computer network, or telecommunications network using a network connection as shown. For example, through the network interface 116, the processor 102 can receive information (e.g., data objects or program instructions) from another network or output information to another network in the course of performing method/process steps. Information, often represented as a sequence of instructions to be executed on a processor, can be received from and outputted to another network. An interface card or similar device and appropriate software implemented by (e.g., executed/performed on) processor 102 can be used to connect the computer system 100 to an external network and transfer data according to standard protocols. For example, various process implementations disclosed herein can be executed on processor 102, or can be performed across a network such as the Internet, intranet networks, or local area networks, in conjunction with a remote processor that shares a portion of the processing. Additional mass storage devices (not shown) can also be connected to processor 102 through network interface 116.

An auxiliary I/O device interface (not shown) can be used in conjunction with computer system 100. The auxiliary I/O device interface can include general and customized interfaces that allow the processor 102 to send and, more typically, receive data from other devices such as microphones, touch-sensitive displays, transducer card readers, tape readers, voice or handwriting recognizers, biometrics readers, cameras, portable mass storage devices, and other computers.

In addition, various implementations disclosed herein further relate to computer storage products with a computer readable medium that includes program code for performing various computer-implemented operations. The computer-readable medium is any data storage device that can store data which can thereafter be read by a computer system. Examples of computer-readable media include, but are not limited to, all the media mentioned above: magnetic media such as hard disks, floppy disks, and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code, as produced, for example, by a compiler, or files containing higher level code (e.g., script) that can be executed using an interpreter.

The computer system shown in FIG. 10 is but an example of a computer system suitable for use with the various implementations disclosed herein. Other computer systems suitable for such use can include additional or fewer subsystems. In addition, bus 114 is illustrative of any interconnection scheme serving to link the subsystems. Other computer architectures having different configurations of subsystems can also be utilized.

Figure 11:
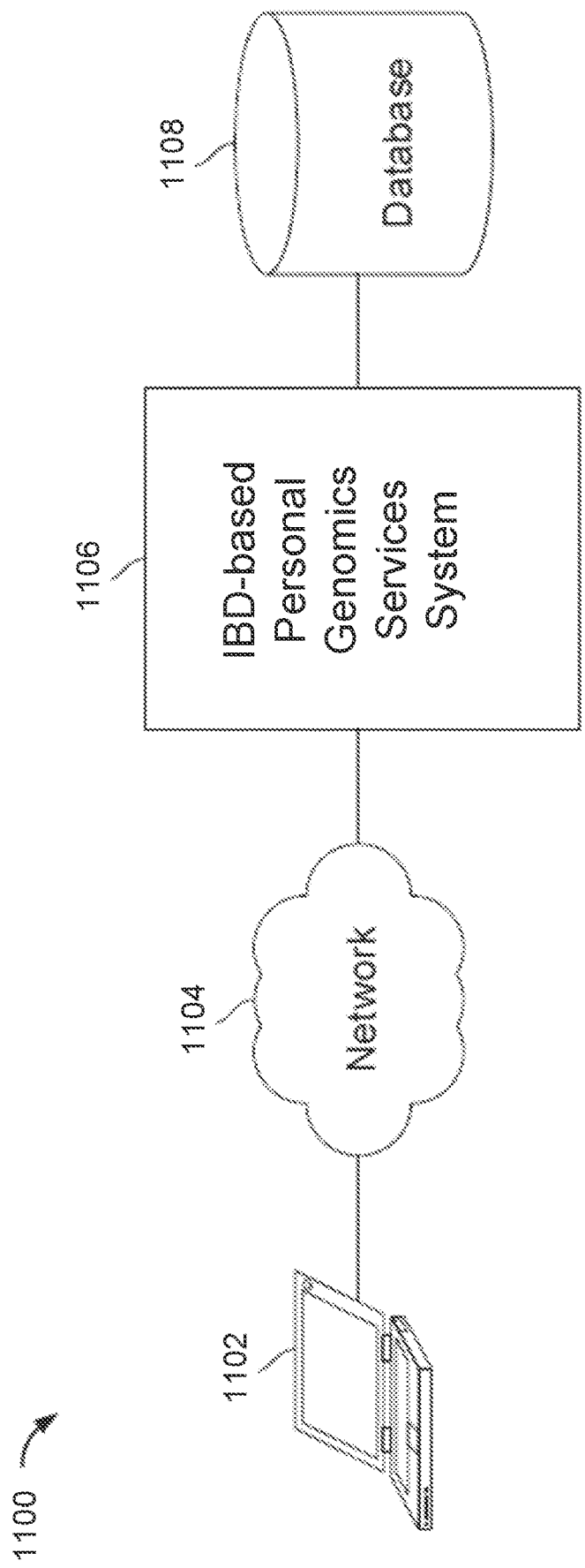
FIG. 11 presents a block diagram of an IBD-based personal genomics service according to various embodiments herein.

FIG. 11 is a block diagram illustrating an implementation of an IBD-based personal genomics services system 1100 that provides services based on IBD information, which include but are not limited to relatedness estimation, relative detection, ancestry determination, and genotype-phenotype association. In this example, a user uses a client device 1102 to communicate with an IBD-based personal genomics services system 1106 via a network 1104. Examples of device 1102 include a laptop computer, a desktop computer, a smart phone, a mobile device, a tablet device or any other computing device. IBD-based personal genomics services system 1106 is used to perform a pipelined process to predict ancestry based on a user's IBD information. IBD-based personal genomics services system 1106 can be implemented on a networked platform (e.g., a server or cloud-based platform, a peer-to-peer platform, etc.) that supports various applications. For example, implementations of the platform perform ancestry prediction and provide users with access (e.g., via appropriate user interfaces) to their personal genetic information (e.g., genetic sequence information and/or genotype information obtained by assaying genetic materials such as blood or saliva samples) and predicted ancestry information. In some implementations, the platform also allows users to connect with each other and share information. Device 110 can be used to implement 1102 or 1106.

In some implementations, DNA samples (e.g., saliva, blood, etc.) are collected from genotyped individuals and analyzed using DNA microarray or other appropriate techniques. The genotype information is obtained (e.g., from genotyping chips directly or from genotyping services that provide assayed results) and stored in database 1108 and is used by system 1106 to make ancestry predictions. Reference data, including genotype data of reference individuals, simulated data (e.g., results of machine-based processes that simulate biological processes such as recombination of parents' DNA), pre-computed data (e.g., a precomputed reference haplotype data used in phasing and model training) and the like can also be stored in database 1108 or any other appropriate storage unit.

EXPERIMENTAL

This experiment compares a method according to some implementations as described above to other computer implemented methods known in the art. All of these methods are computer-implemented. IBD accuracies and computer performances are compared among the methods.

The method according to some implementations is labeled as Phased IBD. It includes techniques as described in the templated PBWT and the HMM examples above.

A method described by Durbin is labeled as PBWT. See, R. Durbin. Efficient haplotype matching and storage using the positional Burrows-Wheeler transform (PBWT). Bioinformatics, 30(9): 1266-1272, 2014.

The method described by Naseri is labeled as RaPID. See, A. Naseri, X. Liu, S. Zhang, and D. Zhi. Ultra-fast identity by descent detection in biobank-xcale cohorts using positional Burrows-Wheeler transform. bioRxiv, page 103325, 2017.

The method described by Browning is labeled as Refined IBD. See, B. L. Browning and S. R. Browning. Improving the accuracy and efficiency of identity-by-descent detection in population data. Genetics, 194(2):459-471, 2013.

A method described by Zhou is labeled hap-IBD. See, Y. Zhou, S. R. Browning, and B. L. Browning. A fast and simple method for detecting identity by descent segments in large-scale data. BioRxiv, 2019.

A method described by Shemirani is labeled iLASH. See, R. Shemirani, G. M. Belbin, C. L. Avery, E. E. Kenny, C. R. Gignouz, and J. L. Ambite. Rapid detection of identity-by-descent tracts for mega-scale datasets. BioRxiv, page 749507, 2019.

Figure 12:
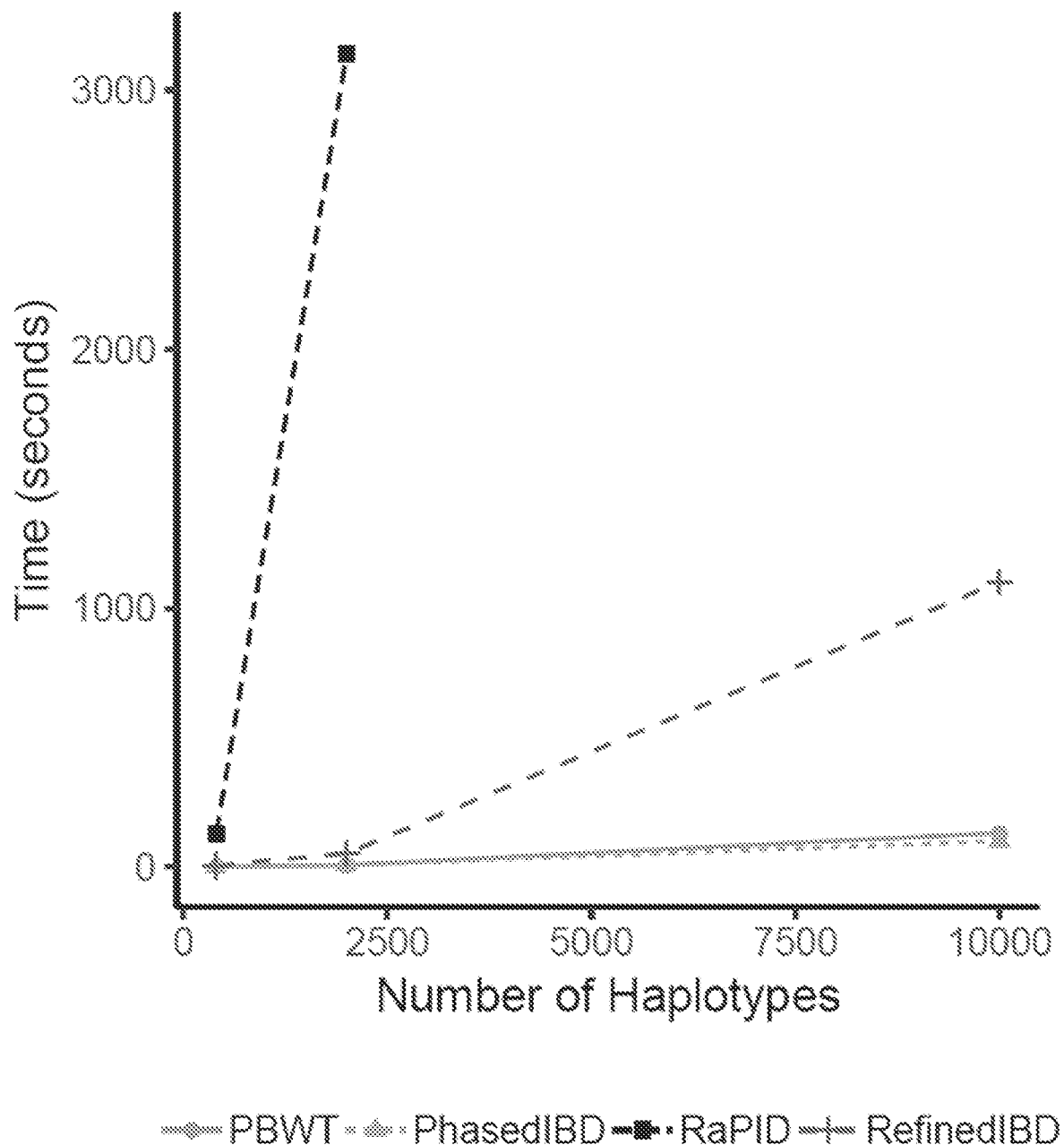
FIG. 12 presents a plot comparing the speed of various IBD inference methods.

FIG. 12 shows results comparing the speed of different IBD inference methods. IBD segments were computed for 50781 SNPs from human chromosome 1. The x-axis shows the number of haplotypes and the y-axis shows the time in seconds to infer IBD. Phased IBD used a minimum IBD segment length of 200 sites and 1.5 cM. Durbin's PBWT used a 200 site minimum. RaPID (version 1.2.3) used 10 runs, 2 successes, window size of 35, and minimum length of 1.5 cM. Refined IBD used a minimum length of 1.5 cM and all default parameter value settings. The results of FIG. 11 show that Phased IBD and PBWT are the fastest among the four methods and similar to each other. RaPID is the slowest.

As explained above and illustrated below, Phased IBD can correct various errors (including genotyping errors and phase switch errors) that cannot be addressed by PBWT, it is noteworthy that Phased IBD achieves similar computational speed as PBWT.

Figure 14:
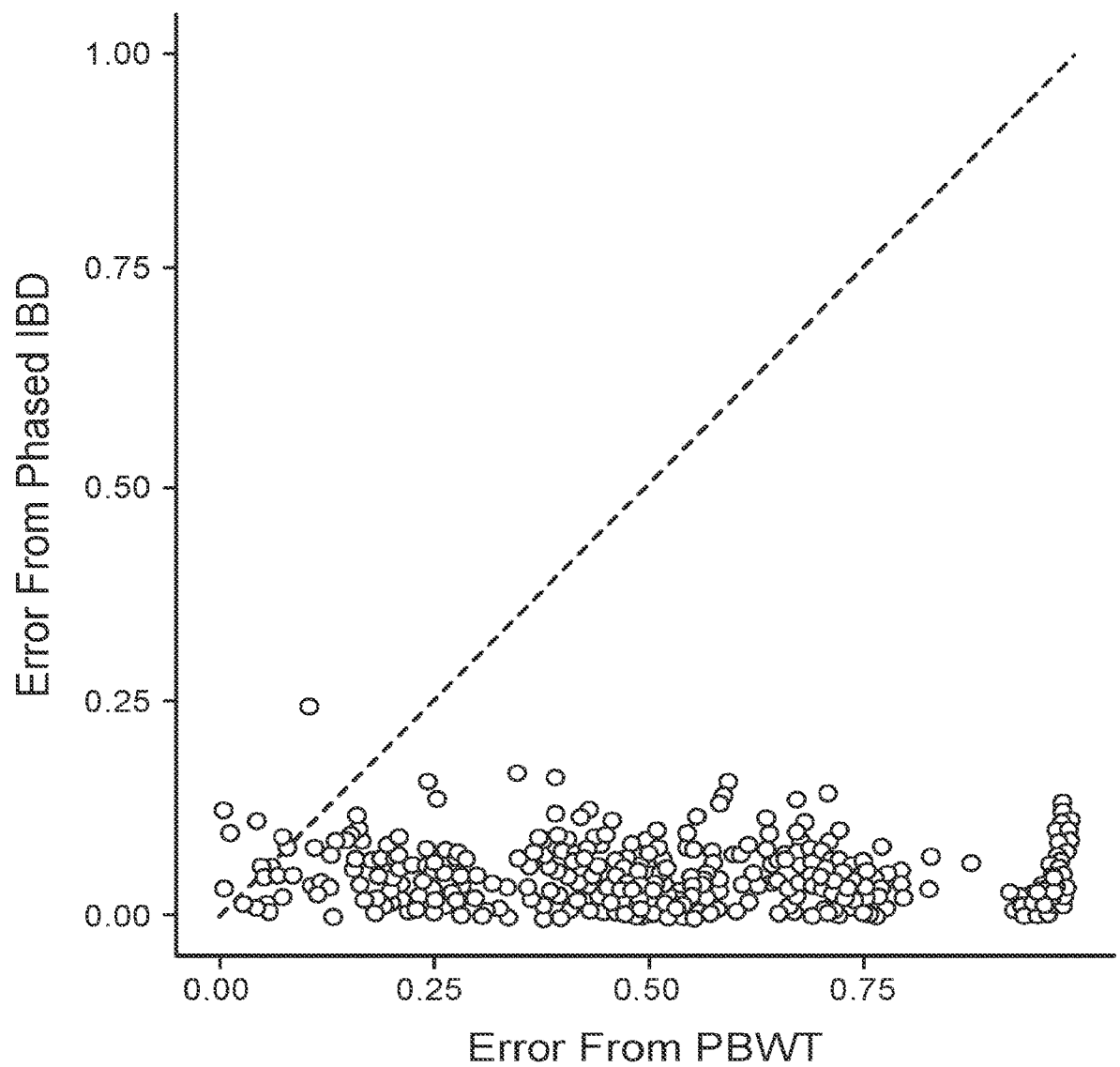
Figure 15:
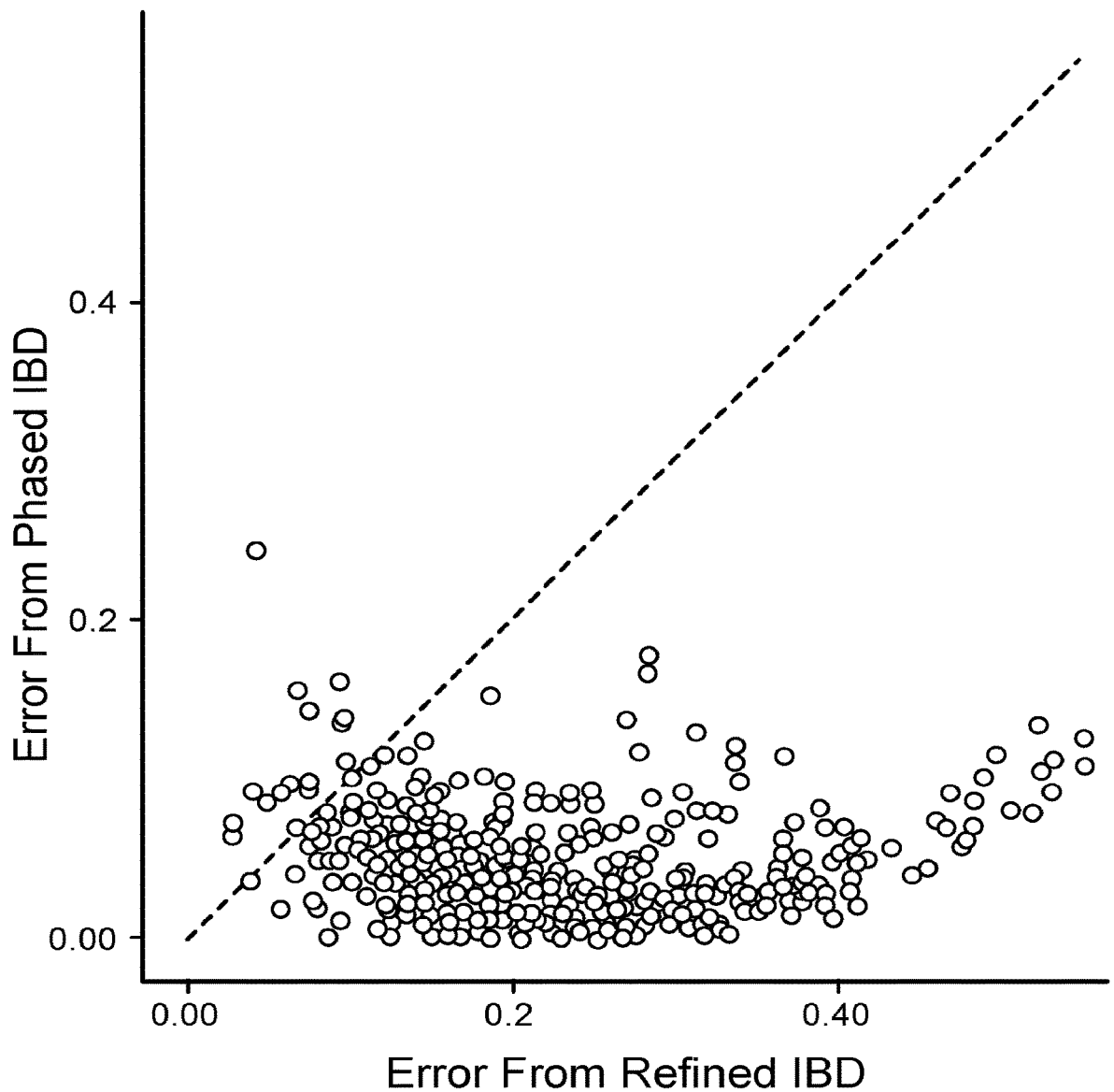

On the other hand, although RaPID and Refined IBD can correct errors, albeit to a lesser extent than Phased IBD as shown in FIGS. 14 and 15, they require significantly longer computer run time.

Figure 13:
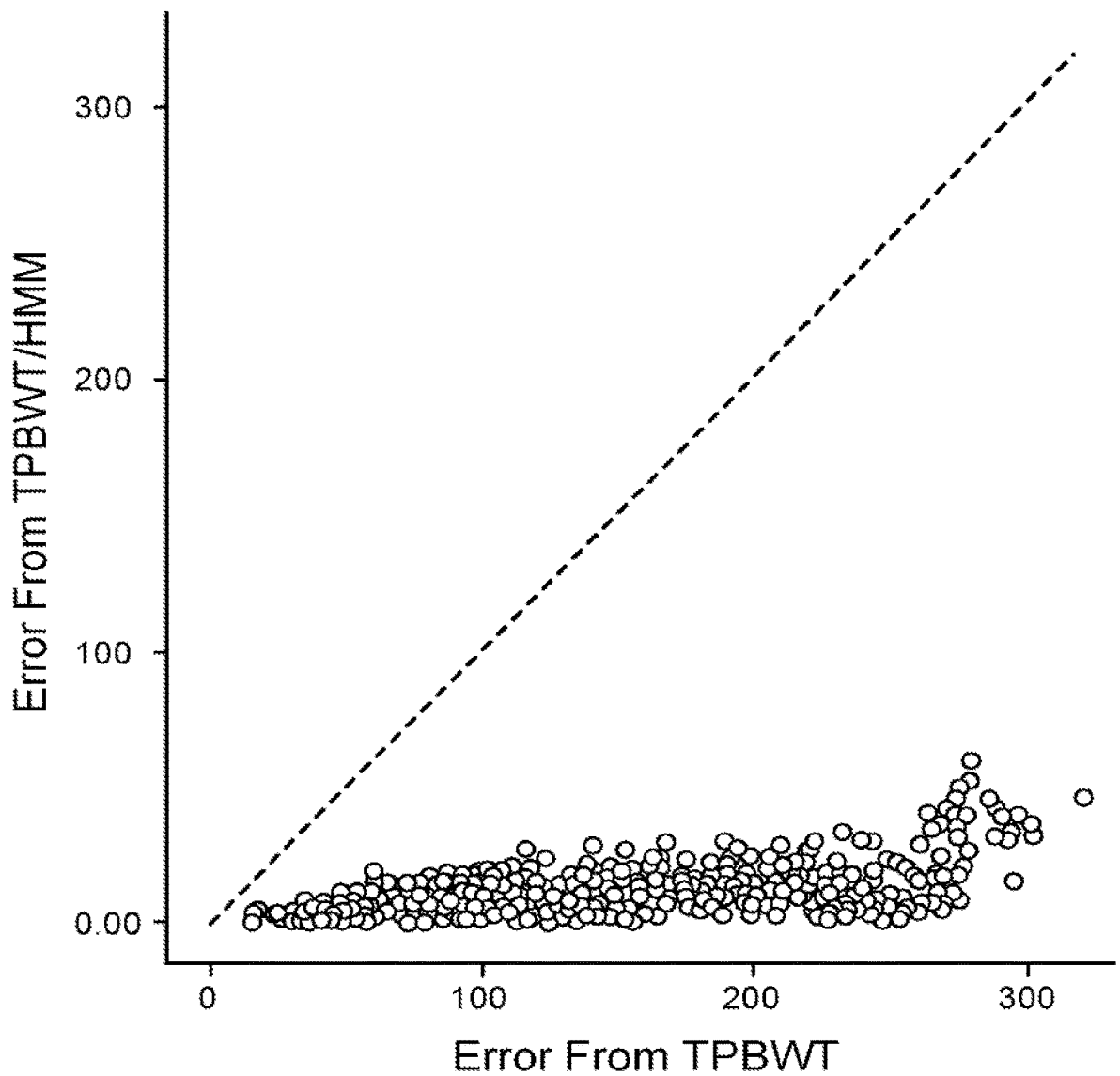
FIGS. 13-16 present plots comparing the IBD estimate errors of various methods.

FIGS. 13-16 compare the IBD estimate errors (or the opposite of accuracy) of various methods. FIG. 13 compares the absolute error in number of IBD segments between the Templated PBWT method (x-axis) and Phased IBD (y-axis) that includes both Templated PBWT component and the HMM component. The results of FIG. 13 show that the HMM process greatly reduce the error rates, reducing maximum error segments by about three folds from about 300 to 100.

FIG. 14 shows that Phased IBD is more accurate than PBWT. Each axis shows the proportion of the genome with incorrect IBD estimates. PBWT (x-axis) is sensitive to both genotyping and phasing errors compared to Phased IBD (y-axis).

FIG. 15 shows that Phased IBD is more accurate than Refined IBD. Refined IBD (x-axis) has higher error than Phased IBD (y-axis), although Refined IBD outperforms both PBWT and RaPID.

Figure 16:
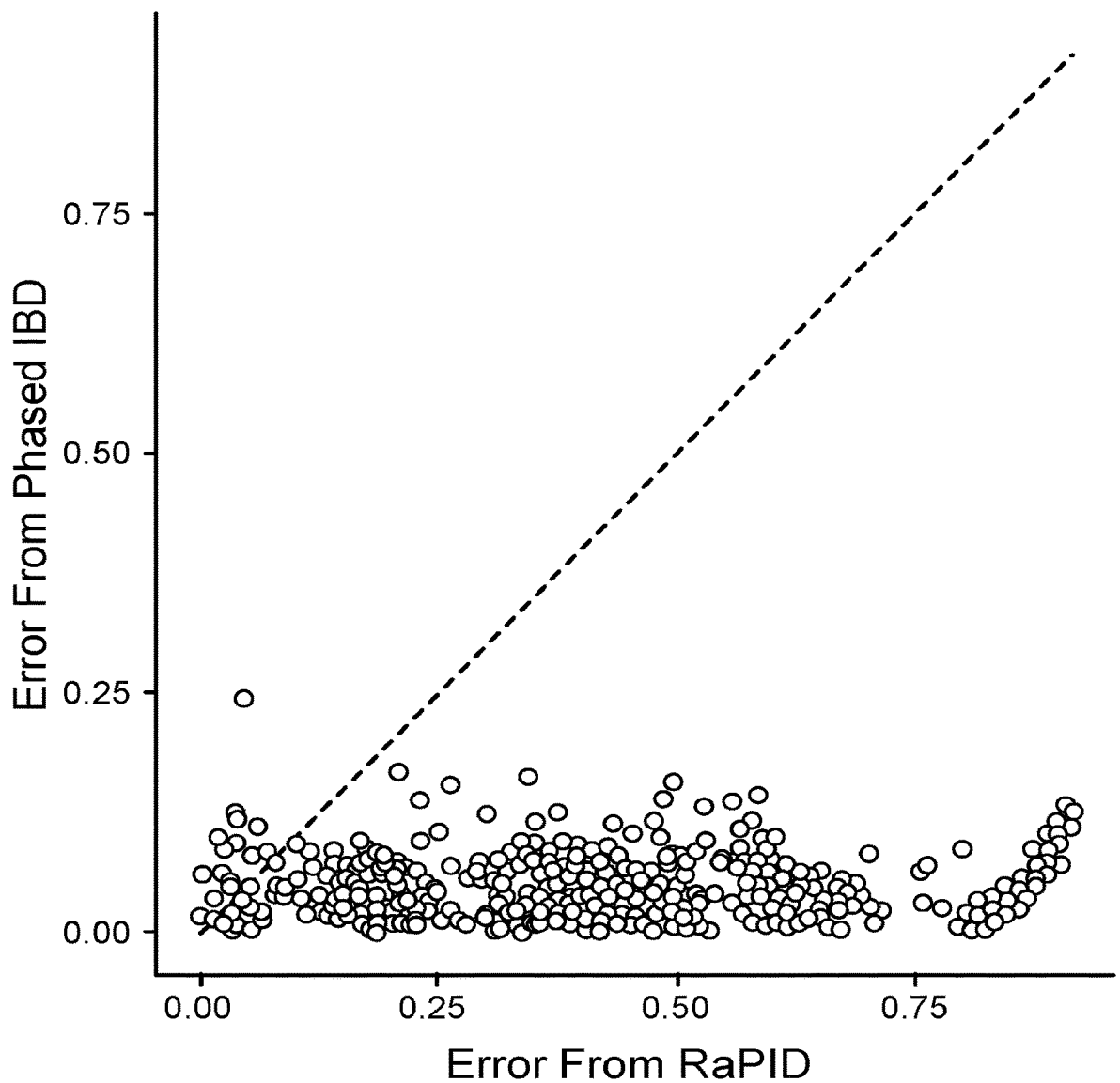

FIG. 16 shows that Phased IBD is more accurate than RaPID (version 1.2.3). RaPID (x-axis), like PBWT, has high error in relationship types with long IBD segments like parent-child and siblings. Unlike other methods, Phased IBD "stitches" together long IBD segments highly fragmented by phasing and genotyping errors.

Simulation Study

A simulation study was performed to assess the accuracy of IBD inference methods. Simulated haplotype data sets in which the IBD segments shared were perfectly known were created and then modified to introduce realistic levels of genotyping and phasing errors to test the impact of the errors on IBD segment determinations. Haplotypes inherited with recombination over 400 replicated pedigrees were simulated. Each pedigree had three generations and included at least one pair of each type of close relatives that were used for the simulation study: parent-child, grandparent-grandchild, aunt-niece, first cousins, and siblings. Each pedigree founder consisted of a randomly sampled and unrelated research consented 23andMe customer. Recombination was simulated using a Poisson model with a rate of 1 expected crossover per 100 cM. This resulted in simulated haplotypes for 2000 closely related pairs of individuals with perfectly known IBD segments, 400 pairs of each relationship type: parent-child, grandparent-grandchild, aunt-niece, first cousins, and siblings.

Genotyping errors were introduced into the simulated data set using a simple model. At each position along the simulated chromosomes an error in the genotype call was introduced with a probability of 0.001. When a site was selected for an error, half of the genotype call would be flipped with equal probability (e.g., a 0/0 genotype would be converted to a 1/0 or a 0/1 with equal probability).

Statistical phasing errors were also introduced into the simulated haplotype datasets. All of the simulated haplotypes were converted into their respective diploid genotypes and then the statistical haplotype phasing method Eagle2 was used. For the phasing reference panel a phasing panel that included about 200000 non-Europeans and about 300000 Europeans was used.

The various methods used to analyze the simulated data had the following parameters:

TABLE 1

Algorithm parameter values used for the IBD inference methods during analysis of simulated data.

| Software | Parameters |
|---|---|
| TPBWT | Default templates, L_m = 200, L_f = 3.0, phase switch error correction heuristic on |
| PBWT | −longWithin 200 |
| Hap-IBD v1.0 | Default options, except nthreads = 1 length = 3.0 |
| RaPID v1.7 | −w 3 −r 10 −s 2 −d 3.0 |
| Refined IBD v16May19 | Default options, except nthreads = 1 length = 3.0 |
| iLASH | Perm_count 12 shingle_size 20 shingle_overlap 0 bucket_count 4 max_thread 1 match_threshold 0.99 interest_threshold 0.70 min_length 3.0 auto_slice 1 cm_overlap 1.4 |

Figure 17:
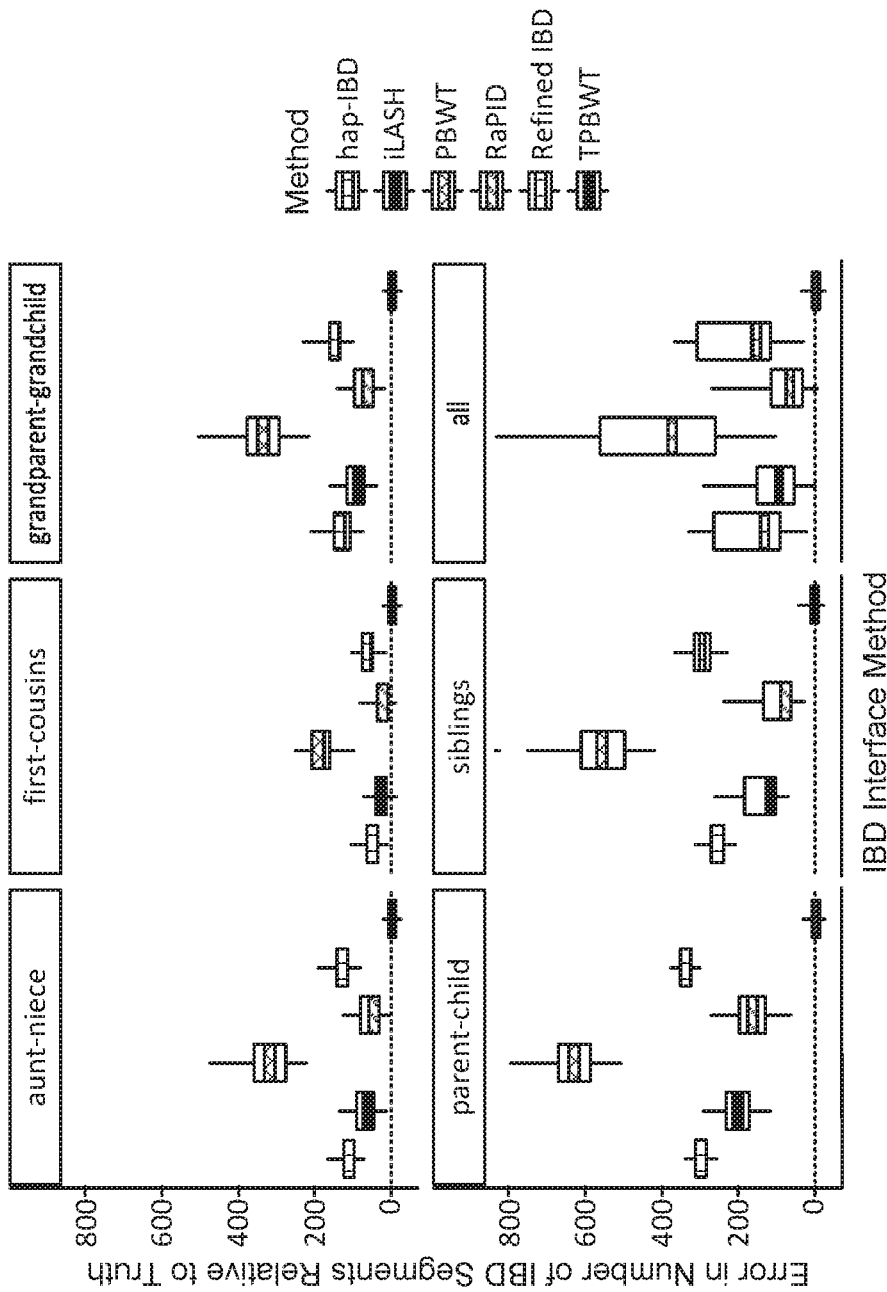
FIGS. 17 and 18 present plots of errors of various methods for various simulated pairs of haplotypes.

FIG. 17 shows that Templated PBWT had less error in the estimated number of IBD segments shared between relatives than all other methods analyzed. The y-axis represents the number of erroneous IBD segments estimated for a simulated pair of relatives. Error was highest in closely related pairs that shared long IBD segments, particularly parent-child and siblings.

Figure 18:
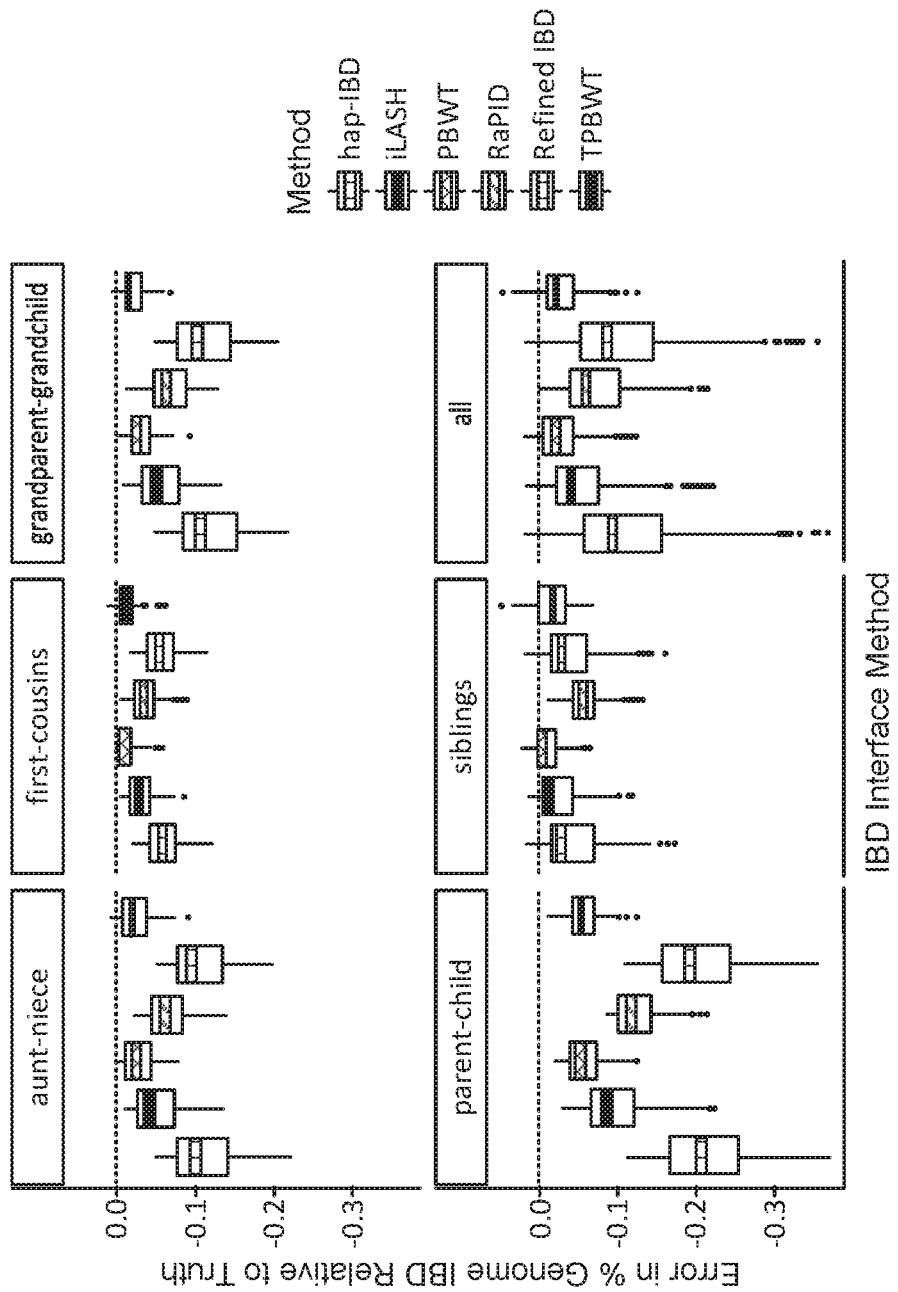

FIG. 18 shows that Templated PBWT had less error in the estimated percentage of the genome that is IBD in simulated relatives than other methods. PBWT had less than error than other methods except Templated PBWT, while hap-IBD and Refined IBD had the largest error. Error was higher in simulated pairs that shared long IBD segments, such as parent-child, compared to more distance relatives pairs such as first cousins. Compared to Templated PBWT, the other methods were more sensitive to phasing and genotyping errors in estimated IBD segments.

Figure 19:
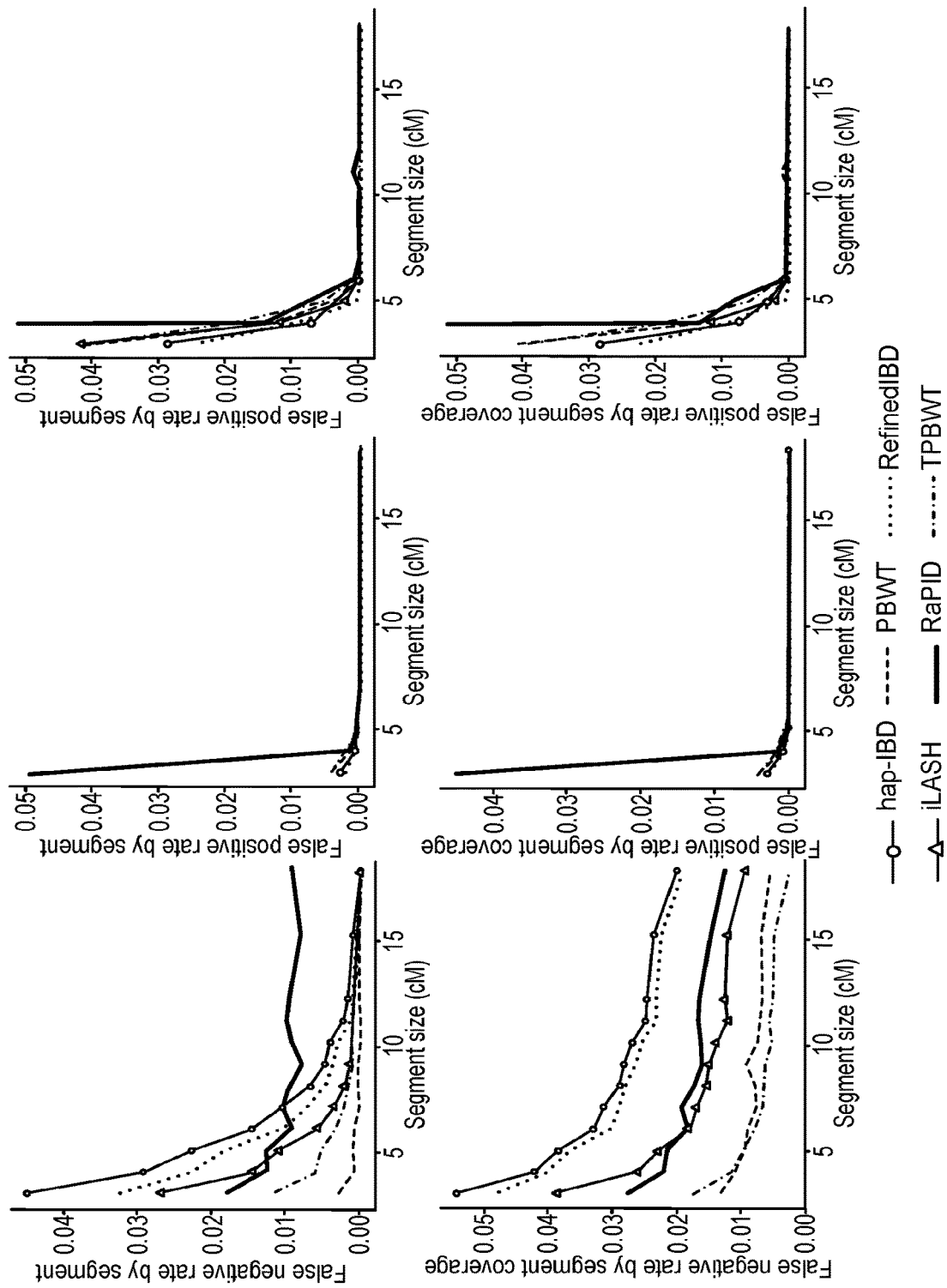
FIG. 19 presents plots of the false positive and false negative rates of various methods.

FIG. 19 shows false negative (charts 1901 and 1905) and false positive rates (charts 1903a-b and 1907a-b) of inferring IBD by various methods. Rates were calculated for bins of IBD segment lengths. False negative rate by segment is the proportion of true segments in a size bin that do not overlap any segment compared to the total number of true segments in the size bin. False negative rate by segment coverage is the proportion of the length of true segments in a size bin not covered by any estimated segment compared to the total length of true segments in the size bin. False positive rate by segment is the proportion of estimated segments in a size bin that do not overlap any true segment compared to the total number of estimated segments in the size bin. False positive rate by segment coverage is the proportion of the length of estimated segments in a size bin not covered by any true segment compared to the total length of estimated segments in the size bin. Plots 1903b and 1907b present the false positive rate with a smaller y-axis scale than plots 1903a and 1907a, respectively. For IBD segments ≥4 cM all methods had low false positive rates. For IBD segments greater than ≥6 cM the Templated PBWT outperformed all other methods.

Figure 20A:
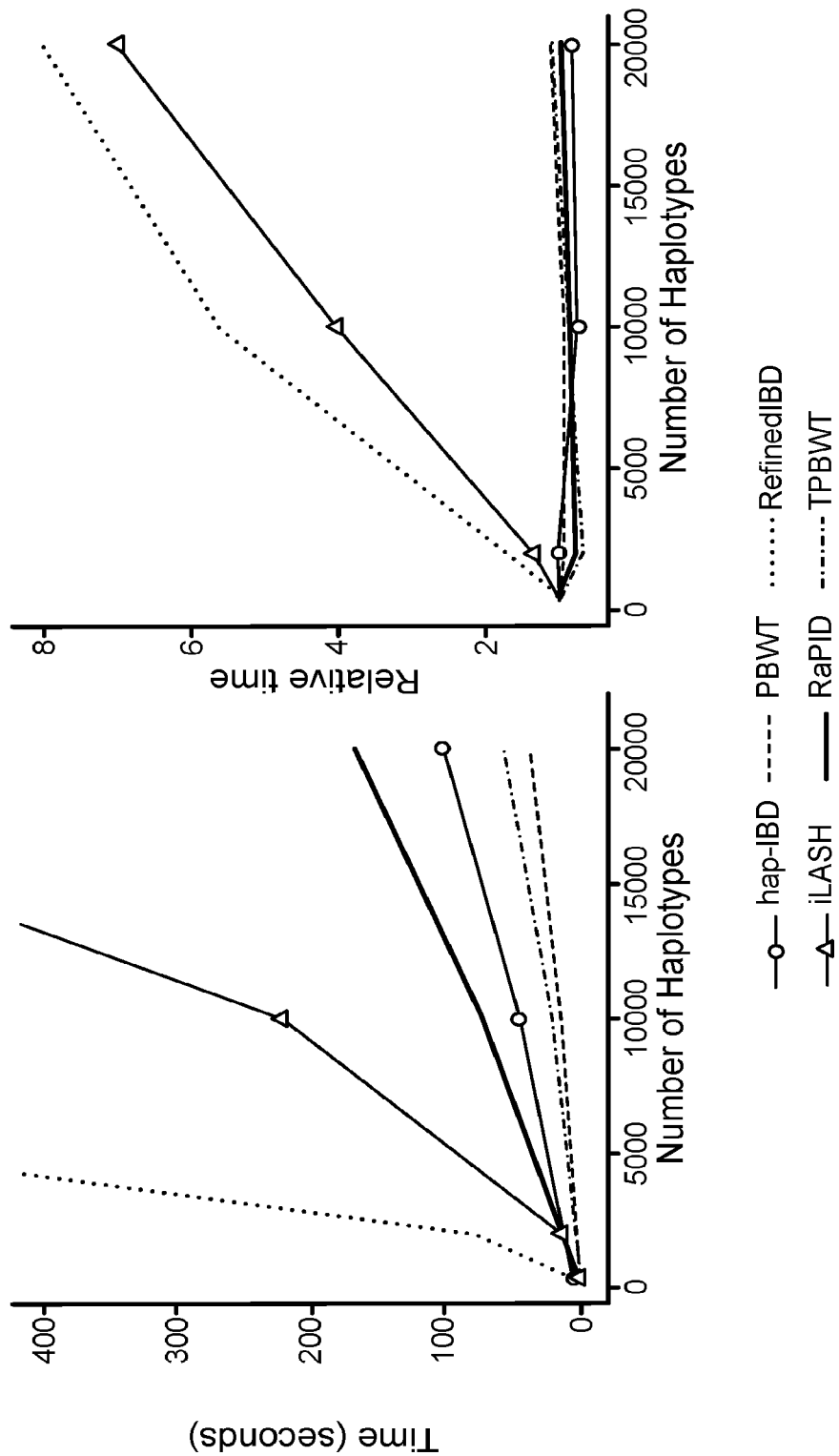

FIG. 20A shows IBD computation runtimes for various methods. All methods were run using 1 CPU core. Templated PBWT was faster than all other methods except Durbin's PBWT. The relative time shows the runtime to compute IBD for each haplotype in sample sizes of 400 to 20000 haplotypes relative to the time needed to compute IBD for each haplotype in a sample size of 400. A slope near zero indicates linear time complexity, while a positive slope indicates super-linear time complexity. Templated PBWT shows a near linear time complexity. FIG. 20B provides additional compute times for parallelized IBD analyses with large sample sizes. Times are shown for in-sample IBD computes on 1 million individuals, out-of-sample IBD computes on 10 k individuals against 1 million, and out-of-sample IBD computes on 10 k individuals against 10 million. The first two rows show the compute times measured when IBD was estimated over 42927 sites of human chromosome 1. The last three rows show those compute times extrapolated to 23 chromosomes with a total of 600 k sites. The last row additionally extrapolates the time for an out-of-sample analysis on 1 million to 10 million individuals. CPU time is the sum of the computation time for all compute cores. Wall clock time is the "real" time that the entire analysis took to run.

Haplotype Sharing in Mexico

To demonstrate the utility of the IBD estimates made using the Templated PBWT and the 23andMe database a brief case study was performed to examine the geographic patterns of haplotype sharing within Mexico. 9517 research consented 23andMe customers who self reported that all 4 of their grandparents were from the same Mexican state were identified. Each customer was genotyped on either the 23andMe v4 or v5 bead chip genotyping platform. SNPs with <85% genotyping rate, SNPs with MAF <0.001, SNPs with low trio concordance (effect<0.6 and p-value<1e-20), and SNPs with allele counts of 0 within the samples selected for the phasing reference panel were removed. After this quality control filtering the v4 platform had 453065 SNPs and v5 platform had 544042 SNPs. Haplotypes were phased using Eagle2 as described in Loh et. al., Reference-based phasing using the haplotype reference consortium panel. Nature genetics, 48(11):1443, 2016. Individuals on the v4 platform were phased with a reference panel containing 691759 samples. Individuals on the v5 platform were phased with a reference panel containing 286305 samples.

IBD sharing among the 9517 individuals was computed using the Templated PBWT with the parameters described in Table 1. IBD estimates among individuals on the same genotyping platform were made using the in-sample method described above, and estimates made among individuals on different platforms was made using the out-of-sample approach described above over the intersection of platform SNPs (only the SNPs present in both the v4 and v5 genotyping platforms). Hierarchical clustering of the mean pairwise IBD haplotype sharing across Mexican states was performed using Ward's method (Ward Jr 1963) in R. To remove close relatives we excluded any pair of individuals that shared more than 20 cM. Geographic maps of the mean pairwise IBD shared across Mexican states were made using the β packages mxmaps, ggplot2, and viridis (Valle-Jones 2019; Wickham 2016; Garnier 2018).

Figure 21:
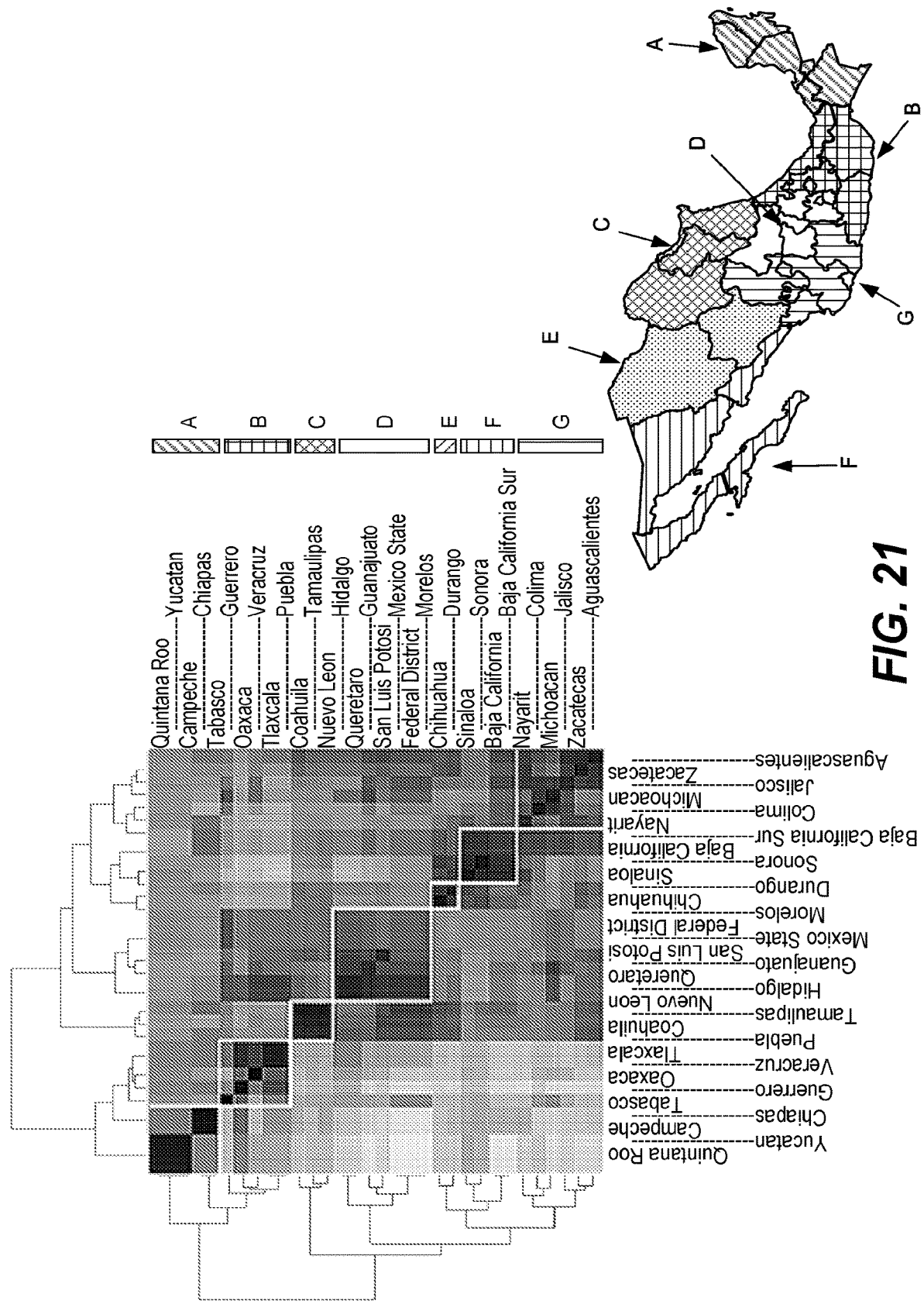
FIGS. 21 and 22 present illustrates of IBD haplotype sharing across Mexican states as determined by a Templated PBWT method as described herein.
Figure 22:
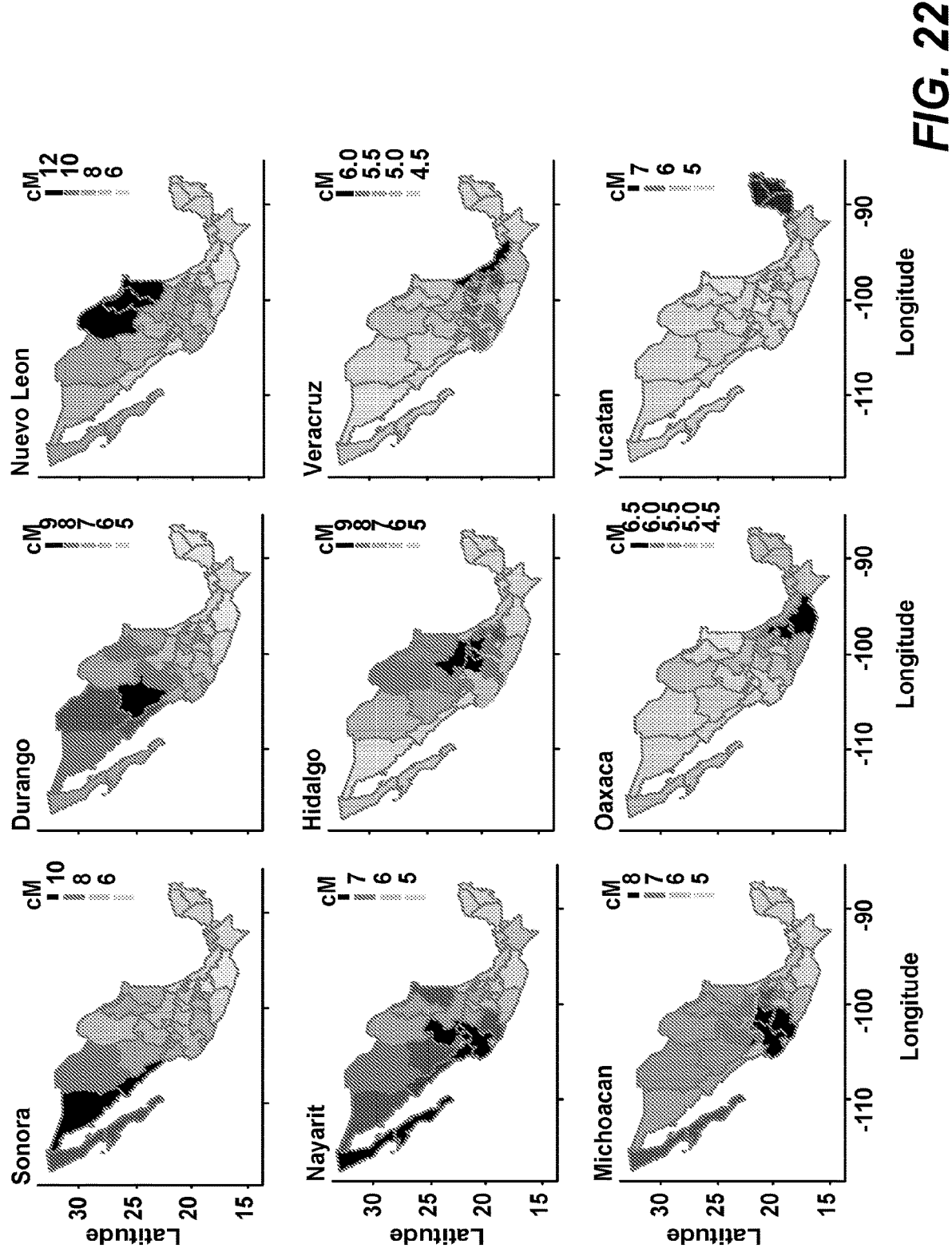

FIGS. 21 and 22 show IBD haplotype sharing across Mexican states as determined by a Templated PBWT method. Hierarchal clustering of IBD sharing across Mexican states identified geographic clusters with elevated levels of haplotype sharing, as shown in FIG. 21. There were two large clusters: one cluster in the Yucatan peninsula and the southern Mexican states, and another cluster representing Mexico City and the central and northern states. The clusters were further subdivided into individual states.

Mean pairwise IBD haplotype sharing was highest within states and among geographically neighboring states, as shown in FIG. 22. For example, mean IBD shared among individuals with all 4 grandparents from Nuevo Leon was over 12 cM, and the mean pairwise IBD shared between individuals with all 4 grandparents from Nuevo Leon and individuals with all 4 grandparents from neighboring Coahuila and Tamaulipas was over 10 cM. In contrast, mean pairwise sharing between individuals with all 4 grandparents from Nuevo Leon and individuals with all 4 grandparents from Yucatan was less than 6 cM. Similar geographically stratified IBD sharing was found throughout Mexico, as shown in FIG. 22.

CONCLUSION

In the description above, for purposes of explanation only, specific nomenclature is set forth to provide a thorough understanding of the present disclosure. However, it will be apparent to one skilled in the art that these specific details are not required to practice the teachings of the present disclosure.

The language used to disclose various embodiments describes, but should not limit, the scope of the claims. For example, in the previous description, for purposes of clarity and conciseness of the description, not all of the numerous components shown in the figures are described. The numerous components are shown in the drawings to provide a person of ordinary skill in the art a thorough, enabling disclosure of the present specification. The operation of many of the components would be understood and apparent to one skilled in the art. Similarly, the reader is to understand that the specific ordering and combination of process actions described is merely illustrative, and the disclosure may be performed using different or additional process actions, or a different combination of process actions.

Each of the additional features and teachings disclosed herein can be utilized separately or in conjunction with other features and teachings for protective coverings. Representative examples using many of these additional features and teachings, both separately and in combination, are described in further detail with reference to the attached drawings. This detailed description is merely intended for illustration purposes to teach a person of skill in the art further details for practicing preferred aspects of the present teachings and is not intended to limit the scope of the claims. Therefore, combinations of features disclosed in the detailed description may not be necessary to practice the teachings in the broadest sense, and are instead taught merely to describe particularly representative examples of the present disclosure. Additionally and obviously, features may be added or subtracted as desired without departing from the broader spirit and scope of the disclosure. Accordingly, the disclosure is not to be restricted except in light of the attached claims and their equivalents.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help to understand how the present teachings are practiced, but not intended to limit the dimensions and the shapes shown in the examples.

None of the pending claims includes limitations presented in "means plus function" or "step plus function" form. (See, 35 USC § 112(f)). It is Applicant's intent that none of the claim limitations be interpreted under or in accordance with 35 U.S.C. § 112(f).

What is claimed is:

1. A method comprising:
determining, by a services platform based on personal information of a focal individual, a focal string;
retrieving, by the services platform from a reference database, a reference string of a reference individual;
computationally identifying, by the services platform, identity-by-descent (IBD) segments between the focal string and the reference string, wherein identifying IBD segments comprises:
in parallel:
(i) masking and unmasking locations of the focal string and the reference string in a sliding window according to a first mask pattern of consecutive locations; and identifying first matches among values of the focal string and the reference string at unmasked locations; and
(ii) masking and unmasking locations of the focal string and the reference string in a sliding window according to a second mask pattern of consecutive locations, wherein the second mask pattern is different from the first mask pattern; and identifying second matches among values of the focal string and the reference string at unmasked locations; and
merging the first matches and the second matches to produce a merged set of IBD segments;
determining, by the services platform and based on the merged set of IBD segments, a degree of relatedness between the focal individual and the reference individual; and
providing, by the services platform, access to the degree of relatedness via a user interface.

2. The method of claim 1, wherein the sliding window of the first mask and the sliding window of the second mask are each at least four consecutive locations in size.

3. The method of claim 1, wherein the focal individual is a user of the services platform.

4. The method of claim 1,
wherein computationally identifying IBD segments between the focal string and the reference string further comprises:
masking and unmasking locations of the focal string and the reference string in a sliding window according to a third mask pattern of consecutive locations, wherein the third mask pattern is different from the first mask pattern and the second mask pattern; and
identifying third matches among values of the focal string and the reference string at unmasked locations, and
wherein merging the first matches and the second matches to produce the merged set of IBD segments comprises merging the first matches, the second matches, and the third matches to produce the merged set of IBD segments.

5. The method of claim 1, wherein the focal individual is a human.

6. The method of claim 1, wherein each of the focal string and the reference string comprises at least one thousand strings.

7. The method of claim 1, wherein computationally identifying IBD segments between the focal string and the reference string comprises performing a positional Burrows-Wheeler transform (PBWT) on the unmasked locations produced by:

masking and unmasking locations of the focal string and the reference string in the sliding window according to the first mask pattern of consecutive locations; or
masking and unmasking locations of the focal string and the reference string in the sliding window according to the second mask pattern of consecutive locations.

8. The method of claim 7, wherein merging the first matches and the second matches is performed while considering individual locations of the focal string and the reference string using the PBWT.

9. The method of claim 1, wherein the first mask pattern of consecutive locations is determined deterministically.

10. The method of claim 9, wherein the first mask pattern varies based on a location of the sliding window with respect to the focal string or the reference string.

11. The method of claim 1, wherein the first mask pattern of consecutive locations is determined using a probabilistic function.

12. A system comprising:
one or more processors and associated memory; and
computer readable instructions that, when executed by the one or more processors, cause the one or more processors to:
determine, by a services platform based on personal information of a focal individual, a focal string;
retrieve, by the services platform from a reference database, a reference string of a reference individual;
computationally identify, by the services platform, identity-by-descent (IBD) segments between the focal string and the reference string, wherein identifying IBD segments comprises:
in parallel:
(i) masking and unmasking locations of the focal string and the reference string in a sliding window according to a first mask pattern of consecutive locations; and identifying first matches among values of the focal string and the reference string at unmasked locations; and
(ii) masking and unmasking locations of the focal string and the reference string in a sliding window according to a second mask pattern of consecutive locations, wherein the second mask pattern is different from the first mask pattern; and identifying second matches among values of the focal string and the reference string at unmasked locations; and
merging the first matches and the second matches to produce a merged set of IBD segments;
determine, by the services platform and based on the merged set of IBD segments, a degree of relatedness between the focal individual and the reference individual; and
provide, by the services platform, access to the degree of relatedness via a user interface.

13. The system of claim 12, wherein the sliding window of the first mask and the sliding window of the second mask are each at least four consecutive locations in size.

14. The system of claim 12,
wherein computationally identifying IBD segments between the focal string and the reference string further comprises:
masking and unmasking locations of the focal string and the reference string in a sliding window according to a third mask pattern of consecutive locations, wherein the third mask pattern is different from the first mask pattern and the second mask pattern; and identifying third matches among values of the focal string and the reference string at unmasked locations, and wherein merging the first matches and the second matches to produce the merged set of IBD segments comprises merging the first matches, the second matches, and the third matches to produce the merged set of IBD segments.

15. The system of claim 12, wherein the focal individual is a human, and wherein the focal individual is a user of the services platform.

16. The system of claim 12, wherein each of the focal string and the reference string comprises at least one thousand strings.

17. The system of claim 12, wherein computationally identifying IBD segments between the focal string and the reference string comprises performing a positional Burrows-Wheeler transform (PBWT) on the unmasked locations produced by:

masking and unmasking locations of the focal string and the reference string in the sliding window according to the first mask pattern of consecutive locations; or masking and unmasking locations of the focal string and the reference string in the sliding window according to the second mask pattern of consecutive locations.

18. The system of claim 17, wherein merging the first matches and the second matches is performed while considering individual locations of the focal string and the reference string using the PBWT.

19. The system of claim 12, wherein the first mask pattern of consecutive locations is determined deterministically.

20. The system of claim 12, wherein the first mask pattern of consecutive locations is determined using a probabilistic function.

* * * * *